(12) United States Patent
Raines et al.

(10) Patent No.: US 9,162,999 B2
(45) Date of Patent: Oct. 20, 2015

(54) CATALYTIC CONVERSION OF CELLULOSE TO FUELS AND CHEMICALS USING BORONIC ACIDS

(71) Applicants: Ronald Raines, Madison, WI (US); Benjamin Caes, West Des Moines, IA (US); Michael Palte, Madison, WI (US)

(72) Inventors: Ronald Raines, Madison, WI (US); Benjamin Caes, West Des Moines, IA (US); Michael Palte, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 66 days.

(21) Appl. No.: 13/629,588

(22) Filed: Sep. 27, 2012

(65) Prior Publication Data

US 2013/0178617 A1    Jul. 11, 2013

Related U.S. Application Data

(60) Provisional application No. 61/540,382, filed on Sep. 28, 2011.

(51) Int. Cl.
| | | |
|---|---|---|
| *C07D 307/50* | (2006.01) | |
| *B01J 27/20* | (2006.01) | |
| *B01J 21/02* | (2006.01) | |
| *B01J 23/92* | (2006.01) | |
| *B01J 27/32* | (2006.01) | |
| *C07D 307/48* | (2006.01) | |
| *B01J 31/14* | (2006.01) | |
| *B01J 27/08* | (2006.01) | |
| *B01J 37/02* | (2006.01) | |

(52) U.S. Cl.
CPC ............... *C07D 307/50* (2013.01); *B01J 21/02* (2013.01); *B01J 23/92* (2013.01); *B01J 27/20* (2013.01); *B01J 27/32* (2013.01); *B01J 31/146* (2013.01); *C07D 307/48* (2013.01); *B01J 27/08* (2013.01); *B01J 37/0209* (2013.01); *B01J 2231/641* (2013.01)

(58) Field of Classification Search
CPC ..... C07D 307/50; C07D 307/48; B01J 27/20; B01J 21/02; B01J 23/92; B01J 27/32; B01J 31/146; B01J 2231/641; B01J 37/0209; B01J 27/08
USPC .................... 536/124; 502/169, 172; 549/489
See application file for complete search history.

(56) References Cited

U.S. PATENT DOCUMENTS

| | | | |
|---|---|---|---|
| 4,269,605 A * | 5/1981 | Dean et al. ...................... | 436/67 |
| 4,764,627 A | 8/1988 | Diebold et al. | |
| 4,780,552 A | 10/1988 | Wambach et al. | |
| 5,512,464 A | 4/1996 | Spencer et al. | |
| 5,593,868 A | 1/1997 | Spencer et al. | |
| 5,773,648 A | 6/1998 | Becker et al. | |
| 5,880,198 A | 3/1999 | Kobayashi et al. | |
| RE36,719 E | 5/2000 | Tustin et al. | |
| 6,607,603 B1 | 8/2003 | Fougnies | |
| 6,855,822 B2 | 2/2005 | Liao et al. | |
| 7,582,621 B2 | 9/2009 | Baker et al. | |
| 7,767,657 B2 | 8/2010 | Baker et al. | |
| 7,816,344 B2 | 10/2010 | Baker et al. | |
| 2008/0227162 A1 | 9/2008 | Varanasi et al. | |
| 2012/0301948 A1* | 11/2012 | Brennan et al. ............... | 435/243 |

FOREIGN PATENT DOCUMENTS

| | | |
|---|---|---|
| WO | WO 2008/112291 | 9/2008 |
| WO | WO 2011/133536 | 10/2011 |

OTHER PUBLICATIONS

Defieber et al. Chiral [2.2.2] Dienes as Ligands for Rh(I) in Conjugate Additions of Boronic Acids to a Wide Range of Acceptors. Organic Lett 6:3873-3876, 2004.*
Middle et al. Separation of glycosylated haemoglobins using immobilized phenylboronic acid. Biochem J 209:771-779, 1983.*
Acree (1973) "The Chemistry of sugars in boric-acid solutions," *Adv. Chem. Ser.* 117:208-219.
Berube et al. (2008) "Benzoboroxoles as efficient glycopyranoside-binding agents in physiological conditions: Structure and selectivity of complex formation," *J. Org. Chem.* 73:6471-6479.
Binder et al. (Jan. 2009) "Simple chemical transformation of lignocellulosic biomass into furans for fuels and chemicals," *J. Am. Chem. Soc.* 131:1979-1985.
Binder et al. (Mar. 1, 2010) "Fermentable sugars by chemical hydrolysis of biomass," *Proc. Natl. Acad. Sci. U.S.A.* 107:4516-4521.
Brandenberg et al. (1950) "Olefins from alcohols," *J. Am. Chem. Soc.* 72:3275-3276.
Caes (Jul. 2012) "Catalytic Systems for Carbohydrate Conversion," PhD Dissertation. University of Wisconsin-Madison.
Caes et al. (Feb. 2011) "Conversion of Fructose into 5-(Hydroxymethyl)furfural in Sulfolane," *ChemSusChem.* 4:353-356.
Caes et al. (Oct. 2012) "Organocatalytic conversion of cellulose into a platform chemical," *Chem. Sci.* 4:196-199.
Cuthbertson (2008) "Boronic Acids: Properties and Applications," *Alfa Aesar.* Heysham, United Kingdom.

(Continued)

*Primary Examiner* — Mark Shibuya
*Assistant Examiner* — Yih-Horng Shiao
(74) *Attorney, Agent, or Firm* — Lathrop & Gage LLP

(57) ABSTRACT

Methods and catalyst compositions for formation of furans from carbohydrates. A carbohydrate substrate is heating in the presence of a 2-substituted phenylboronic acid (or salt or hydrate thereof) and optionally a magnesium or calcium halide salt. The reaction is carried out in a polar aprotic solvent other than an ionic liquid, an ionic liquid or a mixture thereof. Additional of a selected amount of water to the reaction can enhance the yield of furans.

24 Claims, 8 Drawing Sheets

(56) References Cited

OTHER PUBLICATIONS

Dowlut et al. (2006) "An improved class of sugar-binding boronic acids, soluble and capable of complexing glycosides in neutral water," *J. Am. Chem. Soc.* 128:4226-4227.

Ellis et al. (Feb. 2012) "Boronate-mediated biologic delivery," *J. Am. Chem. Soc.* 134:3631-3634.

Hall (2005) "Structure, Properties, and Preparation of Boronic Acid Derivatives," In; Ch. 1 *Boronic Acids: Preparation and Application in Organic Synthesis and Medicine.* John Wiley and Sons. pp. 1-99.

Hansen et al. (Feb. 2011) "Ortho-substituted aryl monoboronic acids have improved selectivity for d-glucose relative to d-fructose and l-lactate," *Tetrahedron.* 67:1334-1340.

Hansen et al. (Nov. 2010) "Synergy of boric acid and added salts in the catalytic dehydration of hexoses to 5-hydroxymethylfurfural in water," *Green Chem.* 13:109-114.

International Preliminary Report on Patentability corresponding to International Patent Application No. PCT/US12/57674, completed Apr. 1, 2014.

International Search Report with Written Opinion corresponding to International Patent Application No. PCT/US12/57674, mailed Feb. 22, 2013.

Kawamoto et al. (2008) "Inhibition of acid-catalyzed depolymerization of cellulose with boric acid in non-aqueous acidic media," *Carbohydr. Res.* 343:249-255.

Kawamoto et al. (2008) "Stable complex formation with boric acid in pyrolysis of levoglucosan in acidic media," *J. Anal. Appl. Pyrol.* 82:78-82.

Mulla et al. (2004) "3-Methoxycarbonyl-5-nitrophenylboronic acid: High affinity diol recognition at neutral pH," *Bioorg. Med. Chem. Lett.* 14:25-27.

Mylavarapu et al. (2007) "Boric Acid Catalyzed Amidation in the Synthesis of Active Pharmaceutical Ingredients," *Organic Process Research and Development.* 11:1065-1068.

O'Connor et al. (1955) "The boric acid dehydration of alcohols," *J. Am. Chem. Soc.* 77:1578-1581.

Springsteen et al. (2002) "A detailed examination of boronic acid—diol complexation," *Tetrahedron.* 58:5291-5300.

Ståhlberg et al. (Jan. 2011) "Metal-free dehydration of glucose to 5-(hydroxymethyl)furfural in ionic liquids with boric acid as promoter," *Chem. Eur. J.* 17:1456-1464.

Takasaki (1971) "Studies on Sugar-isomerizing Enzymes Effect of Borate on Glucose-fructose Isomerization Catalyzed by Glucose Isomerase," *Agr. Biol. Chem.* 35(9):1371-1375.

Tao et al. (2002) "A Practical Preparation of 2-Carboxyphenylboronic Acid and its Applications for Preparation of Biaryl-2-Carboxylic Acids Using Suzuki Coupling Reactions," *Synthesis.* 8:1043-1046.

\* cited by examiner (I) hydrolysis; (II) isomerization; (III) dehydration
SCHEME 1

SCHEME 2

SCHEME 3

SCHEME 5-2

SCHEME 6

US 9,162,999 B2

CATALYTIC CONVERSION OF CELLULOSE TO FUELS AND CHEMICALS USING BORONIC ACIDS

CROSS-REFERENCE TO RELATED APPLICATIONS

This application claims the benefit of U.S. provisional application 61/540,382, filed Sep. 28, 2011, which application is incorporated by reference herein in its entirety.

STATEMENT REGARDING GOVERNMENT FUNDING

This invention was made with government support under DE-FC02-07ER64494 awarded by the US Department of Energy and GM044783 awarded by the National Institutes of Health. The government has certain rights in the invention.

BACKGROUND OF THE INVENTION

Petroleum, coal, and natural gas are three indispensable resources that support modern civilization and have propelled the rise of advanced technologies. Presently, fossil fuel resources account for 86% of the world's energy supply, as well as 96% of its organic chemicals (US National Petroleum Council, 2007). These values are unsustainable, given the increasing demand for energy and chemicals coupled with the diminishing supply of fossil fuels. In addition, rising $CO_2$ emissions, decreasing accessibility to fossil fuel resources, and increasing consumer costs mandate a reduction in fossil fuel consumption (Kramer & Haigh, 2009; Tilman et al. 2009). Abundant, renewable biomass resources are able to meet this rising demand and alleviate these environmental and socioeconomic concerns.

If biomass is to replace fossil fuels as an energy and chemical resource, it must match the wide array of products derived from fossil fuel reserves. Obtaining furans from biomass is of significant current interest. The six-carbon furanic 5-(hydroxymethyl)furfural (HMF) holds great potential to meet this challenge (Antal et al., 1990; Chheda et al., 2007; Huber et al., 2005); Lewkowski, 2001; Roman-Leshkov et al., 2007; Roman-Leshkov et al., 2006). The carbon skeleton of HMF is identical to those found in the hexose sugars, which are the primary components of cellulose and hemicelluloses found in biomass. Additionally, by utilizing straightforward chemical methods, HMF can be transformed into a variety of useful products including acids, aldehydes, alcohols, and amines, such as common polyester building blocks 2,5-furandicarboxylic acid, 2,5-bis(hydroxymethyl)furan, and 2,5-bis(hydroxymethyl) tetrahydrofuran (Chheda et al., 2007; Huber et al., 2005; Lewkowski 2001; Roman-Leshkov, 2006) as well as the promising liquid fuel 2,5-dimethylfuran (Roman-Leshkov, 2007).

Furfural is perhaps the most common industrial chemical derived from lignocellulosic biomass with an annual production of more than 200,000 t (Kamm et al. 2006). The conversion of pentoses into furfural has been reported (Sproull et al., 1985; Moreau et al., 1988; Mansilla et al. 1998; Dias et al. 2007). Most industrial processes achieve yields in the range of 50 molar %, which may be limited by homopolymerization and condensation with unreacted xylose. In typical processes reported, Brønsted acidic catalysts were used in aqueous solution at temperatures greater than 150° C. (Moreau et al., 1998; Dias et al., 2007).

The conversion of cellulose to HMF proceeds through three steps: hydrolysis of cellulose to glucose, isomerization of glucose to fructose, and dehydration of fructose to HMF (see Scheme 1, FIG. 1, below). A number of processes have been reported to transform glucose and fructose into HMF, though few processes can access HMF in high yields directly from cellulose (Moreau et al., 2000; Seri et al., 2001; Watanabe et al., 2005a; Watanabe et al., 2005b; Yan et al., 2009; Tyrlik et al., 1999; Hu et al., 2009; Ståhlberg et al. 2010; Zhao et al. 2007; Pidko et al., 2010). Both xylan and xylose can be dehydrated into furfural (Zeitsch, 2000; Mamman et al. 2008). Scheme 2 illustrates the formation of furfural from xylan and xylose. In this scheme, the C-2 hydroxyl group is displaced to form a xylose-2,5-anhydride and subsequent dehydration steps produce furfural (Antal et al., 1991; Nimlos et al., 2006).

An important goal in the art is direct conversion of biomass to HMF and other furans. Recent developments in conversion technologies using solid acid or base (Carlini et al., 1999; Zhao et al. 2011), or heavy metal catalysts (Binder & Raines, 2009; Su et al., 2009) have shown progress toward this goal. The lack of cellulose conversion by solid acid catalysts and the reported environmental toxicity of heavy metals represent practical problems for implementation of such processes. With today's emphasis on "green" chemistry, it is very desirable that a conversion process to HMF use mild reaction conditions to transform cellulose as well as other carbohydrates with recyclable and environmentally benign reagents, catalysts, and solvents. While processes for generating HMF, furfural and other furans are known in the art (e.g., U.S. Pat. Nos. 7,572,925 and 7,880,049; US 2008/0033187; Zhao et al. 2007; JP 2005232116) there remains a need in the art for conversion processes that efficiently and selectively convert carbohydrates to HMF and other furans. Such efficient and selective processes must be available for biomass to become a viable feedstock for energy and chemicals.

Boric acid is an environmentally benign catalyst that is utilized for the dehydration of alcohols (Brandenberg & Galat, 1950; O'Connor & Nace, 1955).

However, boric acid and phenylboronic acid have both been reported to be inhibitory towards the hydrolysis of cellulose and the dehydration of sugar monomers in a non-aqueous medium; and inhibition was indicated to be due to the stability of cyclic boronate esters to decomposition and dehydration (Kawamoto et al. 2008a; Kawamoto et al. 2008b). More specifically, Kawamoto et al. 2008a reports that boric acid inhibited acid-catalyzed depolymerization of cellulose, and inhibited the formation of dehydration products, including HMF, in sulfolane at high temperature. Kawamoto et al. 2008b reports that boric acid and phenylboronic acid suppressed acid-catalyzed dehydration and formation of furfurals from levoglucosan. In both reports, inhibition or suppression is indicated to be due to stable boronate complex formation. However, Hansen et al. 2011 and Ståhlberg et al. 2011 recently reported that boric acid itself can promote dehydration of hexoses to HMF.

SUMMARY OF THE INVENTION

The present invention provides methods for producing furans, including HMF and/or furfural, from carbohydrates including glucose, fructose and other sugars, oligosaccharides, such as cellobiose, polysaccharides, such as cellulose, hemicellulose and xylan, and lignocellulosic biomass employing certain substituted phenylboronic acids, particularly certain 2-substituted (ortho-substituted) phenylboronic acids, to enhance conversion to the furans.

More specifically, in methods of the invention, generation of furans from such carbohydrates is catalyzed or promoted by certain substituted phenylboronic acids alone or in combination with anhydrous or hydrated magnesium or calcium halide salts, particularly anhydrous or hydrated $MgCl_2$. In specific embodiments, the substituted phenylboronic acids are those carrying a 2-nitro, 2-alkyl, 2-alkoxy, 2-haloalkyl, a 2-aminocarbonyl, a 2-, 3-, 4- or 5-haloalkyl group, a 2-, 3- or 4-carboxy or a 2-, 3-, or 4-alkoxycarbonyl group. In specific embodiments, the substituted phenylboronic acids are 2-substituted phenylboronic acids. The substituted phenylboronic acids as described above can in addition carry one to four and more preferably one or two, additional substitutents as defined below. The phenylboronic acid is optionally in the form of a hydrate (e.g., a monohydrate) or a salt. Preferred 2-substituted phenylboronic acids are 2-carboxy and 2-alkoxycarbonyl phenylboronic acids, where the alkoxy group has 1-3 carbon atoms.

In specific embodiments, the additional substituents of the substituted phenylboronic acids are one or more electron withdrawing groups. In specific embodiments, additional substituents are selected from the group consisting of halogen, nitro, cyano, an alkyl group, an alkoxy group, an alkoxycarbonyl group, a carboxyalkyl group, an alkoxycarbonylalkyl group, an aminoalkyl group, an alkylaminoalkyl group, —COH, —COR$_7$, —CO$_2$H, —CO$_2$R$_8$, —NH$_2$, —CONH$_2$, —N(R$_9$)$_2$, or —CON(R$_9$)$_2$, where R$_7$, R$_8$ and each R$_9$ is independently selected from an alkyl group, an aralkyl group or an aryl group. Alkyl, alkoxy, aralkyl and aryl groups of the substituents herein are optionally substituted as defined herein.

Preferred alkyl and alkoxy substituents have 1-3 carbon atoms. Preferred R$_7$ and R$_8$ of substituents herein are hydrogen, alkyl having 1-3 carbons, phenyl and benzyl groups. In specific embodiments, alkyl, alkoxy, aralkyl and aryl groups of substituents herein are unsubstituted. In specific embodiments, alkyl aralkyl and aryl groups are substituted with one or more halogens. In specific embodiments, haloalkyl groups are perfluoroalkyl groups, particularly those having 1-3 carbon atoms. In specific embodiments, halogen substituents are F, Cl or Br and in more specific embodiments, halogens are chlorines.

In specific embodiments, the substituted phenylboronic acid is a carboxy or alkoxycarbonyl substituted phenylboronic acid, particularly a phenylboronic acid substituted with a 2-carboxy, a 2-methoxycarbonyl or a 2-ethoxycarbonyl group and optionally further substituted as noted above. Specific additional substituents for 2-carboxy, a 2-methoxycarbonyl or a 2-ethoxycarbonyl phenylboronic acids are selected from the group consisting of methyl, ethyl, methoxy, ethoxy, chloro, fluoro, cyano, nitro, trifluoromethyl, formyl, acetyl, —NH$_2$, —CONH$_2$, and N,N-dimethylaminomethyl.

In the methods of the invention the carbohydrate is contacted at a selected temperature with the phenylboronic acid alone or in combination with an anhydrous or hydrated magnesium or calcium halide salt, particularly an anhydrous or hydrated magnesium or calcium chloride in an appropriate solvent. The phenylboronic acid is optionally in the form of a hydrate or a salt.

In specific embodiments, addition of selected amounts of water to the reaction can enhance the yield of desired furan products. Reaction is typically continued to obtain a desired yield of furan(s). It is preferred to maximize the yield of furans (i.e., HMF and/or furfural) and minimize undesirable side-products, for example, from degradation or polymerization of the desired furan products.

In specific embodiments, the invention provides methods for producing HMF from ketohexose, particularly glucose, and aldohexoses, particularly galactose, in the presence of certain substituted phenylboronic acids, particularly those carrying a 2-methoxycarbonyl or a 2-ethoxycarbonyl group. The phenylboronic acids may carry one to four or one or two additional substituents as noted above. In these cases, no metal salt is required for production of HMF. However, the addition of an anhydrous or hydrated magnesium and calcium chloride can enhance the yield of HMF. The addition of water to the reaction can enhance the yield of HMF. In another specific embodiment, mono- and disaccharides are converted to the furans, HMF and/or furfural, in the presence of certain 2-substituted phenylboronic acids, and a hydrated magnesium or calcium halide salt in polar aprotic solvent other than an ionic liquid, an ionic liquid or mixtures thereof. In another specific embodiment, mono- and disaccharides are converted to HMF and/or furfural, in the presence of certain phenylboronic acids, and a hydrated magnesium or calcium halide salt in an ionic liquid. In a specific embodiment the furan is HMF. In another embodiment the furan is furfural. In yet another embodiment a mixture of HMF and furfural is generated.

In additional embodiments, the invention provides methods for producing HMF from glucose in a dipolar aprotic solvent other than an ionic liquid in the presence of certain substituted phenylboronic acids, particularly 2-carboxy-substituted phenylboronic acids, 2-methoxycarbonyl-substituted phenylboronic acids, 2-ethoxycarbonyl-substituted phenylboronic acids, or 3-carboxy-5-nitrophenylboronic acid. In these cases, no metal salt is required to produce HMF. However, the addition of an anhydrous or hydrated magnesium or calcium chloride can enhance the yield of HMF. The addition of water to the reaction can enhance the yield of HMF.

In a specific embodiment, hexose oligomers, pentose oligomers and mixtures thereof are converted to furans at high yields by reaction with certain 2-substituted phenylboronic acids in a dipolar aprotic solvent other than an ionic liquid in the absence of magnesium or calcium salt and in the absence of added water. Addition of anhydrous or hydrated magnesium or calcium halide can enhance the production of furans. Addition of a selected amount of water can enhance the production of furans. More specifically, glucose oligomers, such as cellobiose, cellotriose, or cellotetrose, are converted to HMF at high yields by reaction with certain 2-substituted phenylboronic acids in a dipolar aprotic solvent other than an ionic liquid (e.g., DMA) in the absence of magnesium or calcium salt and in the absence of added water. Addition of anhydrous or hydrated magnesium or calcium halide can enhance the production of furans. Addition of a selected amount of water can enhance the production of furans.

In a specific embodiment, cellulose, hemicellulose, or lignocellulosic biomass is converted to furans in the presence of certain 2-substituted phenylboronic acids, and dilute mineral or organic acid (other than a boronic acid) in ionic liquid or a mixture of ionic liquid and a dipolar aprotic solvent other than an ionic liquid (e.g., DMA). Preferably an anhydrous or hydrated magnesium or calcium halide is added to enhance production of furans. Addition of a selected amount of water can enhance production of furans.

In an embodiment, the present invention also provides a method for producing fructose by reacting glucose or glucose oligomers in the presence of certain 2-substituted phenylboronic acids and magnesium oxide in a dipolar aprotic solvent other than an ionic liquid, an ionic liquid or mixtures thereof.

In specific embodiments, the methods of the invention employ 2-substituted phenylboronic acids which are immobilized on a solid substrate, such as a substrate surface or a resin. In specific embodiments, the 2-substituted phenylboronic acids are immobilized to the surface by covalent attachment by a linker moiety to the surface or resin. In specific embodiments, covalent attachment can be to the 4- or 5-ring position of the phenyl ring of the 2-substituted phenylboronic acid. The use of immobilized phenylboronic acids facilitates their recycling and reuse and facilitates product recovery and purification.

In an embodiment the invention provides catalyst compositions for formation of furans from carbohydrates, including mono- and disaccharides, cellulose and other polymers and lignocellulosic biomass. Catalyst compositions comprise one or more 2-substituted phenylboronic acids, including salts and hydrates thereof. In specific embodiments, catalyst compositions comprise one or more 2-substituted phenylboronic acids immobilized on a solid, such as a substrate surface or a resin. In specific embodiments, catalyst compositions comprise one or more 2-substituted phenylboronic acids in combination with a magnesium or calcium chloride salt or mixture of such halide salts. In specific embodiments, the magnesium or calcium halide salt is hydrated. In specific embodiments, the halide salt is $MgCl_2$. In specific embodiments, the salt is $MgCl_2.6H_2O$. In specific embodiments, the substituted phenylboronic acids are those carrying a 2-nitro, 2-alkyl, 2-alkoxy, 2-haloalkyl, a 2-aminocarbonyl, a 2-, 3-, 4- or 5-haloalkyl group, a 2-, 3- or 4-carboxy or a 2-, 3-, or 4-alkoxycarbonyl group. In specific embodiments, the substituted phenylboronic acids of the compositions are 2-substituted phenylboronic acids. The substituted phenylboronic acids as described above can in addition carry one to four and more preferably one or two, additional substitutents as defined below. The phenylboronic acid is optionally in the form of a hydrate (e.g., a monohydrate) or a salt. Preferred 2-substituted phenylboronic acids are 2-carboxy and 2-alkoxycarbonyl phenylboronic acids, where the alkoxy group has 1-3 carbon atoms.

In an embodiment, the invention further provides a carbohydrate dehydration medium which comprises a catalyst composition for formation of HMF as provided herein in ionic liquid, a polar aprotic solvent other than an ionic liquid or a mixture thereof. In specific embodiments, the carbohydrate dehydration medium contains a selected amount of water. In specific embodiments, when the carbohydrate comprises a polysaccharide, such as cellulose, the carbohydrate dehydration medium can comprise an acid other than a phenylboronic acid. In specific embodiments, the carbohydrate dehydration medium comprises dilute organic or mineral acid.

In a specific embodiment, 2-substituted phenylboronic acids useful in the methods and catalyst compositions of this invention are those of formula I:

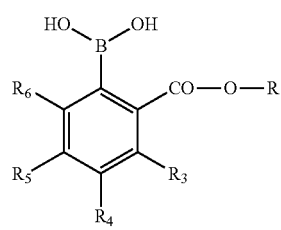

where:
R is selected from an alkyl group, a hydrogen, an aralkyl group, or an aryl group, each of which is optionally substituted;

$R_3$-$R_6$, independently, are selected from hydrogen, halogen, nitro, cyano, an alkyl group, an alkoxy group, an alkoxycarbonyl group, a carboxyalkyl group, an alkoxycarbonylalkyl group, an aminoalkyl group, an alkylaminoalkyl group, —COH, —$COR_7$, —$CO_2R_8$—$NH_2$, —$CONH_2$, —$N(R_9)_2$, or —$CON(R_9)_2$, where $R_7$, $R_8$ and each $R_9$ is independently selected from an alkyl group, an aralkyl group or an aryl group. Alkyl, alkoxy, aralkyl and aryl groups of the substituents herein are optionally substituted. Preferred alkyl and alkoxy substituents are have 1-3 carbon atoms.

Preferred $R_7$ and $R_8$ of substituents herein are hydrogen, alkyl having 1-3 carbons, phenyl and benzyl groups. In specific embodiments, alkyl, alkoxy, aralkyl and aryl groups of substituents herein are unsubstituted. In specific embodiments, haloalkyl groups are perfluoroalkyl groups, particularly those having 1-3 carbon atoms. In specific embodiments, halogen substituents are F, Cl or Br and in more specific embodiments, halogens are chlorines.

In another specific embodiment of formula I, one of $R_3$-$R_6$ is (1) a linker group covalently attached to a surface, (2) a linker group suitable for attachment of the phenylboronic acid to a surface or (3) a reactive group with optional linker suitable for forming a covalent attachment to a surface directly or through a linker.

In a specific embodiment, alkyl, alkoxy, aralkyl, aryl and other groups in the definitions herein are optionally substituted with one or more halogen, hydroxyl, nitro, cyano, alkyl, haloalkyl, aryl, amine, alkoxy, —$COOR_{10}$, —$COR_{10}$, —$SR_{10}$, or —CO—$N(R_{10})$ groups, where $R_{10}$ is hydrogen or an alkyl, aralkyl or aryl group. In specific embodiments, substituents for optional substitution are one or more halogen, one or more alkyl having 1-3 carbon atoms, an amine, an alkoxy having 1-3 carbon atoms, a trifluoromethyl group, —COOH, —$COOCH_3$, or —$COOC_2H_5$.

In specific embodiments, R is hydrogen or an unsubstituted alkyl group having 1-3 carbon atoms. In specific embodiments, alkyl and alkoxy groups have 1-3 carbon atoms. In specific embodiments, alkyl, alkoxy, aralkyl and aryl groups are unsubstituted. In other specific embodiments, alkyl, alkoxy, aralkyl and aryl groups are substituted. More specifically, alkyl, alkoxy, aralkyl, or aryl groups are substituted with one or two non-hydrogen substituents. In specific embodiments, substituted alkyl groups, aryl groups, aralkyl, benzyl or phenyl groups are substituted with one or more halogens. In specific embodiments, substituted alkyl groups, aralkyl groups, aryl groups, benzyl groups or phenyl groups are perhalogenated. In specific embodiments, halogen substituents are chlorine and fluorine. In specific embodiments, halogen substituents are chlorine. In specific embodiments, when aryl groups are phenyl groups and aralkyl groups are benzyl groups, these groups are unsubstituted or are substituted with one to five non-hydrogen substituents and particularly with one to five halogens.

In specific embodiments, R is hydrogen or an alkyl group having 1-3 carbon atoms. Phenylboronic acids may be in the form of salts with an appropriate anion or cation. Phenylboronic acids may be in the form of hydrates, particularly monohydrates.

In specific embodiments, R, $R_7$ or $R_8$ which are aryl groups are phenyl groups. In specific embodiments, R, $R_7$ or $R_8$ which are aralkyl groups are benzyl groups.

In yet more specific embodiments, $R_3$-$R_6$ are all hydrogens, one or two of $R_3$-$R_6$ are alkyl and the remainder are hydrogen, one or two of $R_3$-$R_6$ are halogens and the remainder are hydrogen, one or two of $R_3$-$R_6$ are alkoxy and the remainder are hydrogens, one or two of $R_3$-$R_6$ are halogenated alkyl groups and the remainder are hydrogen, one or two of $R_3$-$R_6$ are halogenated alkoxy groups and the remainder are hydrogens, one or two of $R_3$-$R_6$ are nitro groups and the remainder are hydrogens.

In specific embodiments, reactive groups suitable for forming a covalent attachment to a surface through a linker are exemplified by —$CO_2R_{10}$, —$N(R_{11})_2$, —$NO_2$, alkyl halide, vinyl, —$OR_{12}$, or —$SR_{12}$ groups, where $R_{10}$, $R_{11}$ or $R_{12}$ is selected from hydrogen, an alkyl group, an aryl group or an aralkyl group.

The invention also relates to methods for making useful derivatives and products of HMF such as 2,5-furandicarboxylic acid, 2,5-bis(hydroxymethyl)furan, 2,5-bis(hydroxymethyl) tetrahydrofuran and 2,5-dimethylfuran by initial production of HMF by a method of this invention.

The methods of the invention employ solvents which are dipolar aprotic solvents (other than ionic liquids), ionic liquids or mixtures thereof. In specific embodiments, useful dipolar aprotic solvents include N,N-dimethylacetamide (DMA), N,N-diethylacetamide (DEA), dimethylformamide (DMF), N-methylpyrrolidone, 1-ethyl-2-pyrrolidinone, methylsulfonylmethane, sulfolane, 3-methylsulfolane, 2,4-dimethylsulfolane, dimethylsulfoxide, diethylsulfoxide, N-methylcaprolactam, N,N-dimethylpropionamide, 1-pyrrolidine carboxaldehyde; or miscible mixtures thereof. Preferred dipolar aprotic solvents other than ionic liquids are DMA and N-methylpyrrolidone. Various ionic liquids can be employed in the methods of this invention. In particular, ionic liquids having chlorine anions can be employed.

In specific embodiments, the ionic liquid is an alkylimidazolium ionic liquid or an alkylpyridinium ionic liquid. In more specific embodiments, the ionic liquid is [EMIM]Cl (1-ethyl-3-methylimidazolium chloride), [BMIM]Cl (1-butyl-3-methyl-imidazolium chloride), 1-ethyl-2,3-dimethylimidazolium chloride, or 1-butyl-4-methylpyridinium chloride or mixtures thereof.

In specific embodiments, reactions of the invention are conducted at temperatures ranging from about 100 to 150° C., more specifically from 100 to 130° C. or from 105 to 130° C.

Other aspects and embodiments of the invention will be apparent on review of the drawings, description and examples that follow.

BRIEF DESCRIPTION OF THE DRAWINGS

FIG. 5-1 and FIG. 5-2 provide Scheme 5 which illustrates exemplary methods for immobilization of 2-substituted phenylboronic acids. The reactions in this scheme may be supplemented by initial protection of the 2-substituted phenylboronic acid prior to immobilization which protection can be removed after immobilization.

DETAILED DESCRIPTION OF THE INVENTION

Figure 1:
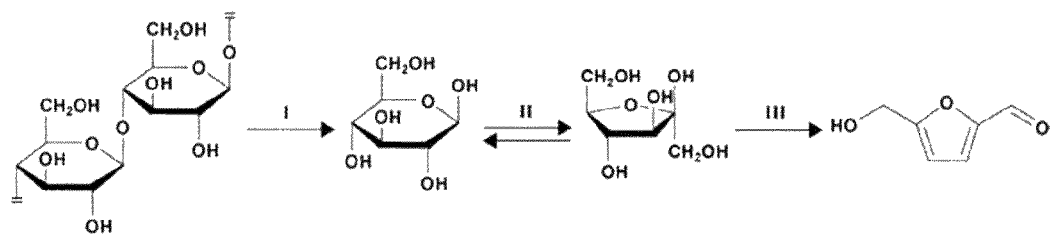
FIG. 1 provides Scheme 1 which schematically illustrates production of HMF from cellulose by hydrolysis (I) to generate glucose, isomerization of glucose (II) to fructose and dehydration of fructose (III).

Schemes 1 and 2 (FIGS. 1 and 2) illustrate generation of furans from carbohydrates. Scheme 1 (FIG. 1) illustrates generation of HMF from glucose, cellulose and lignocellulosic biomass (e.g., corn stover). Scheme 2 (FIG. 2) illustrates generation of furfural from xylose. The invention is based at least in part on the finding that certain 2-substituted (ortho-substituted) phenylboronic acids and hydrates thereof promote the formation of furans from carbohydrates (mono-, di- and oligosaccharides and polysaccharides) and lignocellulosic biomass, e.g., corn stover. In one aspect, in methods of this invention carbohydrates or lignocellulosic biomass is contacted with the 2-substituted phenylboronic acid salt (or hydrate) and a magnesium or calcium salt (or hydrate thereof) in an ionic liquid, a polar aprotic solvent other than an ionic liquid or a mixture thereof. Water can be present in the reaction either added in hydrated reaction components, present in the substrate carbohydrate or biomass or as added to the reaction. The presence of selected amounts of water can enhance furan production.

Dilute acid (other than a phenylboronic acid), particularly mineral acid, is added to facilitate hydrolysis of carbohydrate polymers when necessary.

In specific embodiments, reactions are conducted at temperatures ranging from about 100 to 150° C., more specifically from 100 to 130° C. and yet more specifically from about 105 to 130° C. It will be appreciated that it can be preferred to run a reaction at the lowest temperature that will provide a desired product yield to decrease energy costs. Typically reactions are run at ambient pressure, but can be conducted at elevated pressures.

In specific embodiments, the salt is a magnesium salt. In other specific embodiments, the salt is a calcium salt. In specific embodiments, the salt is magnesium halide or calcium halide. In specific embodiments, the salt is magnesium chloride or calcium chloride. Mixtures of such salts can be employed. In specific embodiments, the salt is hydrated magnesium chloride. In specific embodiments, no Li is added to or present in the reaction medium. In specific embodiments, no LiCl is added to the reaction. In specific embodiments, no metal salts other than magnesium and/or calcium chloride salts are added to or present in the reaction medium.

In specific embodiments, magnesium(II) and/or calcium (II) is present in the reaction in a total amount greater than 10 mol % with respect to the carbohydrate substrate. In specific embodiments, magnesium(II) or calcium(II) or a mixture thereof is present in the reaction in a total amount of 100 mol % to 500 mol % with respect to the carbohydrate substrate. In specific embodiments, magnesium(II) or calcium(II) or a mixture thereof is present in the reaction in a total amount of 100 mol % to 300 mol %.

In specific embodiments, the molar ratio of phenylboronic acid to magnesium(II) and/or calcium(II) or a mixture thereof in the reaction, in catalyst compositions or in carbohydrate dehydration medium is 0.5 to 5. In other embodiments, the molar ratio of phenylboronic acid to magnesium(II) or calcium(II) or a mixture thereof is 1 to 3. In other embodiments, the molar ratio of phenylboronic acid to magnesium(II) or calcium(II) or a mixture thereof is 2.

Without wishing to be bound to any particular mode of action, it is presently considered that the phenylboronic acids employed in the reactions herein bind to sugars facilitating the conversions and preventing at least in part the undesired polymerization of sugars. The phenylboronic acids are believed to act as catalysts or promoters which can be recovered from the reaction mixtures. The ability to recover phenylboronic acids for recycling and reuse can result in decreased costs for carrying out conversions of this invention. Recovery and recycling of phenylboronic acids can be facilitated by immobilizing the phenylboronic acid on a solid. An exemplary catalyst recycling and recovery process is provided in Example 7 and illustrates in FIG. 8. This process also provides for recovery of product furan.

Figure 8:
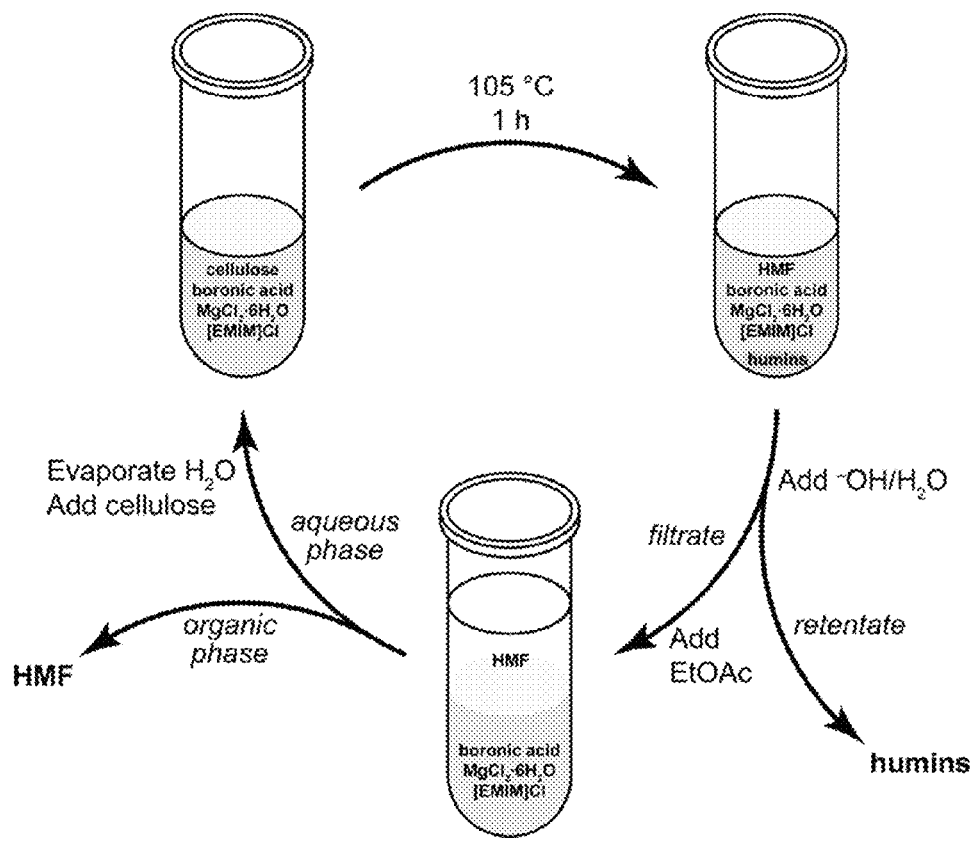
FIG. 8 illustrates an exemplary phenylboronic catalyst recovery and recycling process which is described in Example 7.

Reaction can be carried out in a batch mode or a continuous or semi-continuous mode. Reaction is carried out until a desired level of product is formed. In batch mode, the exact length of reaction will be dependent upon the temperature, concentration of reagents and the amount and type of substrate (carbohydrate/biomass). In specific embodiments, reactions are carried out for 0.5-24 hours, more preferably for 1-10 hours and yet more preferably in 1-4 hours. The length of time the reaction is run can be optimized by assessing product yield as a function of reaction time for a given set of reaction conditions. Catalyst and salt concentration and the amount of water can be varied to achieve desired yields. In continuous or semi-continuous mode, products are periodically removed from the reaction. Various methods for removal of furans from the reaction will be apparent to one of ordinary skill in the art. For example, extraction and distillation methods can be employed. FIG. 8 illustrates an exemplary product recovery process. Substrate loading (the amount of substrate to solvent in a reaction) can vary dependent upon the substrate and reactor in which the reaction is carried out. In specific embodiments, where the substrate is glucose or an oligomer thereof, substrate loading can range up to 20 wt %, including 5-15 wt %. In specific embodiments, where the substrate is cellulose or lignocellulosic biomass, substrate loading can range up to 10 wt %, including 2-6 wt %. Various other reaction parameters can be optimized without undue experimentation in view of the disclosures herein and what is known in the art.

Addition of a selected amount of water to the reaction mixture was found in some cases to enhance reaction. In determining the amount of water to be added, water present in the substrate, in any hydrated reagents and in solvents, should be considered. In specific embodiments, the total water present in the reaction ranges from 1-25 molar equivalents with respect to substrate or monomer content of substrate. More specifically, improved yield has been observed in certain cases where 1-6, 6 or more, 6-12 or 12 or more equivalents of water with respect to glucose are present. It is noted that it might be expected that increased water concentrations would inhibit dehydration reactions, however, the presence of selected amounts of water increases the yield of HMF and furfural.

Figure 7:
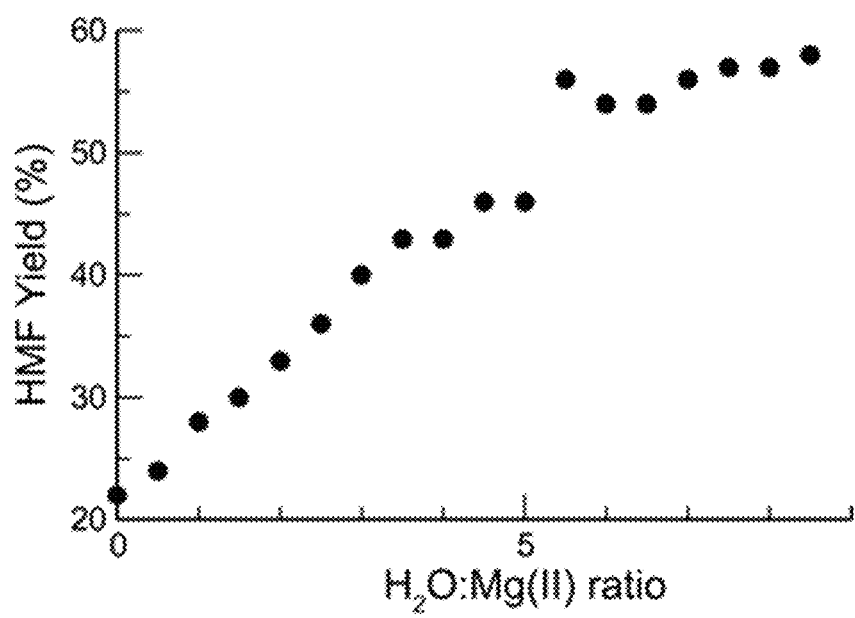
FIG. 7 is a graph illustrating HMF yield from glucose employing 2-carboxyphenylboronic acid at 1 equiv. and $MgCl_2$ at 2 equiv. with respect to glucose as a function of as a function of addition of water. The dependence of HMF yield on the ratio of $H_2O$ to Mg(II) is shown.

FIG. 7 is a graph showing the dependence of HMF yield from glucose on the molar ratio of $H_2O$ to Mg[II]. Yield increases as this ration increases, but begins to level off when the ratio is high than 6. In specific embodiments when salt and water are added to the reaction, the molar ratio of $H_2O$ to Mg or Ca can range from 0.5 to 10, more preferably is 1-10, and yet more preferably is 5-10. In specific embodiments, the molar ratio of $H_2O$ to Mg or Ca is 3 or higher, 5 or higher or 6 or higher. Without wishing to be bound by any particular mechanism of action, it is currently considered that addition of water moderates the reactivity of Mg or Ca and decreases the production of undesired side products which decrease the yield of furan.

In another aspect the invention provides a method for making fructose from glucose, glucose oligomers or a mixture thereof which comprises heating these carbohydrates in the presence of certain 2-substituted phenylboronic acids and magnesium oxide in a dipolar aprotic solvent other than an ionic liquid, an ionic liquid or a mixture thereof to form a reaction mixture. In a preferred embodiment, glucose is converted to fructose. In specific embodiments, MgO is added at a level ranging from 50 to 500 mol % and more specifically from 100 to 300 mol % with respect to glucose present in the substrate. No water needs to be added to the reaction. In specific embodiments, the reaction mixture is heated to 100-150° C. or more specifically to 105 to 130° C.

In specific embodiments, the phenylboronic acid is present in the reaction at levels ranging from 10 mol % to 300 mol % or more preferably at levels from 60 mol % to 100 mol % with respect to substrate. In specific embodiments, salt is present in the reaction at levels ranging from 50 mol % to 1000 mol %, or more preferably at levels from 150 mol % to 500 mol %, and yet more preferably at levels from 150 to 300 mol % with respect to substrate. In specific embodiments, the salt is present in the reaction at levels ranging from 50 mol % to 1000 mol % with respect to substrate. Where the substrate is a monosaccharide, mol % is measured with respect to the substrate itself. Where the substrate is an oligo- or polysaccharide (e.g., cellulose), mol % is measured with respect to monomer in the oligomer or polysaccharide. Where the substrate is biomass, mol % is measured with respect to monomer in the cellulose or hemicellulose present in biomass.

In specific embodiments, the phenylboronic acid is immobilized on a solid surface and the surface carrying the phenylboronic acid is contacted with the reaction mixture (carbohydrate/biomass, with optional salt with optional acid in polar aprotic solvent/ionic liquid).

The solid surface can be that of any material that is compatible with the chemistry of the reactions herein. The surface and the linker from the surface to the phenylboronic acid should be stable to the conditions of the reactions herein, for example, the phenylboronic acid should substantially remain immobilized, e.g., covalently attached, to the surface during the course of the reaction. Surfaces that can be used in this invention include, but are not limited to glass (including glass slides), quartz (including optical fibers), various metal surfaces such as gold, including gold with thiol monolayers, colloidal gold, semiconductors, diamond, silicon, plastic, ceramics, alum, hydroxyapatite, polyacrylamide, polyimines, polypropylene, latex, rubber, agarose, chitin, chitosan, dextran and derivatized dextrans, cellulose and derivatized cellulose (e.g., nitrocellulose, cellulose acetate), nylon, polyvinyl chloride, and polystyrene (resins, etc.), artificial bone material. Surfaces can be multilayered, e.g., glass surfaces with deposited metal surfaces, e.g., deposited gold, with optional polymer coatings (e.g., carboxymethylated dextran) as exemplified by BIACORE® sensor chips (Trademark, Biacore AB). Surfaces can be flat or curved and can be a film, a plate, a fiber, plate wells, a wafer, a grid, a mesh, a membrane, beads or pins. Surfaces can be rigid or pliable, or the surface of a gel. Surfaces may further be composed of a plurality of solid particles, micro spheres, resins or beads.

A variety of commercially available resins and other substrates carry reactive groups, directly bonded or indirectly bonded (via a linker) to the substrate, which function for immobilizing (bonding) chemical or biological molecules to surfaces (e.g., see on-line Sigma-Aldrich catalogue (www.sigmaaldrich.com/chemistry/chemistry-products.html-?Table Page=16277489; September 2011), on-line Rapp Polymere product catalogue (www.rapp-polymere.com, under resins; September 2011) and on-line EMD4 Biosciences catalogue (www.emdchemicals.com/life-science-research/peptide-and-organic-synthesis, resins for solid phase peptide and organic synthesis; September 2011). Of particular interest are resins and substrates which carry amino groups (aminobutyl, aminoethyl or aminomethyl groups), carboxyl groups, hydroxyl groups, hydrazine or hydrazide groups, amide groups, N-hydroxysuccinimidyl ester groups or other activated ester groups. Resins carrying reactive groups useful for immobilization of phenylboronates include, among others, Wang resins, TentaGel™ resins, PEG resins, polystyrene resins, Stratospheres™, Jandajel™ resins and Novabiochem® resins (e.g., Amino PEGA resin, NovaPEG amino resin, Nova Syn® TG amino resin, Nova Syn® TG carboxy resin, Carboxypolystyrene HL resin).

Figures 1, 5:
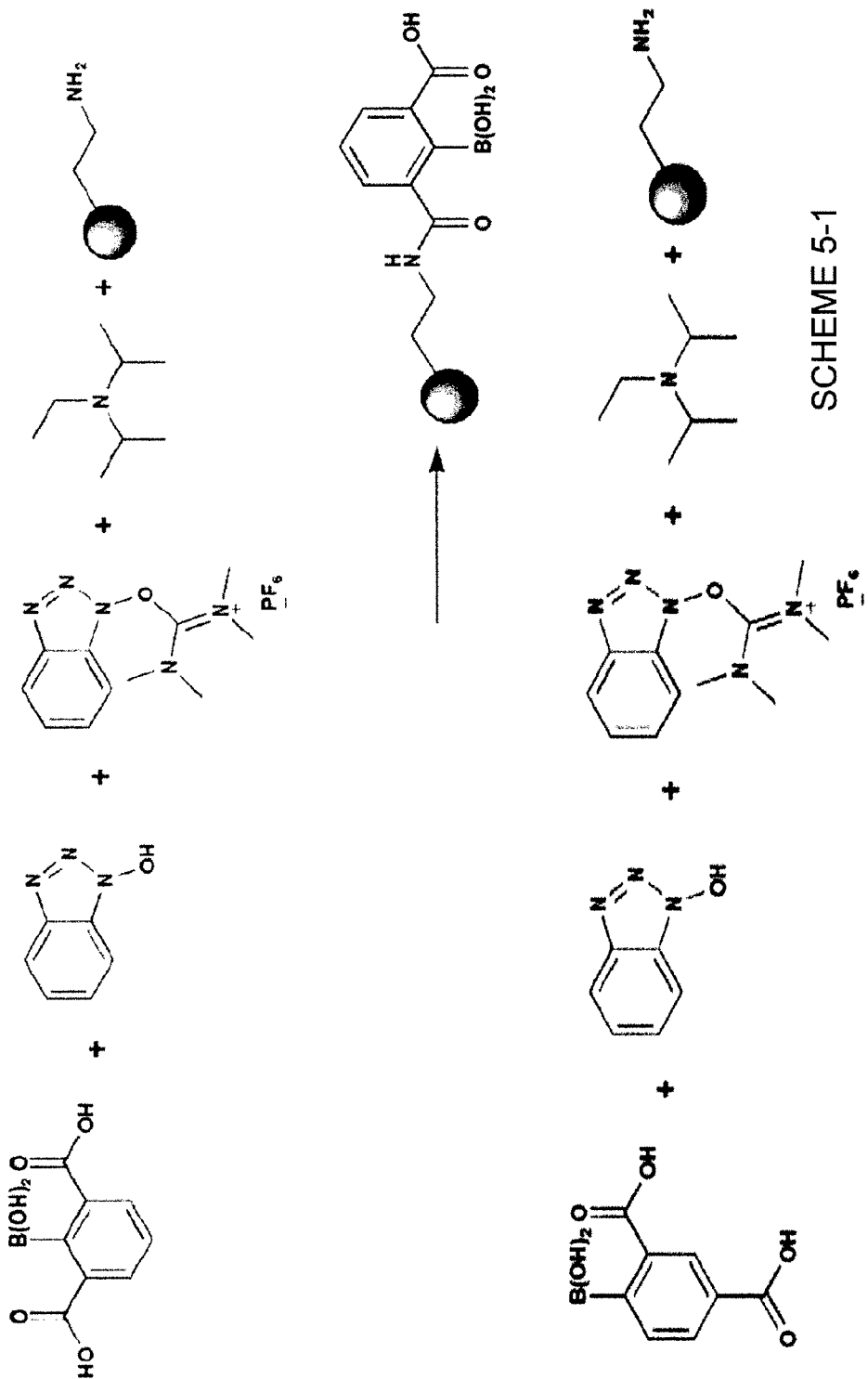
Figures 2, 5:
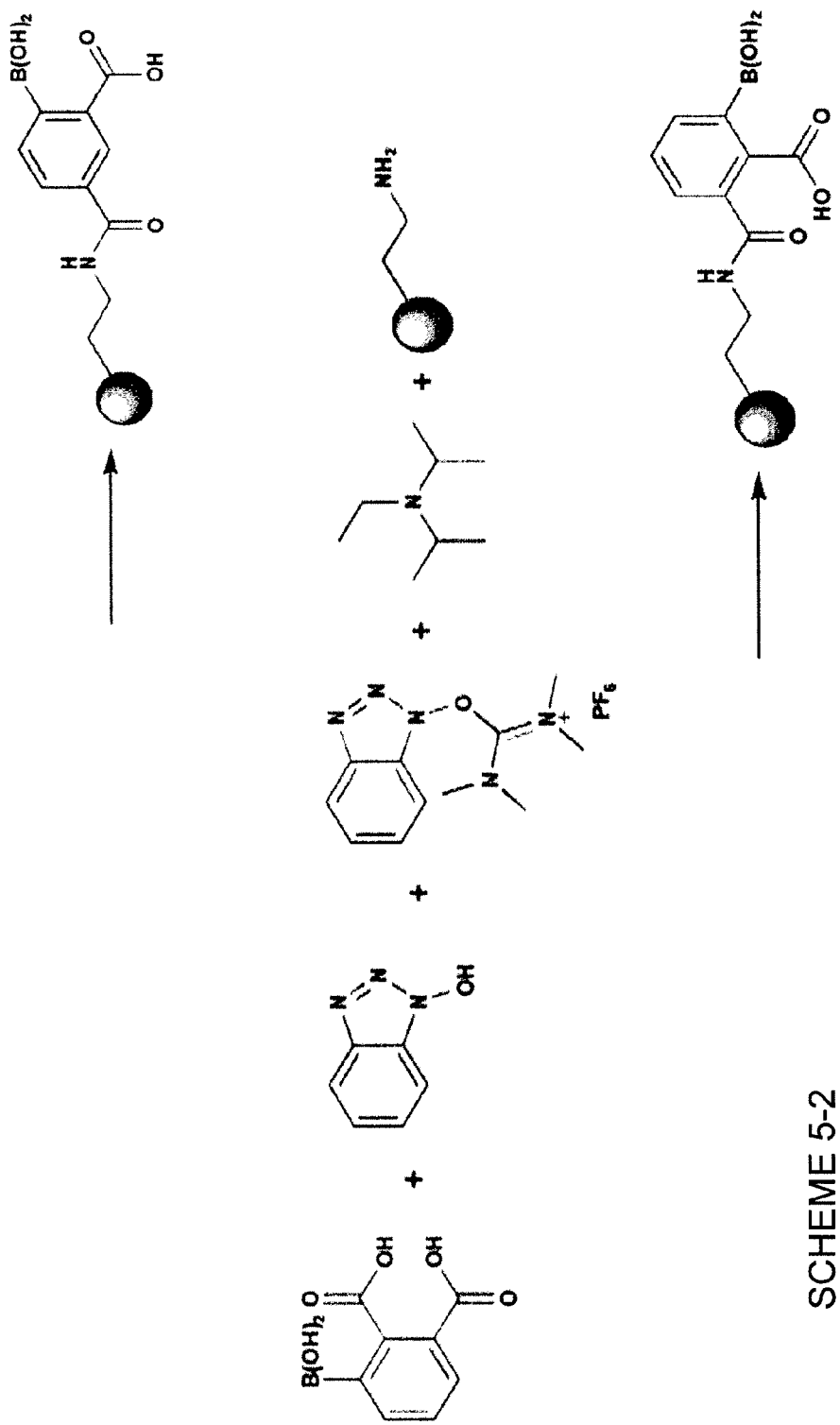
Figure 6:
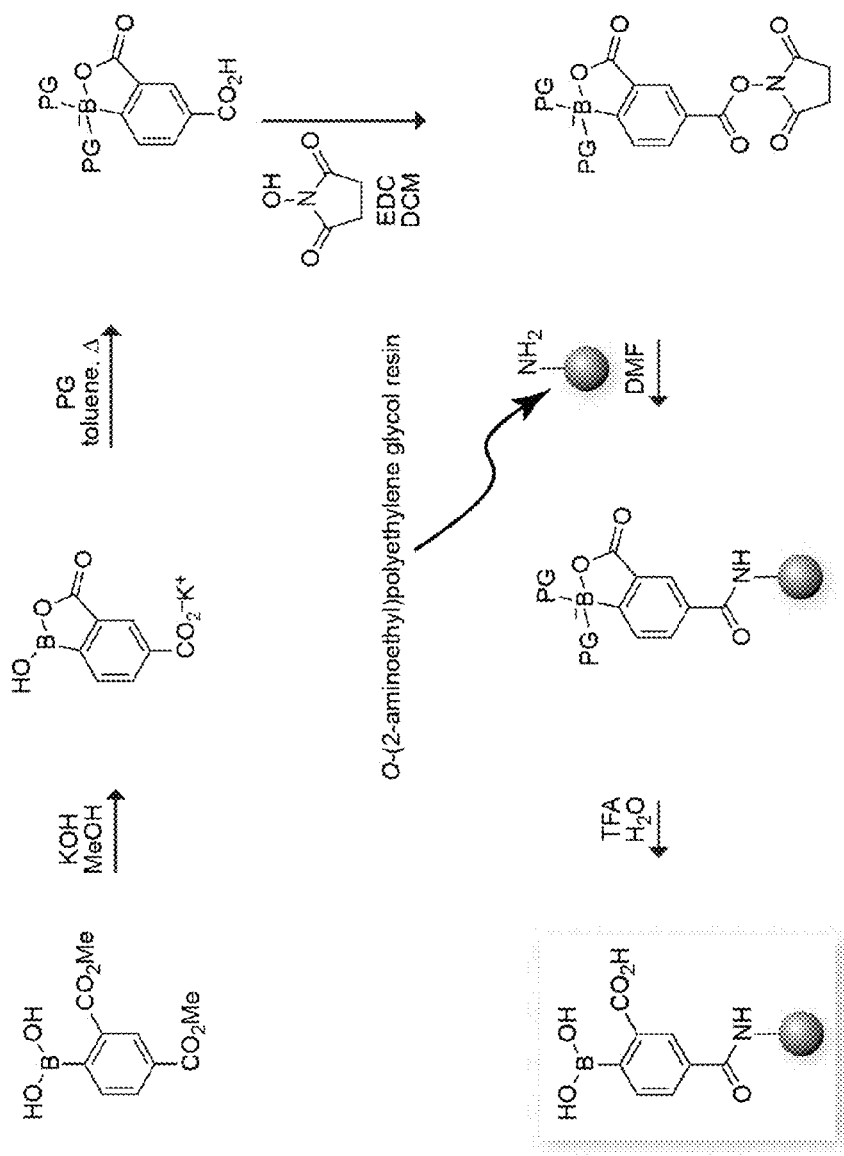
FIG. 6 provides Scheme 6 which illustrates an alternative method for immobilization of 2-substituted phenylboronic acids. This scheme schematically illustrates protection of the phenylboronic acid in the form of a protected oxaborole and formation of an exemplary activated ester of the protected oxaborole. The activated ester is then reacted with a surface-bound amine group to immobilize the oxaborole which can be deprotected when desired.

A wide variety of methods for immobilization of molecules to surfaces are known in the art. Exemplary methods of immobilization that are useful for immobilization of phenylboronates include those described in Yu et al. 1994; Cannizzoa et al. 2005; Arimoria et al. 2000. Exemplary methods for immobilization of phenylboronic acids are illustrated in FIGS. 5 and 6. In general any linking chemistry which is compatible with phenylboronates and the reaction conditions used in the processes of this invention can be employed. In specific embodiments, phenylboronic acids are immobilized onto a surface via a linker. In one alternative, the surface is derivatized to carry chemically reactive groups which may be spaced from the surface by linker moieties to which the reactive groups are covalently bonded. These surface bound reactive groups react with a chemically compatible reactive group of the phenylboronate to form a covalent bond. The phenylboronate is attached to the surface such that it remains active for promoting the reactions herein. As noted above, attachment of the phenylboronate to the surface is preferably via a reactive group substituent on the phenyl ring other than the 2-position. In a specific embodiment, attachment of the phenylboronate to the surface is preferably via a reactive group substituent on the 3- or 4-position of the phenyl ring. In a more specific embodiment, the reactive group can be an activated ester group, such as an N-hydroxysuccinimide ester group.

In another alternative, a reactive group is substituted onto the phenylboronate via an intermediate linker moiety. A reactive group suitable for reacting with a surface or a derivatized surface (e.g., a derivatized resin, including, e.g., a Wang resin) is generated on the linker moiety such that the reactive group is spaced from the phenylboronate by the linker moiety. In a specific embodiment, the reactive group and intermediate linker are attached to the para-position of the phenyl ring of the phenylboronate.

A linker moiety from a surface to the phenylboronate can be schematically illustrated as: S-(M1)-L1-M2-L2-M3-L3-M4-PB, where S is the surface, PB is the phenylboronate, L1 and L2 and L3 are optional linker moieties and M1, M2, M3, and M4 are optional bonds formed from reaction of reactive groups. At least one of L1-L3 and one of M1-M4 are present. Any linear or branched linker moiety can be employed. In specific embodiments, various supports with M1, L1, M2 and/or L2 in place or with reactive groups to form M1, M2 or M3 are commercially available which can be used for immobilization of phenylboronates which can be provided with one or more appropriate linkers (e.g., L2 and/or L3) or reactive groups to form M3/M4. In specific embodiments, linker moieties can be from 4-100 bonds in length or more specifically 6-20 bonds in length. In a specific embodiment, linker moieties can be described as an alkylene linker —(CH$_2$—CH$_2$)$_n$—, where one or more CH$_2$ moieties can be replaced with —O—, —S—, —S—S—, —NH—, —CO—, —CONH—, —CO$_2$—, —NHCO—, —CH=CH—, —NHN=CH—, —C≡C—, -cyc-alkylene (e.g., -cyclohexylene-(-cyc-C$_6$H$_{10}$—), -cyclopentylene-(-cyc-C$_5$H$_8$—), -arylene- or -heteroarylene- (e.g., -phenylene-, -naphthylene-, -pyridinylene-) and where n is 1-50, 1-25, 1-20, or 3 to 6. In specific embodiments, arylene linkers such as 1,4-arylene linkers can be employed, optionally in combination with alkylene linkers. In specific embodiments, linkers include 1,4-phenylene or 1,4'-biphenylene groups.

More specifically, phenylboronates can be linked to surfaces via polyethylene glycol (PEG) linkers. Additionally, phenylboronates can be linked to surfaces via —Y1-(CH$_2$)$_m$—Y2 moieties where Y1 and Y2 are independently selected from —O—, —S—, —O—CO—, —OC—O—, —CO—, —NR$_{15}$—, —N—CO—, or —CO—N—, where R$_{15}$ is hydrogen and alkyl or an aryl group. Phenylboronates can be substituted with reactive groups suitable for reaction with linkers for attachment to surfaces. Such reactive groups include vinyl groups, esters, active esters, N-hydroxysuccinimide esters, amides, amines, azides, hydrazines, alcohols, aldehydes, amines, amides, and alkyl halide groups, among others. Analogously, surfaces can be derivatized or substituted with reactive groups, such as those listed above, for reactions with linkers covalently attached to phenylboronates or for reaction with groups on the phenylboronates. In general any chemical linkage system known in the art for attaching a chemical or biochemical species to a surface and that is compatible with the application of the phenylboronates in reactions of this invention can be used to attached phenylboronates of this invention to a surface.

Substituted phenylboronic acids useful in the process of this invention are described above. Useful 2-substituted phenylboronic acids are commercially available, or can be prepared in view of the descriptions herein and what is known to one of ordinary skill in the art from readily available starting materials by methods that are well known in the art or by routine adaptation of such well-known methods. Synthesis of useful phenylboronic acids are described, for example, in: B. Tao, S. C. Goel, J. Singh and D. W. Boykin (2002). A practical preparation of 2-carboxyphenylboronic acid and its application for the preparation of biaryl-2-carboxylic acids using Suzuki coupling reactions Synthesis, 8:1043-1046; and D. G. Hall (2005) "Structure, Properties, and Preparation of Boronic Acid Derivatives" in *Boronic Acids: Preparation and Application in Organic Synthesis and Medicine*, Chapter 1, pages 1-99 (ed. D. G. Hall) John Wiley and Sons. Each of these references is incorporated by reference herein in its entirety for methods of synthesis of phenylboronic acids which are useful in the methods of this invention. Phenylboronic acids carrying various electron-withdrawing and electron-donating groups are reported in Mulla et al., 2004; Springsteen & Wang, 2002 and Berube et al. 2008).

2-carboxy and 2-alkoxycarbonylphenylboronic acids can also be prepared from corresponding oxaboroles by methods that are well-known in the art. Oxaboroles are commercially available or can be prepared by methods that are well-known in the art. Methods for preparation of various ring substituted oxaboroles are provided, for example, in U.S. Pat. Nos. 5,880,198; 7,582,621; 7,767,657 and 7,816,344. Each of these references is incorporated by reference herein in its entirety for descriptions of methods for making ring-substituted oxaboroles. As illustrated in FIG. 6 substituted phenyloxaboroles can be employed for immobilization of substituted phenylboronic acids.

Phenylboronic acids can be in the form of hydrates, particularly monohydrates, which can be prepared, for example by recrystallization methods that are known in the art. Certain phenylboronic acid hydrates are commercially available. The hydrate form of certain phenylboronic acids may exhibit enhanced shelf-life.

The term "alkyl" refers to a monoradical of a branched or unbranched (straight-chain or linear) saturated hydrocarbon and to cycloalkyl groups having one or more rings. Unless otherwise indicated alkyl groups have 1 to 22 carbon atoms, 1-12 carbon atoms or 1-6 carbon atoms. Alkyl groups include methyl, ethyl, propyl, butyl, pentyl and hexyl groups, including all isomers thereof. Alkyl groups can be straight-chain, branched or cyclic. The term "cycloalkyl" refers to cyclic alkyl groups having 3 to 22 and 3-6 carbon atoms having a single cyclic ring or multiple condensed rings. Cycloalkyl groups include, by way of example, single ring structures such as cyclopropyl, cyclobutyl, cyclopentyl, cyclohexyl, cyclooctyl, and the like, or multiple ring structures such as adamantanyl, and the like. Unless otherwise indicated alkyl groups including cycloalkyl groups are optionally substituted as defined herein. The term "aralkyl" refers to an alkyl group substituted with an aryl group (i.e., arylated alkyl), exemplary aralkyl groups are optionally substituted benzyl groups.

Carboxyalkyl group refers to an alkyl group substituted with a —CO$_2$H or —CO$_2^-$ moiety, such as —(CH$_2$)$_n$—CO$_2$H, where n is 1-6 or 1-3. Carboxy moieties may be in the form of carboxylate salts with various cations.

Alkoxycarbonylalkyl group refers to an alkyl group substituted with a —CO—O—R', where R' is alkyl, such as —(CH$_2$)$_n$—CO—O—(CH$_2$)$_m$—H, where n and m are independently integers from 1-6 or 1-3.

Aminoalkyl group refers to an alkyl group substituted with one or more —NH$_2$ groups, preferably one —NH$_2$ group, such as —(CH$_2$)$_n$—NH$_2$, where n is 1-6 or 1-3.

Alkylaminoalkyl group refers to an alkyl group substituted with one or more —N(R')$_2$, preferably one —N(R')$_2$, where each R' is independently an alkyl, such as —(CH$_2$)$_n$—N(R')$_2$, where n is 1-6 or 1-3 and each R' is independently a C$_1$-C$_3$ alkyl group. Amino and alkyl amino groups may be protonated and be in the form of an ammonium salt with various anions.

The term alkoxy refers to the group —OR where R is an alkyl group as defined above. In specific embodiments, alkoxy groups have 1-6 carbons atoms or 1-3 carbon atoms.

The term alkoxycarbonyl refers to a —CO$_2$R group where R is an alkyl group where in specific embodiments, R is an alkyl group having 1-6 or 1-3 carbon atoms.

The term "aryl" refers to a monoradical containing at least one aromatic ring. The radical is formally derived by removing a H from a ring carbon. Aryl groups contain one or more rings at least one of which is aromatic. Rings of aryl groups may be linked by a single bond or a linker group or may be fused. Exemplary aryl groups include phenyl, biphenyl and naphthyl groups.

Aryl groups include those having from 6 to 30 carbon atoms and those containing 6-12 carbon atoms. Unless otherwise noted aryl groups are optionally substituted as described herein.

Aryl groups include optionally substituted phenyl groups.

The term "activated ester" refers to an ester group —CO—OY where —OY is a good leaving group. A good leaving group typically is an organic group which can stabilize a negative charge including aliphatic and aryl groups substituted with at least one electron withdrawing group. In specific embodiments, activated esters react with amines to form amides. Useful —OY groups for activated esters include, among others:

—O-aryl groups, particularly those substituted with one or more electron withdrawing groups, e.g., halide, nitro group, cyano group, or trifluoromethyl group, and more particularly —O-phenyl groups substituted with one or more electron withdrawing groups; or N-oxy heterocycles, including N-oxysuccinimdyl, N-oxyphthalimide, or 1-oxybenzotriazolyl:

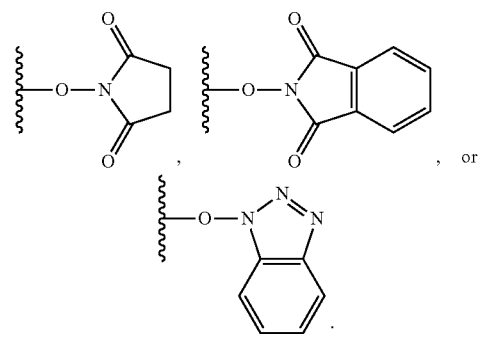

Unless otherwise specified optional substitution means substitution by one or more non-hydrogen substituents selected from halogen, hydroxyl, amine, cyano, azide, nitro, isocyanate, isothiocyanate, C1-C6 alkyl, C1-C3 alkyl, C1-C6 haloalkyl, C1-C3 haloalkyl, phenyl, benzyl, sulfate, phosphate, phosphonate, carboxyl, sulfonyl, sulfonamide, and amide. All alkyl, aralkyl, or aryl groups herein are optionally substituted with one or more non-hydrogen substituents unless otherwise specified. Substitution may be on one or more carbons or, if feasible, on one or more heteroatoms, e.g., a nitrogen. The number of substituents on such groups depends generally upon the nature of the group, but includes substitution with one, two, three, four, five or six substituents.

As to any of the groups herein which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The compounds of this invention may contain one or more chiral centers. Accordingly, this invention is intended to include racemic mixtures, diasteromers, enantiomers and mixture enriched in one or more stereoisomer. The scope of the invention as described and claimed encompasses the racemic forms of the compounds as well as the individual enantiomers and non-racemic mixtures thereof.

The compounds used in the methods of the present invention may form salts which are also within the scope of this invention. Reference to a compound of the formulas herein is understood to include reference to salts thereof, unless otherwise indicated. The term "salt(s)", as employed herein, denotes acidic and/or basic salts formed with inorganic and/or organic acids and bases. In addition, when a compound of a formula herein contains both a basic moiety, such as, but not limited to an amine and an acidic moiety, such as, but not limited to, a carboxylic acid, zwitterions ("inner salts") may be formed and are included within the term "salt(s)" as used herein. Salts should be compatible with reaction conditions used in the methods herein. Salts of compounds herein may be formed, for example, by reacting the compound with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds useful in the methods herein and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, such compounds may have trans and cis isomers and may contain one or more chiral centers, therefore exist in enantiomeric and diastereomeric forms. The invention includes use of all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The compounds useful herein may be in the free or hydrate form.

Unless otherwise stated chemical terminology as used herein is intended to have its broadest art-recognized meaning that is not inconsistent with the disclosure herein.

Dipolar aprotic solvents other than ionic liquids, certain ionic liquids and mixtures thereof, particularly miscible mixtures thereof, can be employed as solvents herein for carbohydrates and biomass and for the conversion of such materials to one or more furans. Lignocellulosic materials need not be soluble in these solvents. Such materials may be decrystalized, swollen, partially solubilized or structurally disrupted by contact with the solvents herein.

The term dipolar aprotic solvent is used to refer to solvents other than ionic liquids which have a dielectric constant of greater than about 15, a sizeable permanent dipole moment and that cannot donate suitably labile hydrogen atoms to form strong hydrogen bonds [See: "GLOSSARY OF TERMS USED IN PHYSICAL ORGANIC CHEMISTRY", IUPAC Recommendations 1994, P. Müller, Pure Appl. Chem., 66, 1077-1184 (1994)]. Dipolar aprotic solvents are also commonly called polar aprotic solvents in the art. Dipolar aprotic solvents which are not ionic liquids, include among others N,N-dialkylacetamides, N,N-dialkylformamides, 2-pyrrolidones or 3-pyrrolidones (including alkyl- or N-alkyl-substituted pyrrolidinones), pyrrolidine carboxaldehydes, dialkylsulfones, including cyclic sulfolanes, including alkyl or dialkyl sulfolanes, dialkyl sulfoxides, an alkyl or N-alkyl substituted lactam, or a dialkyl propionamide, wherein alkyl groups are preferably those having 1-6 carbon atoms or those having 1-3 carbon atoms and wherein the alkyl groups may be straight-chain, branched or cyclic. Useful solvents include among others, N,N-dimethylacetamide (DMA), N,N-diethylacetamide (DEA), dimethylformamide (DMF), N-methylpyrrolidone, 1-ethyl-2-pyrrolidinone, methylsulfonylmethane, sulfolane, 3-methylsulfolane, 2,4-dimethylsulfolane, dimethylsulfoxide, diethylsulfoxide, N-methylcaprolactam, N,N-dimethylpropionamide, 1-pyrrolidine carboxaldehyde; or miscible mixtures thereof. Preferred solvents include DMA and N-methylpyrrolidone. Additional polar aprotic solvents include acetone, and other ketones, nitroalkanes, such as nitromethane and nitroethane, hexamethylphosphoramide, and hexamethylphosphorous triamide. Acetone and other ketones are less preferred for use in this reaction because of potential formation of ketals (from ketones) with sugar hydroxyl groups. Nitroalkanes are less preferred for use in this reaction because of potential side reactions with saccharides or furan products.

In specific embodiments, reactions of this invention are conducted using ionic liquid or mixtures of ionic liquid with a polar aprotic solvent other than an ionic liquid. An ionic liquid is a salt that melts near or below ambient room temperature. For use in the methods herein the ionic liquid is liquid at the reaction temperature. In specific embodiments, the ionic liquid is one in which cellulose is soluble to some measurable extent. Preferably the ionic liquid is one in which up to about 5-25 weight % or more cellulose is soluble. More preferably the ionic liquid is one in which up to about 25 weight % or more cellulose is soluble. A number of ionic liquids have been shown in the art to dissolve cellulose.

In specific embodiments, the cation of the ionic liquid is an organic cation, particularly a cation containing at least one positively charged nitrogen atom. In specific embodiments, the ionic liquid is an alkylimidazolium ionic liquid, more particularly an alkylimidazolium halide or an alkylimidazolium acetate, and yet more particularly an alkylimidazolium chloride ionic liquid. In additional specific embodiments, the ionic liquid is a 1,3-dialkylimidazolium chloride, a 1,3-dialkylimidazolium acetate, a 1,2,3-trialkylimidazolium chloride or a 1,2,3-trialkylimidazolium acetate. In more specific embodiments, the ionic liquid is [EMIM]Cl (1-ethyl-3-methylimidazolium chloride), [BMIM]Cl (1-butyl-3-methyl-imidazolium chloride), or 1-ethyl-2,3-dimethylimidazolium chloride, or a mixture thereof. In more specific embodiments, the ionic liquid is 1-ethyl-3-methylimidazolium acetate), 1-butyl-3-methyl-imidazolium acetate or 1-ethyl-2,3-dimethylimidazolium acetate, or a mixture thereof. In specific embodiments, the ionic liquid is an alkylpyridinium ionic liquid, particularly an alkyl pyridinium halide or an alkylpyridinium acetate, and more particularly an alkylpyridinium chloride ionic liquid. In additional specific embodiments, the ionic liquid is a 1-alkylpyridinium ionic liquid, a 1,4-dialkylpyridinium chloride or a 1,4-dialkylpyridinium acetate. In more specific embodiments, the ionic liquid is 1-ethylpyridinium acetate, 1-butyl-4-methylpyridinium acetate, or a mixture thereof. In more specific embodiments, the ionic liquid is 1-ethylpyridinium chloride, 1-butyl-4-methylpyridinium chloride, or a mixture thereof. Additional ionic liquids useful in the invention particularly those in which chloride or acetate is the anion of the salt of the ionic liquid, are provided in US 2008/0033187. Additional organic cations of ionic liquids are described in US 2009/0062524, WO2009030950, WO2009030849, US20090020112, WO2008112291, US20080227162 and WO2009024607, each of which is incorporated by reference herein for descriptions of such cations.

Ionic liquids may be characterized by either the anion or cation of the salt. For example, the term "chloride-containing ionic liquid" refers to an ionic liquid in which the anion of the salt is chloride; analogous terms may be used for ionic liquids containing other anions, such as "bromide-containing ionic liquid" or "trifluoracetate-containing ionic liquid." With respect to characterization by cation, the term "alkylimidazolium-containing ionic liquid" and similar terms reciting the cations of ionic liquids refer to an ionic liquid wherein the cation has the structure named. In specific embodiments herein, the ionic liquid is a chloride-containing ionic liquid It is believed that the acidity of ionic liquids can vary from batch to batch and as a function of the source (e.g., the manufacturer of a given commercial ionic liquid or the method of synthesis employed to prepare the ionic liquid compound). The amount of acid may vary dependent upon the methods employed to make or to purify the ionic liquid. Thus, ionic liquids that are sufficiently contaminated with acid may not require addition of acid catalyst or may require addition of lower levels of acid catalyst than are described herein. One of ordinary skill in the art will recognize that there are well-known methods for assessing acidity which can be applied to assessing the acidity of ionic liquids prior to their use in the methods of this invention. One method that is applicable is a standard acid-base titration. One of ordinary skill in the art will further recognize that methods are known in the art for decreasing acidity of an ionic liquid which can be applied if desired.

In specific embodiments, the ionic liquid is an alkylimidazolium ionic liquid, more particularly an alkylimidazolium halide ionic liquid. In other specific embodiments, the ionic liquid is an alkylimidazolium chloride ionic liquid. In more specific embodiments, the ionic liquid is [EMIM]Cl, [BMIM]Cl, [EMIM]Br, 1-ethyl-2,3-dimethylimidazolium chloride, or a mixture thereof. In specific embodiments, the ionic liquid is an alkylpyridinium ionic liquid, more particularly an alkylpyridinium halide ionic liquid. In more specific embodiments, the ionic liquid is 1-ethylpyridinium chloride, 1-butyl-4-methylpyridinium chloride, or a mixture thereof. Additional ionic liquids useful in this invention are provided in US 2008/0033187.

When mixtures of polar aprotic solvent (other than an ionic liquid) and ionic liquid are employed, the amount of ionic liquid added ranges from 5 wt % to 95 wt % or from 10 wt % to 50 wt %. In other embodiments, the amount of ionic liquid is 95 wt % or more. In other embodiments, the amount of ionic liquid is 50 wt % or less, 30 wt % or less, 25 wt % or less, 20 wt % or less, 15 wt % or less or 10 wt % or less. In other embodiments, the amount of ionic liquid is 90 wt % or less, 80 wt % or less, 75 wt % or less, or 60 wt % or less. In other embodiments, the amount of ionic liquid is 50 wt % or more, 75 wt % or more, 85 wt % or more or 90 wt % or more. It will be appreciated that is can be desirable, if possible, to employ lower levels of ionic liquids which presently are generally relatively more expensive than dipolar aprotic solvents other than ionic liquids.

In specific embodiments, an acid other than a phenylboronic acid is added to the reaction mixture to facilitate hydrolysis of polymeric carbohydrates (cellulose, xylose, etc.). The amount of acid can range from dilute acid up to 5% by weight of solvent. Dilute acid is typically employed, where added acid is less than 1% by weight of solvent in the reaction mixture. In specific embodiments, a Bronsted acid is employed. In specific embodiments, the acid is an organic acid or a mineral acid, including, among others, acetic acid, phosphoric acid, HCl, sulfuric acid, and nitric acid.

In an embodiment, the invention provides a low-temperature (<250° C.), nonenzymic route from lignocellulosic biomass to fuels. Most other chemical methods for the conversion of lignocellulosic biomass to fuels use extreme temperatures to produce pyrolysis oil or synthesis gas, incurring substantial energy costs. This low temperature chemical conversion also has inherent advantages over bioprocessing for cellulosic fuels and chemicals. Fermentation of lignocellulosic feedstocks requires saccharification through extensive pretreatment, fragile enzymes, and engineered organisms. In contrast, the processes of the invention process use simple, inexpensive catalysts to transform cellulose and biomass into a valuable product in an ample yield. In addition, the present method can, for example, generate over 40% yield of HMF from cellulose and total yields of HMF and furfural of over 30% from corn stover in one step. Biomass components that cannot be converted into HMF, such as lignin, can be reformed to produce $H_2$ for HMF hydrogenolysis or burned to provide process heat (Navarro et al., 2007). Furan products can be readily isolated from the reaction mixtures herein by methods that are well-known in the art. Additionally, if desired, isolated furan products can be further purified by methods that are well-known in the art.

In specific embodiments herein, a catalyst for producing furans from a carbohydrate substrate is provided. In an embodiment, the catalyst comprises a 2-substituted phenylboronic acid, particularly a 2-carboxy or a 2-alkoxycarbonyl phenylboronic acid. The phenylboronic acid can be in the form of a salt or a hydrate, particularly a monohydrate. In specific embodiments, the catalyst comprises a 2-substituted phenylboronic acid (1) wherein the 2-substituted phenylboronic acid is immobilized on a surface; (2) wherein the catalyst further comprises magnesium[II] or calcium[II] or (3) wherein the 2-substituted phenylboronic acid is immobilized on a surface and the catalyst further comprises magnesium[II] or calcium[II]. The magnesium[II] or calcium[II] can be in the form of a salt, particularly a halide salt. The salt may be hydrated. The catalyst may comprise water to enhance yield of furan. The catalysts may contain water such that the molar ratio of H₂O to magnesium[II] or calcium[II] or a mixture thereof is 0.5 to 10. In a specific embodiment, the 2-substituted phenylboronic acid is covalently linked to a surface, such as a resin. In specific embodiments, the catalyst is capable of transforming a carbohydrate substrate into a furan in a polar aprotic solvent other than an ionic liquid, an ionic liquid or a mixture thereof. In specific embodiments the catalyst comprises a 2-substituted phenylboronate of formula I. In specific embodiments, the catalyst comprises a phenylboronate of formula I wherein R is a hydrogen or an alkyl group having 1-3 carbon atoms. In specific embodiments, in the catalyst the molar ratio of 2-substituted phenylboronate to magnesium[II], calcium[II] or a mixture thereof is 0.5 to 5. In specific embodiments, in the catalyst the molar ratio of 2-substituted phenylboronate to magnesium[II], calcium[II] or a mixture thereof is 1 to 5.

In a specific embodiment, the catalyst consists essentially of a 2-substituted phenylboronic acid (1) wherein the 2-substituted phenylboronic acid is immobilized on a surface; (2) wherein the catalyst further comprises magnesium[II] or calcium[II] or both (1) and (2). In this embodiment, the 2-substituted phenylboronic acid can have formula I and more specifically can have formula I wherein R is a hydrogen or an alkyl group having 1-3 carbon atoms.

Catalysts of this invention can be employed to produce furans, particularly HMF and furfural, from carbohydrates, particularly glucose and cellulose.

In an embodiment, the invention provides carbohydrate dehydration medium which comprises a catalyst of the invention as described herein in combination with a polar aprotic solvent other than an ionic liquid, an ionic liquid or a mixture thereof as described herein.

The term carbohydrate is used broadly herein to refer to substrates for reactions herein which contain saccharides, including monosaccharides, disaccharides, oligosaccharides, polysaccharides and lignocellulose. Monosaccharides include hexoses (6-carbon monosaccharides) and pentoses (5-carbon monosacchrides). Exemplary hexoses, include aldohexoses and ketohexoses, exemplified, among others, by glucose, mannose, galactose. fructose, sorbose and tagatose, particularly the naturally-occurring D-isomers thereof. Exemplary pentoses include aldopentoses and ketopentoses, exemplified, among others, by arabinose, ribose, xylose, ribulose and xylulose, particularly the naturally-occurring D-isomers thereof. Disaccharides include reducing and non-reducing saccharides, exemplary disaccharides, include among others, sucrose, lactose, cellobiose, maltose, and xylobiose.

Oligosaccharides are oligomers of monosaccharides. Herein the term oligosaccharide is used to refer to those species having 2-20 monomer repeating units and more specifically to those having 2-10 repeating units. Oligosaccharides can be hexose oligosaccharides, particularly homo-oligosaccharides where the repeating units are the same hexose, e.g., glucose oligomers. Oligosaccharides can be pentose oligosaccharides, particularly homo-oligosaccharides where the repeating units are the same pentose, e.g., xylose oligomers. Oligosaccharides may however contain mixtures of hexose and/or pentose monomers. Oligosaccharides can be derived from natural sources, for example, by application of various physical, chemical or enzymatic treatments or can be produced by fermentation or other microbial action.

Polysaccharides are in general polymers of saccharides and particularly polysaccharides found in biomass, including among others, cellulose, xylan, mannan, galactan and arabinan. To distinguish from oligomers, polysaccharides refer herein to species containing more than 20 monomer repeating units. However, polysaccharides typically contain significantly larger numbers of repeating units. Polysaccharides can be homo-polysaccharides containing the same monomer units or polysaccharides may contain more than one type of hexose and/or pentose monomer unit. Polysaccharides may contain water. Polysaccharides may be underivatized or derivatized by art-known methods. Preferably, polysaccharides are derived from natural sources without derivatization. Preferably the water content is 20% or less. The water-content of such materials can be determined and can be lowered by methods that are known in the art.

The term cellulose is used broadly herein to include cellulose from any source and includes alpha-cellulose, beta-cellulose and gamma-cellulose and mixtures thereof. Cellulose can be characterized by its degree of polymerization (DP, average number of anhydroglucose units) which can range from tens of thousands to hundreds, e.g., 10,000-12,000 to 300. Cellulose as used herein also refers to underivatized cellulose or derivatives of cellulose, such as ethyl- or methylcellulose, hydroxyalkyl cellulose (e.g., hydroxypropyl cellulose), carboxymethylcellulose, or mixtures thereof. In specific embodiments, the method of this invention is particularly useful for cellulose or cellulose derivatives which are water-insoluble. In specific embodiments, the method of this invention is particularly useful for cellulose derived without chemical modification from natural sources. Cellulose preferred for this invention contains less than 20% by weight of water and more preferably contains 15% by weight or less of water. The water-content of cellulose can be determined and lowered by methods that are known in the art.

The term lignocellulose refers to material, typically derived from biomass, composed principally of cellulose and lignin. Lignocellulose often also contains hemicellulose. Lignocellulose can be derived from biomass, including without limitation, wood or woody material, paper waste, vegetable fiber, plants, crops and agricultural residue (e.g., corn stover, wheat straw, barley straw, soya stalk, sugar cane bagasse), leaves and stalks of non-woody plants, and grasses (switch grass, Miscanthus). In specific embodiments, lignocellulose can contain 20-50% dry weight cellulose. In other embodiments, lignocellulose can contain from 50 to 95% dry weight cellulose. Typically, cellulose and other biomass polymers in lignocellulose are tightly bound to lignin. Lignocellulose or lignocellulosic material may be pre-treated by physical methods (grinding, chopping or mashing) or by chemical or biological (e.g., enzymatic) methods as are known in the art which may increase the accessibility of cellulose or other biomass polysaccharide to hydrolysis. Such chemical or biological pre-treatments are however, not required for the practice of this invention. Mechanical pre-treatment involving chopping and/or grinding to a desired particle size can be applied as is known in the art. Additional pretreatment processes, include among others, exposure to steam, hot water, dilute acid, AFEX, ARP and exposure to lime. The goal of such pretreatment is to release cellulose and hemicellulose from lignin. Mosier et al. (2005) provides a recent review of such pretreatment steps and is incorporated by reference herein in its entirety for this description. Lignocellulosic materials include, among others, wood residues, paper waste, agricultural residue and energy crops (e.g., woody grasses, such as switch grass or Miscanthus). Lignocellulose and lignocellulosic material may contain water. Preferred lignocellulose contains less than 20% by weight of water and more preferably contain 15% by weight or less of water. The water-content of such materials can be determined and can be lowered by methods that are known in the art. In a specific embodiment, the methods of the present invention are useful for generation of HMF from high-cellulose lignocellulose materials, such as newspaper, paper towels and other paper products or waste products and cotton.

HMF prepared by methods herein can be employed as a source of various derivatives which are prepared by art-known methods. As shown in Scheme 3 (FIG. 3) HMF can be converted to other useful fuels or chemicals, particularly DMF.

Figure 2:
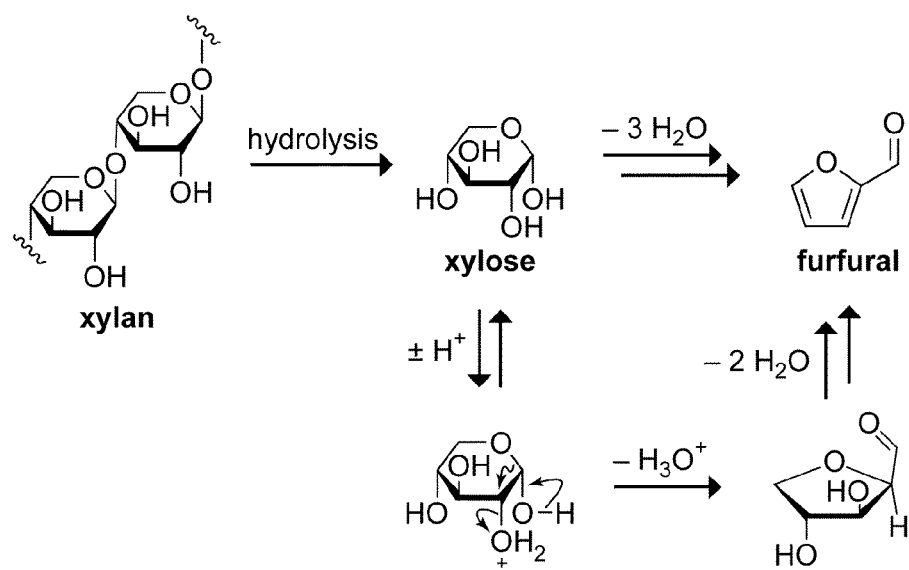
FIG. 2 provides Scheme 2 which schematically illustrates production of furfural from xylan by hydrolysis to xylose and dehydration to furfural.
Figure 3:
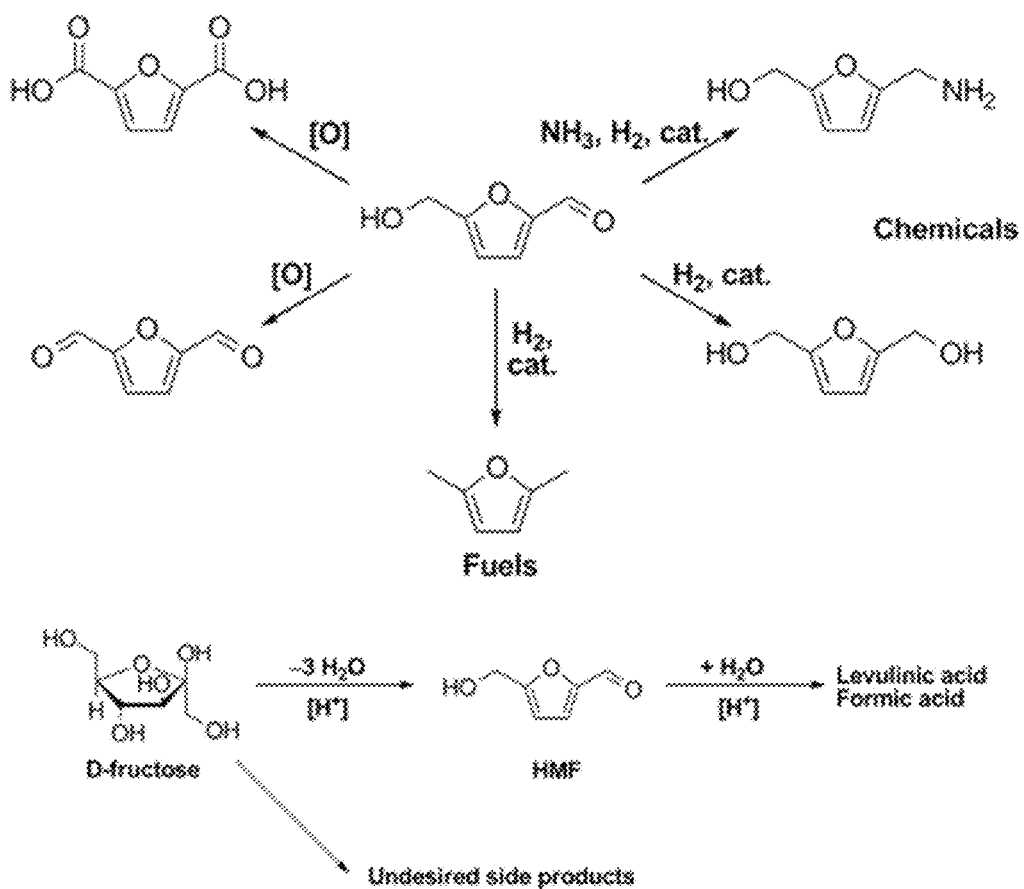
FIG. 3 provides Scheme 3 which illustrates various art-known conversions of HMF to produce fuels and commercially important chemical starting materials. The scheme also illustrates the possible production of undesired side products from fructose or HMF. Undesired side products include products of polymerization, which include insoluble materials designated humins.

The invention also provides a method of making useful fuels or chemicals in addition to HMF and furfural. Such methods comprise, as a first step, making HMF or furfural by a method of this invention from a carbohydrate or carbohydrate feedstock and thereafter converting HMF or furfural to other useful fuels or chemicals. In a specific embodiment, the invention provides a method for making DMF by conversion of HMF made by the methods of this invention. In a specific embodiment, HMF is converted to DMF via hydrogenolysis. In a more specific embodiment, hydrogenolysis of HMF to DMF is conducted employing a copper catalyst and particularly using a copper-ruthenium catalyst or a copper chromite catalyst. Specific useful catalysts include $Cu/Cr_2O_3$ with optional promoters including Ba and Cu:Ru/carbon catalysts. HMF can be converted to other useful species as is known in the art and as illustrated in FIGS. 1-3. For example, HMF can be reduced to levulinic acid or can be oxidized to 2,5-furandicarboxylic acid, by methods that are well-known in the art.

In specific embodiments, furfural made by the methods herein can be converted by art-recognized methods to useful chemical species. For example, furfural can be reduced to furfuryl alcohol which in turn is a precursor of various chemical products, including among others furan resins. Furfural can be converted to tetrahydrofuran (THF), methyltetrahydrofuran (M-THF) and tetrahydrofurfuryl alcohol (THFA). Additionally, furfural can be converted to 1,5, pentane diol (Yu et al. 2011).

In addition, HMF and furfural prepared by the methods of this invention can be employed in condensation reaction (e.g., aldol condensation reactions) to generate more complex chemical species.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomer and enantiomer (e.g., cis/trans isomers, RIS enantiomers) of the compound described individually or in any combination. Specific names of compounds are intended to be exemplary, as it is known that one of ordinary skill in the art can name the same compounds differently.

Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated. Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Herein, the term "consisting essential of" excludes materials which do not materially affect the formation of HMF and fufural from carbohydrates. The broad term comprising is intended to encompass the narrower consisting essentially of and the even narrower consisting of: Thus, in any recitation herein of a phrase "comprising one or more claim element" (e.g., "comprising A and B), the phrase is intended to encompass the narrower, for example, "consisting essentially of A and B" and "consisting of A and B." Thus, the broader word "comprising" is intended to provide specific support in each use herein for either "consisting essentially of" or "consisting of" The invention illustratively described herein suitably may be practiced in the absence of any element or elements, limitation or limitations which is not specifically disclosed herein.

One of ordinary skill in the art will appreciate that starting materials, carbohydrate feedstocks, catalysts, reagents, synthetic methods, purification methods, analytical methods, and assay methods, other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials; alternative starting materials, reagents, methods of synthesis of catalysts, purification methods, methods of analysis; methods for conversion of HMF and furfural to other products, as well as additional uses of the invention.

THE EXAMPLES

Example 1

General and Analytic Methods

General. Commercial chemicals were of reagent grade or better and were used without further purification. 1-Ethyl-3-methylimidazolium chloride (99.5%, [EMIM]Cl) was from Solvent-Innovation (Cologne, Germany). Glucose was from J. T. Baker (Phillipsburg, N.J.). Cellobiose, cellotriose, cellotetraose, and cellulose (medium cotton linters, C6288) were from Sigma Chemical (St. Louis, Mo.). The estimated water-content of cellulose employed is 0-2% by weight as determined by measuring weight loss after heating to 140° C. Milled and sieved corn stover and AFEX-treated corn stover were generously provided by B. E. Dale and co-workers (see U.S. Pat. Nos. 4,600,590 and 6,106,888 for a description of the AFEX process.) The estimated water-content of corn stover employed is 5-10% by weight of corn stove as determined by measuring weight loss after heating to 140° C. Magnesium chloride hexahydrate was from Fisher Scientific (Pittsburgh, Pa.). Boronic acids were from either Synthonix (Doylestown, Pa.) or Combi-Blocks (San Diego, Calif.). All reactions were performed in 4-mL glass vials heated in a temperature-controlled VWR Mini Shaker at 600 rpm.

The term "concentrated under reduced pressure" refers to the removal of solvents and other volatile materials with a rotary evaporator under reduced pressure provided by a Welch 2025 self-cleaning dry vacuum system while maintaining the water-bath temperature below 50° C. except where noted. The term "high vacuum" refers to a vacuum of <0.1 torr achieved by a Welch mechanical belt-drive oil pump. The term "speed vacuum" refers to spinning samples in a UVS400 Universal Vacuum System from Thermo Scientific (Waltham, Mass.) under reduced pressure provided by a Welch 2042 DryFast vacuum system.

NMR spectra were acquired with a Bruker DMX-400 Avance spectrometer ($^1$H, 400 MHz; $^{13}$C, 100.6 MHz) at the National Magnetic Resonance Facility at Madison (NMRFAM). NMR spectra were obtained at ambient temperature unless indicated otherwise. Values of the coupling constant J are given in Hertz. Mass spectrometry was performed with a Micromass LCT (electrospray ionization, ESI) in the Mass Spectrometry Facility in the Department of Chemistry.

Analytic Methods. Reaction products were analyzed by HPLC and quantitated using calibration curves generated from commercially available standards. Product concentrations were calculated from HPLC-peak integrations, which were then used to calculate molar yields. During a reaction, an aliquot of the reaction mixture was taken, diluted with a known mass of deionized water, cooled to 4° C., subjected to centrifugation at 12,000 rpm for 5 min to sediment insoluble products, and analyzed by HPLC using an Agilent 1200 system equipped with refractive index and photodiode array detectors. HMF, furfural, and fructose were analyzed by ion-exclusion chromatography with a Bio-Rad Aminex HPX-87H column (300×7.8 mm) using a 5 mM $H_2SO_4$ mobile phase at a flow rate of 0.6 mL/min at 65° C.

Example 2

Production of Furans (HMF or Furfural) from Sugars

Table 1A lists results using boron/magnesium systems to catalyze the conversion of glucose to HMF in N,N-dimethylacetamide (DMA) or the ionic liquid, 1ethyl-3-methylimidazolium chloride ([EMIM]Cl). Substrate load in these experiments was about 10% by weight with respect to solvent. Mol % and HMF yield are relative to glucose.

Phenylboronic acids having a 2-carboxylate in particular showed a significant increase in yield of HMF over that obtained with $MgCl_2.6H_2O$ alone. Table 1A also provides a comparison of the reaction in the presence of various salts other than $MgCl_2$, including halide salts of lanthanide metals (La and Ce), transition metals (Cr, Cu, Fe, Mo, and Zn), alkali metals (Li, Na, K, Cs and Rb) as well as other magnesium halides and an exemplary calcium halide. The counterion of the magnesium salt did not appear to play a major role, as hydrated $MgBr_2$ and $MgI_2$ were also effective in mediating the conversion. Calcium chloride also exhibited a significant enhancement in yield of HMF in the presence of phenylboronate. The significant enhancement of HMF yield that is observed with magnesium halides and the exemplary calcium halide is not observed with salts of other metals tested. Addition of Mg powder also did not exhibit the enhancement observed with magnesium halide.

Table 1A indicates that HMF is produced with certain substituted phenylboronates in the absence of added salt or water. For example, in DMA 4-carboxyphenyboronic acid and 3-carboxy-5-nitrophenyboronic acid promote HMF formation. For example in [EMEM]Cl, 2-nitrophenylboronic acid, 2-formylphenylboronic acid and 2-acetylphenylboronic acid promote formation of HMF.

Table 1B lists results from Table 1A and additional experiments conducted as described for Table 1A and provides a comparison of conversion of glucose to HMF in DMA employing various metal catalysts in the absence of phenylboronic acids. Note that hydrated metal halide salts of magnesium and nickel, e.g., $MgCl_2.6H_2O$ and $NiCl_2.6H_2O$ promote HMF formation from glucose in DMA. Chromium chloride also promotes good yield of HMF from glucose in DMA. Because of the possible high environmental toxicity of chromium salts, the use of salts magnesium and calcium salts is preferred.

Tables 1C and 1D list results from Table 1A and additional experiments conducted as described in Table 1A to provide a comparison of conversion of glucose to HMF in DMA employing $MgCl_2.6H_2O$ as a function of the phenylboronate employed. Note that 2-methoxycarbonylphenylboronic acid and 2-ethoxycarbonylphenylboronic acid both promote significant levels of HMF formation from glucose in the absence of added salt or water. Other substituted phenylboronic acids: 3-carboxyphenylboronic acid, and trifluormethyl-substituted phenylboronic acids are also observed to promote HMF formation from glucose in the absence of added salt or water. Additionally, 2-methoxyphenylboroic acid, 5-amino-2-hydroxymethylphenylboronic acid, 2,6-dimethylphenylboronic acid, 3-carboxy-5-nitrophenylboronic acid, 4-carboxyphenylboronic acid and 2-carboxyphenylboronic acid promote relatively low levels of HMF formation from glucose under the conditions tested.

Table 1E lists results from Table 1A and additional experiments conducted as described in Table 1A to provide a comparison of conversion of glucose to HMF in DMA employing hydrated salts. These results can be compared with those from Table 1B (see Table 1H for selected comparisons) to show enhanced formation of HMF in several combinations of the 2-substituted phenylboronic acids tested with halide salts, particularly hydrated halide salts. The enhancement is particularly noted in combinations of 2-carboxy, 2-methoxycarbonyl and 2-ethoxycarbonyl-substituted phenylboronic acids with magnesium and calcium salts, particularly magnesium and calcium hydrated salts.

Experiments were also performed (see Tables 1A and 1F) to assess the possible role of added water in the reaction by adding anhydrous $MgCl_2$ with increasing amounts of added $H_2O$. Table 1F provides a comparison of the effect of water provided as a hydrate or by addition on the conversion of glucose. In these reactions, HMF yield increased with increasing added water up to addition of about 12 equivalents of $H_2O$ (with respect to glucose). The yield levels off, but remains high, at water levels ranging up to 17 equivalents. Water can be added in hydrated salt or by addition of desired amounts of water. Note that carbohydrate substrates, particularly cellulose and lignocellulosic biomass, may contain water. Adding $H_2O$ to reactions with other metal chloride salts did not however the high yield of HMF attainable with $MgCl_2$.

Table 1G lists results from Table 1A and may include additional experiments conducted as described in Table 1A. Table 1G provides a comparison of the effect of catalyst and salt concentration on conversion of glucose to HMF.

Table 2A lists results for the conversion of certain mono- and disaccharides (other than glucose and cellobiose) to HMF and furfural. The pyranose sugars galactose and mannose and the furanose sugars sorbose and tagatose, were converted to HMF using the 2-substituted phenylboroic acid in the presence of magnesium ion and water in both a polar aprotic solvent other than an ionic liquid (e.g., DMA) and ionic liquid (e.g., [EMIM]C1.) Pentose sugars (xylose and arabinose) are converted under analogous reaction conditions to furfural. Table 2B lists results for the conversion of fructose to HMF. Yields presented in Tables 2A and B are for unoptimized reaction conditions.

Tables 2C and 2D list results for the conversion of certain ketohexoses (including fructose) and certain aldohexoses (including glucose). Yields of 50% or more of HMF are observed from conversion of psicose, fructose, sorbose, glucose, mannose, gulose, idose, and galatose. Interestingly, there is a disparity in the reactivity of the different boronic acids with ketohexoses (see Table 2C). 2-Carboxyphenylboronic acid attained its best HMF yields for all ketohexoses when it was used in conjunction with the magnesium salt. 2-Methoxycarbonylphenylboronic acid needed the salt for fructose and sorbose to achieve the best HMF yields, but did not for psicose and tagatose. Finally, 2-ethoxycarbonylphenylboronic acid accessed the highest HMF yields without the salt for all the ketohexoses. It also consistently had the highest HMF yields of the three boronic acids. Thus, the ethoxycarbonyl moiety conveys the highest level of reactivity to transform the ketohexoses to HMF.

The variance of the conditions required to achieve the best HMF yields suggests differing levels of dehydration activity for the three boronic acids. The 2-ethoxycarbonylphenylboronic acid has the highest dehydration capacity of the three, followed by 2-methoxycarbonylphenylboronic acid and then 2-carboxyphenylboronic acid. It is also of interest that the yields varied for the different ketohexoses, with fructose typically giving the highest HMF yields, followed by sorbose, psicose, and tagatose. It is possible that these differences are a result of the differing isomeric equilibria of the sugars. According to previous studies, fructose predominately exists in a furanose form in an organic medium, as does psicose. (Binder, J. B.; Cefali, A. V.; Blank, J. J.; Raines, R. T. *Energy Environ. Sci.* 2010, 3, 765; Angyal, S. J. *Carbohydr. Res.* 1994, 263, 1.)

Contrarily, sorbose primarily exists in a pyranose form and tagatose exists almost entirely in a pyranose form. As the dehydration of sugars is reported to proceed through the furanose form of sugars (Antal, M. J., Jr.; Mok, W. S. L.; Richards, G. N. *Carbohydr. Res.* 1990, 199, 91), those having greater isomeric furanose conformations should give higher HMF yields.

Results with D-aldohexoses are presented in Table 2D. Interestingly, only altrose, idose, and galactose gave higher yields of HMF using boronic acids alone. This selectivity could be due to their higher ratio of furanose isomeric conformations relative to the other aldohexoses. (Angyal, S. J. *Carbohydr. Res.* 1994, 263, 1.) The other aldohexoses all required the presence of $MgCl_2.6H_2O$ to access higher HMF yields. This result suggests that the magnesium is involved in tautomerizing the pyranose conformations of sugars to their furanose forms. Once there, the boronic acids catalyze the dehydration to HMF. Sugars that are better able to access their furanose conformations appear to be converted to HMF in higher yields than those that exist primarily in their pyranose forms. It is possible that the α-anomer of the pyranose structure is the easiest path to isomerize to the furanose form because glucose and mannose have high ratios of the α-anomer and gave the highest HMF yields. Yet, gulose also gave high HMF yields and exists primarily in the β-anomer of its pyranose form, at least in DMSO.[19] The choice of organic solvent could alter the isomerization equilibria of the anomeric forms, as could the presence of a magnesium ion. (Binder, J. B.; Cefali, A. V.; Blank, J. J.; Raines, R. T. *Energy Environ. Sci.* 2010, 3, 765. Tajmir-Riahi, H.-A. *Carbohydr. Res.* 1988, 183, 35.)

The methods of the invention can be employed to dehydrate to HMF D-hexose sugars that exist predominantly in either a furanose or pyranose isomeric conformation. Certain phenylboronic acids alone can readily promote dehydration of D-hexoses that exist predominantly in the furanose form. The apparent need for the presence of magnesium catalyst for conversion of D-hexoses that exist predominantly in the pyranose form, suggest that the added salt (magnesium or calcium salt) facilitates isomerization of the pyranose forms to their furanose forms before dehydration to HMF.

Tables 3A and 3B list results for the production of HMF from cellobiose and other glucose oligomers. The results observed are somewhat different than those observed for production of HMF from glucose. HMF was produced on reaction of cellobiose with 2-carboxy-substituted phenylboronic acids in the presence of magnesium halide and water in both polar aprotic solvent and ionic liquid. Surprisingly, cellobiose reacted with 2-carboxyester substituted phenylboronic acids in DMA to generate high yields of HMF (~40-50%) without addition of magnesium halide or water. HMF formation was observed with cellobiose, cellotriose, cellotetraose, maltose, sucrose and inulin.

Acid catalysis is often necessary to hydrolyze cellulosic materials to access the monomeric glucose before conversion to HMF can occur. It is thus surprising that higher yields of HMF were obtained using the 2-methoxycarbonyl- and 2-ethoxycarbonylphenylboronic acids alone than in tandem with $MgCl_2.6H_2O$ (Tables 3A and 3B). While the phenylboronic acids were apparently able to bind the cellobiose and facilitate hydrolysis and conversion to HMF, it seemed that coordination of the phenylboronic acid makes the conversion facile for only one monomer per saccharide, as the yields were always below 50%.

Cellotriose and cellotetraose, the tri- and tetra-polymers of glucose, respectively, were both able to be converted to HMF using only the phenylboronic acid, although it appeared again that only some of the monomers were able to be transformed. Additionally, the yields of HMF decreased with increased polymer length, and higher temperatures became necessary to achieve better HMF yields.

A mechanism for a similar type of hydrolysis had been hypothesized previously to occur through a distortion of one of the glucose units to a half-chair, making its endocyclic oxygen lone pair synperiplanar to the other glucose unit. (Anslyn, E. V.; Dougherty, D. A. *Modern Physical Organic Chemistry*; University Science Books: California, 2006.) In this proposed mechanism, the second glucose unit serves as a leaving group. Without wishing to be bound by any particular reaction mechanism, in the present system, the phenylboronic acid could distort a glucose unit to a half-chair to facilitate hydrolysis between two units, and then serve to dehydrate the distorted glucose unit to HMF.

The hydrolysis activity of the boronic acids was explored further with maltose, the α(1→4) dimer of glucose. Only small yields of HMF were attained, and those required the presence of $MgCl_2.6H_2O$. It appears that the ability of the phenylboronic acids to mediate hydrolysis is limited by the anomeric form of the glycosidic bond between two glucose monomers. The hydrolysis of sucrose, a dimer of fructose and glucose, was achieved with comparable HMF yields to cellobiose. Finally, inulin, a polymer of fructose, was able to be converted to HMF, though the yields were decreased somewhat and $MgCl_2.6H_2O$ was necessary for two of the boronic acids. This result is consistent with those observed for cellotriose and cellotetraose, as the increased chain length required higher temperatures to access higher yields. Whereas fructose is converted to HMF more easily than glucose, the length of the polymeric chain might hinder phenylboronic acid activity.

Figure 4:
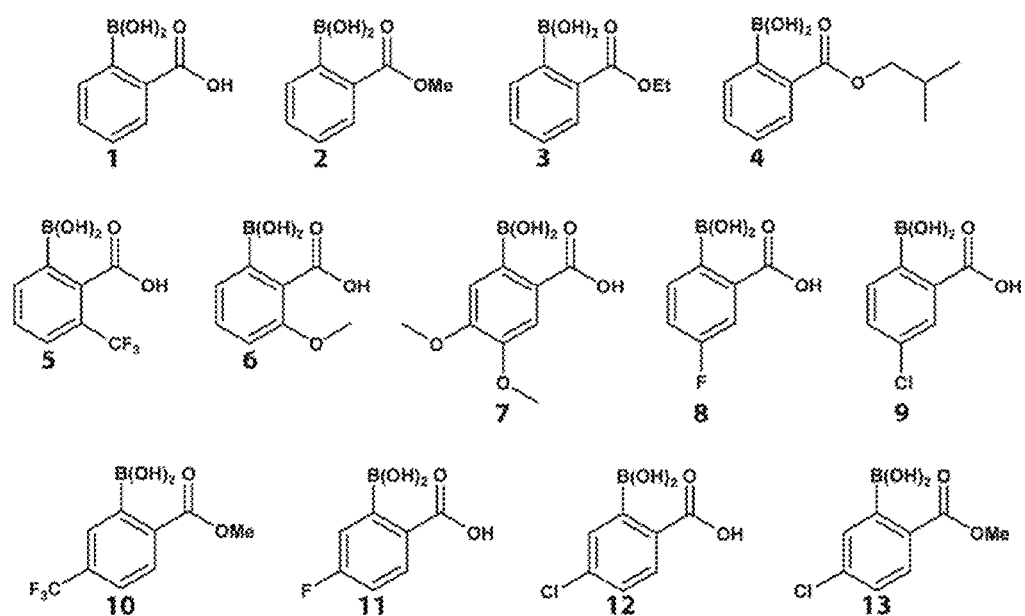
FIG. 4 provides Scheme 4 which illustrates the chemical structures of a number of exemplary 2-carboxy substituted and 2-alkoxycarbonyl substituted phenylboronic acids that are useful in the methods and compositions of the invention.

Table 4 lists results for conversion of glucose and cellobiose with additional 2-substituted phenylboronic acids. The structures of these additional phenylboronic acids are illustrated in FIG. 4. Phenylboronates having 2-carboxy and 2-methoxycarbonyl groups provide good HMF yields. Phenylboronates having 2-ethoxycarbonyl groups typically provide the highest activity in carbohydrate conversion reactions. The effect of additional or alternative substitution on activity is examined in Table 4. Activity generally increased with increasing ester carbon side chains (methyl to ethyl ester), in contrast, 2-isobutylcarboxyphenylboronic acid, exhibits a significant decrease in HMF yield, suggesting that steric bulk within the ester side chain can hinder the conversion capability of the boronic acids.

Carboxylphenylboronic acids with an additional substitution were examined to see the effect of modifying the electronics of the aryl ring and determine the influence on HMF yields. Additional substitutions such as a trifluoromethyl, methoxy, fluoro and chloro resulted in an increase in HMF yields (Table 4). The addition of a fluoro group at the 5-position, however, resulted in a drastic decrease in HMF yields. This may be due to high reactivity that caused degradation of the HMF product. In general, the addition of inductively electron-withdrawing substituents results in an enhancement in HMF yields. The increase in yields could, for example, result from an increased association of the phenylboronic acids with the sugar due to a decrease in the electron density at the boronic acid moiety.

Example Reaction for Production of HMF

Glucose (51.6 mg, 286 μmol), 2-carboxyphenylboronic acid (47.3 mg, 285 μmol) or other phenylboronic acids (as indicated) and $MgCl_2.6H_2O$ (145.5 mg, 716 μmol) were mixed in DMA (N,N-dimethylacetamide, 500 mg) or [EMIM]Cl (1 ethyl-3-methylimidazolium chloride, 500 mg). The reaction mixture was heated at a selected temperature, e.g., 120° C. for a selected time, e.g., 4 h. At 1-h intervals, aliquots of the reaction mixture were removed for HPLC analysis. Exemplary reactions involving other mono- and disaccharides (cellobiose, fructose, lactose, galactose, mannose, sorbose, tagatose, arabinose, or xylose) were performed in a similar manner, although $MgCl_2.6H_2O$ was not always used for cellobiose. Reactions with arabinose and xylose (pentoses) were also analyzed for furfural. Reactions were also performed using anhydrous $MgCl_2$ and adding $H_2O$ (1-12 equivalents with respect to mono- or disaccharide). Reactions were also performed by using anhydrous $MgCl_2$ and adding 1-12 equiv of $H_2O$. Results of water additions are also illustrated in FIG. 7 where HMF yield dependence on the $H_2O$ to Mg molar ration is shown. HMF yield generally increases with increasing water, but levels off as the $H_2O$ to Mg(II) molar ratio approaches 8-9. Experiments (data not shown) were also conducted in the presence of diaza-18-crown-6 at 1 equiv relative to Mg(II). The presence of the complexing agent was found to prevents Mg(II) from facilitating the conversion of glucose to HMF. This indicates that Mg(II) facilitates the conversion of glucose to HMF.

Example 3

Synthesis of HMF from Cellulose and Lignocellulose

Tables 5A-5D list results for the production of HMF from cellulose in ionic liquid. HMF was formed in generally good yield by reaction of cellulose in ionic liquid in the presence of the 2-carboxy-substituted phenylboronic acid, magnesium salt, water and dilute mineral or organic acid (less than 1% by weight). Highest yields of HMF (~40%) were observed in reactions in the presence of 2-carboxyesters of phenylboronic acid, magnesium halide (e.g., magnesium chloride), water (added as hydrated magnesium salt) and dilute mineral acid, e.g., $H_2SO_4$ or HCl (where "dilute" means less than 1% by weight of ionic liquid). The yield obtained from reactions employing 2-carboxyphenylboronic acid was much lower than observed with the corresponding esters, and some form of polymer appeared to be formed during these reactions. As observed with the conversion of glucose to HMF, the counterion of the magnesium salt did not play a major role in the conversion of cellulose. Substrate loading was 20-25 mg in 500 mg ionic liquid (e.g., 4-5 wt % relative to ionic liquid). Table 5C lists results for synthesis of HMF from cellulose under presently preferred conditions. Table 5D extends the experiments to cellulose substrates: cotton, paper towels and newspaper.

Table 6 lists the results for the production of furans (HMF or furfural) from lignocellulose in the presence of 2-carboxysubstituted ester phenylboronic acid, magnesium salt, water and dilute acid (less than 1% by weight) in ionic liquid. Lignocellulose was in the form of untreated corn stover or corn stover that was pretreated by ammonia fiber expansion (AFEX). An 18% yield of HMF and 15% yield of furfural were obtained from corn stover using 2-methoxycarbonylphenylboronic acid with $MgCl_2.6H_2O$ and sulfuric acid or HCl. A 14% yield of HMF and 21% yield of furfural were obtained from AFEX-pretreated corn under analogous conditions. Yields in Table 5 are for unoptimized reaction conditions. Substrate loading in these experiments ranged from 4-5 wt % with respect to ionic liquid.

Example Reaction for Production of HMF

Cellulose (21.6 mg, 133 μmol of glucose units in cellulose) and [EMIM]Cl (493.4 mg) were mixed and heated at 105° C. for 3 h. 2-Methoxycarbonylphenylboronic acid (48.4 mg, 269 μmol) (or other phenylboronic acid), $MgCl_2.6H_2O$ (125 mg, 615 μmol), and concentrated HCl (3.4 μL, 109 μmol) were added, and the reaction was heated at selected temperature for 4 h. At 1-h intervals, aliquots of the reaction mixture were removed for analysis by HPLC. Other phenylboronic acids and mineral acids were also used (as indicated). Reactions involving lignocellulose were performed in a similar manner, but were analyzed for furfural as well.

Example 4

Synthesis of Fructose from Glucose

Table 7 lists results for the conversion of glucose and cellobiose to fructose as mediated by MgO and 2-carboxyphenylboronic acid and corresponding esters. In the polar aprotic solvent, DMA, a 41% molar yield of fructose from glucose was achieved. In ionic liquid, [EMIM]Cl, a 33% yield of fructose was obtained under similar conditions. 2-substituted carboxyesters of phenylboronic acid did not exhibit any significant enhancement of fructose generation compared to the 2-carboxyphenylboronic acid. Mg metal powder and $MgSO_4$ were also used in attempted conversions, but yielded only an insignificant amount of fructose. In similar reactions, with cellulose where dilute mineral acid was also added, no fructose was detected by HPLC. The cellulose was observed to react to some extent to form insoluble humins and other unidentified products.

Example Reaction for Production of Fructose:

Glucose (49.5 mg, 275 μmol), 2-carboxyphenylboronic acid (45.9 mg, 277 μmol) or other phenylboronic acid (as indicated) and MgO (36.6 mg, 908 μmol) were mixed in DMA or [EMIM]Cl (500 mg). The reaction mixture was heated at 120° C. for 4 h. At 1-h intervals, aliquots of the reaction mixture were removed for analysis by HPLC.

Example 5

Immobilization of 2-Substituted Phenylboronic Acids

A. Scheme 5 (FIG. 5) illustrates exemplary immobilization of dicarboxyphenylboronates on an amine resin (with —$NH_2$ functional group) such as a NovaPEG resin from EMD4Biosciences (EMD Chemicals) or a TentaGel® Resin from RAPP Polymere. In the reactions illustrated, the boronic acid, HOBt, HBTU and DIEA are used in excess relative to the resin, more specifically, exemplary amounts employed are 4 equivalents relative to resin of the phenylboronic acid, HOBt, HBTU and 8 equivalents of DIEA. The phenylboronic acid, HOBt, and HBTU are dissolved in N,N-dimethylformamide (DMF), and DIEA is then added. Argon gas is bubbled through the solution for 15 min, to form activated carbonyls on the boronic acid. The resin is then added and reacted with bubbling argon at room temperature for 2 h. The solution is then removed via vacuum filtration, and the resin is washed with DMF. This general strategy can be employed with various substituted phenylboronates and various resins which can couple with a carboxylic acid group. The reactions of Scheme 5 can also be combined with initial protection of the phenylboronic acid (as exemplified in Scheme 6 or employing boronic acid protecting groups (pinacol, pinanediol or more generally an alkyl diol) that are known in the art) prior to immobilization. The protecting group(s) can be removed or retained until desired to employ the immobilized phenylboronic acid. Retention of protecting groups on the immobilized phenylboronic acid can enhance shelf-life of the immobilized catalyst.

B. Scheme 6 (FIG. 6) illustrates an exemplary method for immobilization of 2-carboxyphenylboronic acid. In the illustrated scheme, 2,4-dimethoxycarbonyl phenylboronic acid is treated with base to form the corresponding oxaborole, which can be isolated as a salt. The oxaborole is then protected with an appropriate protecting group, e.g., pinacol, pinanediol or a diol, such a propylene glycol, and the 4-carboxylic acid group is activated by reaction with N-hydroxysuccinimide to form an N-hydroxysuccinimide ester. The activated ester is then be reacted with an amino functionalized resin, e.g., O-(2-aminoethyl)polyethylene glycol resin to immobilize the protected oxaborole on the resin. The oxaborole is then deprotected, e.g., with trifluoroacetic acid (TFA/$H_2O$) to provide the immobilized 2-carboxyphenylboronic acid. The imobilized 2-carboxyphenylboronic acid can be converted if desired to 2-methoxycarbonyl or the 2-ethoxycarbonyl derivative by methods that are well known in the art.

The exemplary methods of Schemes 5 and 6 or routine adaptation of such methods can be employed to immobilize various 2-substituted phenylboronic acids useful in the methods of this invention.

Example 6

Isotopic Labeling Experiments

Two deuterium-labeling experiments were performed to probe the mechanism of the conversion. In the first, glucose-2-d was converted into HMF by 2-ethoxycarbonylphenylboronic acid and $MgCl_2.6H_2O$. 1HNMR spectroscopy revealed that virtually no deuterium was retained in the HMF product. In the second, unlabeled glucose was converted in the presence of D2O, and a substantial quantity of deuterium was found at C-1 of HMF. Without wishing to be bound by any particular mechanism, it is noted that these results are compatible with a mechanism that avails an enediol intermediate. A similar mechanism is used by the enzyme phosphoglucose isomerase, which catalyzes the interconversion of glucose 6-phosphate and fructose 6-phosphate. Boronate ester-formation is known to be more favorable with fructose than glucose. Results herein demonstrate that certain boronic acids also serve by catalyzing fructose dehydration. It is currently considered that the preferred phenylboronic acid catalysts rely on an ortho carboxyl group because its oxygen can donate electron density into the empty p-orbital of boron, thereby decreasing the strength of the fructose-boronate complex in the nearly water-free medium.

As is noted herein, addition of water can enhance the yield of HMF or furfural. It is currently considered that water attenuates the reactivity of Mg(II), allowing its participation in catalysis, but deterring reaction pathways that lead to humins and decrease the yield of HMF or furfural.

Experimental: 2-Deuteroglucose (48.5 mg, 268 μmol), 2-ethoxycarbonylphenylboronic acid (54.1 mg, 279 μmol), and $MgCl_2.6H_2O$ (126.2 mg, 621 μmol) were dissolved in DMA (532 μL). The reaction mixture was heated at 105° C. for 4 h, placed under high vacuum overnight to remove DMA, extracted with ethyl acetate, concentrated under reduced pressure, and analyzed by 1H NMR spectroscopy. The aldehyde peak of HMF (9.56 ppm) showed <5% deuterium retention, indicating that the isomerization mechanism from glucose to fructose is not a 1,2-hydride shift.

Glucose (100.5 mg, 558 μmol) and 2-ethoxycarbonylphenylboronic acid (120.0 mg, 619 μmol) were dissolved in DMA (1064 μL), and $D_2O$ (500 μL) was added to exchange any labile protons with deuterons. This mixture was then concentrated under reduced pressure to remove $D_2O$ and $H_2O$. The $D_2O$ exchange was repeated. Anhydrous $MgCl_2$ (123.2 mg, 1.29 mmol) and $D_2O$ (150.8 mg, 7.53 mmol) were then added, and the reaction mixture was heated at 105° C. for 4 h, placed under high vacuum overnight to remove DMA, extracted with ethyl acetate, concentrated under reduced pressure, and analyzed by $^1H$ NMR spectroscopy. The aldehyde peak of HMF (9.56 ppm) showed 35% deuterium incorporation relative to other HMF peaks (FIG. 1S), consistent with the isomerization of glucose to fructose proceeding by an enolization mechanism.

Example 7

$^1H$ NMR Binding Affinity Studies

Phenylboronic acids, such as 2-hydroxymethylphenylboronic acid, known to have high affinity for sugar binding were not found to significantly enhance sugar conversion to HMF in the methods of this invention. In contrast, carboxylphenylboronic acids which have been reported (Berube, M.; Dowlut, M.; Hall, D. G. *J. Org. Chem.* 2008, 73, 6471; Dowlut, M.; Hall, D. G. *J. Am. Chem. Soc.* 2006, 128, 4226) to have weak affinity for binding to fructose and glucose significantly enhance sugar conversion to HMF by the methods herein. The binding affinity of various phenylboronic acids has been determined previously under aqueous conditions (Berube et al. 2008 and Dowlut et al. 2006). Reactions of the present invention employ organic solvents and ionic liquids and the binding affinities may be significantly different in such solvents.

An $^1H$ NMR study in deuterated dimethylsulfoxide (DMSO-$d_6$) was conducted to elucidate if 2-carboxyphenylboronic acid coordinates to fructose formed in the course of glucose conversion to HMF (data not shown). Complex formation with 2-carboxyphenylboronic acid was compared to that with phenylboronic acid which is known to form complexes with fructose in aqueous solvents and which is reported to have a higher binding affinity in aqueous solvents toward fructose than glucose (Berube et al. 2008; Dowlut et al. 2006; Hansen, J. S.; Christensen, J. B.; Solling, T. I.; Jakobsen, P.; Hoeg-Jensen, T. *Tetrahedron* 2011, 67, 1334; Springsteen, G.; Wang, B. H. *Tetrahedron* 2002, 58, 5291.)

The phenylboronic acids and sugars were dissolved in DMSO-$d_6$, which served as a deuterated organic solvent substitute for DMA. Both 2-carboxyphenylboronic acid and the unsubstituted phenylboronic acid were observed to form anhydride structures which can be broken up with the addition of water. When fructose and glucose were added, complex formation between 2-carboxyphenylboronic acid with both fructose and glucose was observed. Typically, the aryl hydrogens of the boronic acid demonstrate a distinct shift in their chemical shifts upon complexation to a sugar. [Berube et al. 2008; Dowlut et al. 2006.]

Quantitative binding of fructose and glucose to 2-carboxyphenylboronic acid was demonstrated in each case by two distinct sets of peaks corresponding to the free phenylboronic acid and the corresponding phenyboronic acid-sugar complex. Similar complex formation was observed with phenylboronic acid, but while shifts in the NMR peaks were detected on complex formation as expected, the peaks did not demonstrate a consistency in their shifts inconsistent with what is seen in an aqueous environment. [Berube et al. 2008; Dowlut et al. 2006] The chemical shifts of the aromatic peaks of the free phenylboronic acid and phenylboronic acid-fructose complexes changed according to quantity of sugar present, precluding conclusive peak assignment. This in turn prevented the determination of the specific association constant values of 2-carboxyphenylboronic acid with fructose and glucose. Nonetheless, these data indicate that fructose and glucose do break up the phenylboronic acid anhydride that forms in organic solvent, and that the affinity of the boronic acids for sugars is altered in organic solvents relative to aqueous solvents. $MgCl_2.6H_2O$ was added and the spectra of the phenylboronic acids were reexamined in the presence of fructose and glucose to mimic reaction conditions where HMF formation was enhanced. While some peak broadening was observed, no significant changes to the overall spectra were observed. The addition of $MgCl_2.6H_2O$ does not appear to affect the boronic acid-sugar binding.

Example 7

Catalyst Recovery and Recycling

High catalyst loadings were found to turnover cellulose rapidly (≤2 h). Catalyst recycling can result in significant decreases in process costs. A separation strategy was developed which focused on isolating the 2-carboxy substituted phenylboronic acid (water soluble) from reaction mixtures in which HMF was produced using an anion-exchange resin. The reaction mixture was diluted with water, filtered to remove any humins (which are insoluble byproducts from aldol addition and condensation), extracted with ethyl acetate to remove HMF, and passed through a column of resin. The anionic boronate was retained on the resin and eluted with aqueous base (e.g., aqueous $NH_4HCO_3$ (1 M)) to yield purified boronate. Recovered catalyst was found to retained catalytic activity. This strategy is inapplicable to the substituted phenylboronic acid catalysts that have low water solubility and high solubility in ethyl acetate such as 2-alkoxycarbonyl phenylboronic acids.

Boronic acid moieties become anionic at high pH and partition completely into an aqueous phase. Hence, in an alternative recovery strategy, basic water is added to reaction mixtures containing such phenylboronic acids, e.g., 2-alkoxycarbonylphenylboronic acids, filtered to remove any humins, and extracted with ethyl acetate (see FIG. 8). Removing solvent from the organic phase provided HMF. Evaporating water from the aqueous phase recovered the phenylboronic acid and $MgCl_2$ catalysts. The re-isolated catalysts when reused provided HMF in comparable yield through at least four reaction cycles. This recovery and recycling process can be applied to various phenylboronic acid catalysts of the invention and employed in processes for conversion of various carbohydrates, particularly cellulose. The recovery and recycling process can be applied where HMF, furfural or mixtures thereof are products.

REFERENCES (1) Facing the Hard Truths about Energy. US National Petroleum Council; Washington, D.C., 2007.
(2) No quick switch to low-carbon energy. Kramer, G. J.; Haigh, M. *Nature* 2009, 462, 568.
(3) Beneficial biofuels—the food, energy, and environment trilemma. Tilman, D.; Socolow, R.; Foley, J. A.; Hill, J.; Larson, E.; Lynd, L.; Pacala, S.; Reilly, J.; Searchinger, T.; Somerville, C.; Williams, R. *Science* 2009, 325, 270-271.

(4) Mechanism of formation of 5-(hydroxymethyl)-2-furaldehyde from D-fructose and sucrose. Antal, M. J., Jr.; Mok, W. S. L.; Richards, G. N. Carbohydr. Res. 1990, 199, 91-109.
(5) Liquid-phase catalytic processing of biomass-derived oxygenated hydrocarbons to fuels and chemicals. Chheda, J. N.; Huber, G. W.; Dumesic, J. A. Angew. Chem. Int. Ed. 2007, 46, 7164-7183.
(6) Production of liquid alkanes by aqueous-phase processing of biomass-derived carbohydrates. Huber, G. W.; Chheda, J. N.; Barrett, C. J.; Dumesic, J. A. Science 2005, 308, 1446-1450.
(7) Synthesis, chemistry and applications of 5-hydroxymethylfurfural and its derivatives. Lewkowski, J. ARKIVOC 2001, 17-54.
(8) Production of dimethylfuran for liquid fuels from biomass-derived carbohydrates. Román-Leshkov, Y.; Barrett, C. J.; Liu, Z. Y.; Dumesic, J. A. Nature 2007, 447, 982-986.
(9) Phase modifiers promote efficient production of hydroxymethylfurfural from fructose. Román-Leshkov, Y.; Chheda, J. N.; Dumesic, J. A. Science 2006, 312, 1933-1937.
(10) Catalytic cracking reactions of polyethylene to light alkanes in ionic liquids. Adams, C. J.; Earle, M. J.; Seddon, K. R. Green Chem. 2000, 2, 21-24.
(11) Isomerization of glucose to fructose in the presence of cation-exchanged zeolites and hydrotalcites. Moreau, C.; Durand, R.; Roux, A.; Tichit, D. Appl. Catal. A: Gen. 2000, 193, 257-264.
(12) Catalytic activity of lanthanide(III) ions for the dehydration of hexose. Seri, K.-i.; Inoue, Y.; Ishida, H. Bull. Chem. Soc. Jpn. 2001, 74, 1145-1150.
(13) Glucose reactions with acid and base catalysts in hot compressed water at 473 K. Watanabe, M.; Aizawa, Y.; Lida, T.; Aida, T. M.; Levy, C.; Sue, K.; Inomata, H. Carbohydr. Res. 2005, 340, 1925-1930.
(14) Catalytic glucose and fructose conversions with $TiO_2$ and $ZrO_2$ in water at 473 K: Relationship between reactivity and acid-base property determined by TPD measurement. Watanabe, M.; Aizawa, Y.; Iida, T.; Nishimura, R.; Inomata, H. Appl. Catal. A: Gen. 2005, 295, 150-156.
(15) Catalytic conversion of glucose to 5-hydroxymethylfurfural over $SO_4^{2-}/ZrO_2$ and $SO_4^{2-}/ZrO_2$—$Al_2O_3$ solid acid catalysts. Yan, H.; Yang, Y.; Tong, D.; Xiang, X.; Hu, C. Catal. Commun. 2009, 10, 1558-1563.
(16) Selective dehydration of glucose to hydroxymethylfurfural and a one-pot synthesis of a 4-acetylbutyrolactone from glucose and trioxane in solutions of aluminum salts. Tyrlik, S. K.; Szerszén, D.; Olejnik, M.; Danikiewicz, W. Carbohydr. Res. 1999, 315, 268-272.
(17) Efficient conversion of glucose into 5-hydroxymethylfurfural catalyzed by a common Lewis acid $SnCl_4$ in an ionic liquid. Hu, S.; Zhang, Z.; Song, J.; Zhou, Y.; Han, B. Green Chem. 2009, 11, 1746-1749.
(18) Direct conversion of glucose to 5-(hydroxymethyl)furfural in ionic liquids with lanthanide catalysts. Stålberg, T.; Sørensen, M. G.; Riisager, A. Green Chem. 2010, 12, 321-324.
(19) Syntheses of alkylated malonates on a traceless linker derived soluble polymer support. Zhao, X.-Y.; Janda, K. D. Tetrahedron Lett. 1997, 38, 5437-5440.
(20) Metal chlorides in ionic liquid solvents convert sugars to 5-hydroxymethylfurfural. Zhao, H.; Holladay, J. E.; Brown, H.; Zhang, Z. C. Science 2007, 316, 1597-1600.
(21) Glucose activation by transient $Cr^{2+}$ dimers. Pidko, E. A.; Degirmenci, V.; van Santen, R. A.; Hensen, E. J. M. Angew. Chem. Int. Ed. 2010, 49, 2530-2534.
(22) Selective saccharides dehydration to 5-hydroxymethyl-2-furaldehyde by heterogeneous niobium catalysts. Carlini, C.; Giuttari, M.; Raspolli Galletti, A. M.; Sbrana, G.; Armaroli, T.; Busca, G. Appl. Catal. A: Gen. 1999, 183, 295-302.
(23) An overview of dehydration, aldol-condensation and hydrogenation processes for production of liquid alkanes from biomass-derived carbohydrates. Chheda, J. N.; Dumesic, J. A. Catal. Today 2007, 123, 59-70.
(24) Simple chemical transformation of lignocellulosic biomass into furans for fuels and chemicals. Binder, J. B.; Raines, R. T. J. Am. Chem. Soc. 2009, 131, 1979-1985.
(25) Single-step conversion of cellulose to 5-hydroxymethylfurfural (HMF), a versatile platform chemical. Su, Y.; Brown, H. M.; Huang, X.; Zhou, X.; Amonette, J. E.; Zhang, C. Z. Appl. Catal. A: Gen. 2009, 361, 117-122.
(26) Olefins from alcohols. Brandenberg, W.; Galat, A. J. Am. Chem. Soc. 1950, 72, 3275-3276.
(27) The boric acid dehydration of alcohols. O'Connor, G. L.; Nace, H. R. J. Am. Chem. Soc. 1955, 77, 1578-1581.
(28) Chemistry of sugars in boric-acid solutions. Acree, T. E. Adv. Chem. Ser. 1973, 117, 208-219.
(29) Polyol complexes and structure of the benzeneboronate ion. Lorand, J. P.; Edwards, J. O. J. Org. Chem. 1959, 24, 769-774.
(30) Boronic Acids in Saccharide Recognition. James, T.; Phillips, M.; Shinkai, S.; Royal Society of Chemistry: Cambridge, 2006.
(31) Inhibition of acid-catalyzed depolymerization of cellulose with boric acid in non-aqueous acidic media. Kawamoto, H.; Saito, S.; Saka, S. Carbohydr. Res. 2008a, 343, 249-255.
(32) Stable complex formation with boric acid in pyrolysis of levoglucosan in acidic media. Kawamoto, H.; Saito, S.; Saka, S. J. Anal. Appl. Pyrol. 2008b, 82, 78-82.
(33) 3-Methoxycarbonyl-5-nitrophenylboronic acid: High affinity diol recognition at neutral pH. Mulla, H. R.; Agard, N.J.; Basu, A. Bioorg. Med. Chem. Lett. 2004, 14, 25-27.
(34) A detailed examination of boronic acid-diol complexation. Springsteen, G.; Wang, B. H. Tetrahedron 2002, 58, 5291-5300.
(35) An improved class of sugar-binding boronic acids, soluble and capable of complexing glycosides in neutral water. Dowlut, M.; Hall, D. G. J. Am. Chem. Soc. 2006, 128, 4226-4227.
(36) Benzoboroxoles as efficient glycopyranoside-binding agents in physiological conditions: Structure and selectivity of complex formation. Berube, M.; Dowlut, M.; Hall, D. G. J. Org. Chem. 2008, 73, 6471-6479.
(37) Synergy of boric acid and added salts in the catalytic dehydration of hexoses to 5-hydroxymethylfurfural in water. Hansen, T. S.; Mielby, J; Riisager, A, Green Chem. 2011, 13, 109-114.
(38) Metal-free dehydration of glucose to 5-(hydroxymethyl) furfural in ionic liquids with boric acid as promoter. Stålberg. T.; Rodriquez-Rodriquez, S.; Fristrup, P.; Riisager, A. Chem. Eur. J. 2011, 17, 1456-1464.
(39) Hydrogen production reactions from carbon feedstocks: Fossil fuels and biomass. Navarro, R. M.; Pena, M. A.; Fierro, J. L. Chem. Rev. 2007, 107, 3952-3991.
(40) Biorefineries—Industrial Processes and Products. Kamm, B.; Gruber, P. R.; Kamm, M., Eds; Wiley—VCH: Weinheim, Germany, 2006.
(41) Production of furfural from corn stover hemicellulose. Sproull, R. D.; Bienkowski, P. R.; Tsao, G. T. (1985) Biotechnology and Bioengineering Symposium 15, 561-577.

(42) Selective preparation of furfural from xyloase over microporous solid acid catalysts. Moreau, C.; Durand, R.; Peyron, D.; Duhamet, J.; Rivalier, P. (1988) Ind. Crops Prod. 7, 95-99.
(43) Acid-catalysed hydrolysis of rice hull: Evaluation of furfural production. Mansilla, H. D.; Baeza, J.; Urzua, S.; Maturana, G.; Villasenor, J.; Duran, N. (1998) Bioresour. Technol. 66, 189-193.
(44) Modified versions of sulfated zirconia as catalysts for the conversion of xylose to furfural. Dias, A. S.; Lima, S.; Pillinger, M.; Valente, A. A. (2007) Catal. Lett. 114, 151-160.
(45) The Chemistry and Technology of Furfural and Its Many By-Products. Zeitsch, K. J.; Elsevier: Amsterdam, 2000.
(46) Furfural: Hemicellulose/xylose-derived biochemical. Mamman, A. S.; Lee, J.-M.; Kim, Y.-C.; Hwang, I. T.; Park, N.-J.; Hwang, Y. K.; Chang, J.-S. (2008) Biofuels, Bioprod. Biorefin., 2, 438-454.
(47) Mechanism of formation of 2-furaldehyde from D-xylose. Antal, M. J.; Leesomboon, T.; Mok, W. S.; Richards, G. N. (1991) Carbohydr. Res. 217, 71-85.
(48) Energetics of xylose decomposition as determined using quantum mechanics modeling. Nimlos, M. R.; Qian, X.; Davis, M.; Himmel, M. E.; Johnson, D. K. (2006) J. Phys. Chem. A 110, 11824-11838.
(49) One pot production of 5-hydroxyfurfural with high yield from cellulose by a Bronsted-Lewis-surfactant-combined heteropolyacid catalyst. Zhao, S.; Cheng, M.; Li, J.; Tian, J.; Wang, X. Chem. Commun., January 2011, 47, 2176-2178.
(50) Heck reaction in solid phase synthesis. Yu, K.-L.; Deshpande, M. S.; Vyas, D. M. Tetrahedron Lett. 1994, 35, 8919.
(51) Boronic acid-functionalized nanoparticles: Synthesis by microemulsion polymerization and application as a reusable optical nanosensor for carbohydrates, Cannizzoa, C., Amigoni-Gerbiera, S., Larpent, C. Polymer, February 2005, 46, 1269-1276.
(52) 'Tailored' polymers for supported syntheses using boronic acids, Arimoria, S., Hartleya, J. H., Bellb, M. L., Ohb, C. S., James, T. D., Tetrahedron Lett. December 2000, 41, 10291-10294.
(53) Features of promising technologies for pretreatment of lignocellulosic biomass, Mosier, N., Wyman, C., Dale, B., Elander, R. Lee, Y. Y., Holtzapple, M., Ladish, M., Bioresource Technol. (2005) 96:673-686.
(54) Direct catalytic conversion of furfural to 1,5-pentanediol by hydrogenolysis of the furan ring under mild conditions over Pt/Co2AlO$_4$ catalyst, Wenjie Xu, Haifeng Wang, Xiaohui Liu, Jiawen Ren, Yanqin Wang and Guanzhong Lu Chem. Commun., 2011, 47, 3924-3926.

TABLE 1A

HMF from Glucose

| solvent | boronic acid, mol % | additive, mol % | T (° C.) | time (h) | HMF yield (%) |
|---|---|---|---|---|---|
| DMA | — | MgCl$_2$•6H$_2$O, 200 | 120 | 6 | 29 |
| [EMIM]Cl | — | MgCl$_2$•6H$_2$O, 200 | 100 | 6 | 28 |
| DMA | 4-carboxyphenyl, 100 | — | 120 | 6 | 12 |
| DMA | 3-carboxy-5-nitrophenyl, 100 | — | 120 | 3 | 25 |
| DMA | 2-carboxyphenyl, 100 | — | 120 | 6 | 2 |
| DMA | 4-carboxyphenyl, 100 | Mg, 250 | 100 | 3 | 2 |
| DMA | 3-carboxy-5-nitrophenyl, 100 | Mg, 250 | 100 | 5 | 0 |
| DMA | 2-carboxyphenyl, 100 | Mg, 250 | 100 | 5 | 0 |
| DMA | 2-carboxyphenyl, 100 | MgCl$_2$, 200 | 120 | 1 | 19 |
| DMA | 2-methoxycarbonylphenyl, 100 | MgCl$_2$, 200 | 120 | 1 | 19 |
| DMA | 2-ethoxycarbonylphenyl, 100 | MgCl$_2$, 200 | 120 | 1 | 18 |
| DMA | 2-carboxyphenyl, 100 | MgCl$_2$•6H$_2$O, 200 | 120 | 4 | 54 |
| DMA | 2-methoxycarbonylphenyl, 100 | MgCl$_2$•6H$_2$O, 200 | 120 | 4 | 57 |
| DMA | 2-ethoxycarbonylphenyl, 100 | MgCl$_2$•6H$_2$O, 200 | 120 | 4 | 52 |
| DMA | 2-carboxyphenyl, 100 | MgCl$_2$•6H$_2$O, 200 | 100 | 2 | 50 |
| DMA | 2-carboxyphenyl-dihydrate, 100 | MgCl$_2$•6H$_2$O, 200 | 100 | 3 | 24 |
| DMA | 2-carboxyphenyl-dihydrate (dehydrated), 100 | MgCl$_2$•6H$_2$O, 200 | 100 | 3 | 40 |
| DMA | 2-carboxyphenyl, 100 | CeCl$_3$•7H$_2$O, 200 | 120 | 3 | 51 |
| DMA | 2-carboxyphenyl, 100 | LaCl$_3$•7H$_2$O, 200 | 120 | 3 | 49 |
| DMA | 2-carboxyphenyl, 100 | CaCl$_2$•2H$_2$O, 200 | 120 | 3 | 38 |
| DMA | — | CrCl$_2$, 25 | 100 | 6 | 58 |
| DMA | 2-carboxyphenyl, 100 | CrCl$_2$, 25 | 100 | 6 | 37 |
| DMA | 2-carboxyphenyl, 100 | CrCl$_2$ + 6H$_2$O, 25 | 100 | 6 | 48 |
| DMA | 2-methoxycarbonylphenyl, 100 | CrCl$_2$, 25 | 100 | 1.5 | 39 |
| DMA | 2-methoxycarbonylphenyl, 100 | CrCl$_2$ + 6H$_2$O, 25 | 100 | 1.5 | 28 |
| DMA | 2-ethoxycarbonylphenyl, 100 | CrCl$_2$, 25 | 100 | 3 | 33 |
| DMA | 2-ethoxycarbonylphenyl, 100 | CrCl$_2$ + 6H$_2$O, 25 | 100 | 1.5 | 26 |
| DMA | — | LiCl, 300 | 120 | 6 | 5 |
| DMA | 2-carboxyphenyl, 100 | LiCl + 6H$_2$O, 200 | 105 | 4 | 16 |
| DMA | — | LiBr, 300 | 120 | 1.5 | 2 |
| DMA | 2-carboxyphenyl, 100 | LiBr + 6H$_2$O, 200 | 105 | 4 | 4 |
| DMA | — | NaCl, 300 | 120 | 4.5 | 2 |
| DMA | 2-carboxyphenyl, 100 | NaCl + 6H$_2$O, 200 | 105 | 4 | 2 |
| DMA | — | KCl, 300 | 120 | 6 | 5 |
| DMA | 2-carboxyphenyl, 100 | KCl + 6H$_2$O, 200 | 105 | 4 | 2 |
| DMA | — | CuCl, 300 | 120 | 1.5 | 2 |
| DMA | 2-carboxyphenyl, 100 | CuCl + 6H$_2$O, 200 | 105 | 4 | 0 |
| DMA | — | CuCl$_2$, 300 | 120 | 6 | 9 |
| DMA | 2-carboxyphenyl, 100 | CuCl$_2$ + 6H$_2$O, 200 | 105 | 4 | 4 |

TABLE 1A-continued

HMF from Glucose

| solvent | boronic acid, mol % | additive, mol % | T (° C.) | time (h) | HMF yield (%) |
|---|---|---|---|---|---|
| DMA | — | CsCl | 120 | 6 | 0 |
| DMA | 2-carboxyphenyl, 100 | CsCl + 6H$_2$O, 200 | 105 | 4 | 7 |
| DMA | — | FeCl$_2$, 300 | 120 | 4.5 | 7 |
| DMA | 2-carboxyphenyl, 100 | FeCl$_2$ + 6H$_2$O, 200 | 105 | 4 | 10 |
| DMA | — | FeCl$_3$, 300 | 120 | 4.5 | 4 |
| DMA | 2-carboxyphenyl, 100 | FeCl$_3$ + 6H$_2$O, 200 | 105 | 4 | 4 |
| DMA | — | MoCl$_3$, 300 | 120 | 1.5 | 12 |
| DMA | 2-carboxyphenyl, 100 | MoCl$_3$ + 6H$_2$O, 200 | 105 | 1 | 15 |
| DMA | — | VCl$_3$, 300 | 120 | 1.5 | 16 |
| DMA | 2-carboxyphenyl, 100 | VCl$_3$ + 6H$_2$O, 200 | 105 | 4 | 29 |
| DMA | — | RbCl, 300 | 120 | 6 | 0 |
| DMA | 2-carboxyphenyl, 100 | RbCl + 6H$_2$O, 200 | 105 | 4 | 2 |
| DMA | 2-carboxyphenyl, 100 | NaBr + 6H$_2$O, 200 | 105 | 4 | 2 |
| DMA | — | ZnCl$_2$, 300 | 120 | 6 | 21 |
| DMA | 2-carboxyphenyl, 100 | ZnCl$_2$ + 6H$_2$O, 200 | 105 | 4 | 18 |
| DMA | 2-carboxyphenyl, 100 | MgCl$_2$, 200 | 100 | 3 | 22 |
| DMA | 2-carboxyphenyl, 100 | MgCl$_2$ + H$_2$O, 200 | 100 | 3 | 24 |
| DMA | 2-carboxyphenyl, 100 | MgCl$_2$ + 2H$_2$O, 200 | 100 | 4.5 | 28 |
| DMA | 2-carboxyphenyl, 100 | MgCl$_2$ + 3H$_2$O, 200 | 100 | 6 | 30 |
| DMA | 2-carboxyphenyl, 100 | MgCl$_2$ + 4H$_2$O, 200 | 100 | 6 | 33 |
| DMA | 2-carboxyphenyl, 100 | MgCl$_2$ + 5H$_2$O, 200 | 100 | 6 | 36 |
| DMA | 2-carboxyphenyl, 100 | MgCl$_2$ + 6H$_2$O, 200 | 100 | 6 | 40 |
| DMA | 2-carboxyphenyl, 100 | MgCl$_2$ + 7H$_2$O, 200 | 100 | 6 | 43 |
| DMA | 2-carboxyphenyl, 100 | MgCl$_2$ + 8H$_2$O, 200 | 100 | 6 | 43 |
| DMA | 2-carboxyphenyl, 100 | MgCl$_2$ + 9H$_2$O, 200 | 100 | 6 | 46 |
| DMA | 2-carboxyphenyl, 100 | MgCl$_2$ + 10H$_2$O, 200 | 100 | 6 | 46 |
| DMA | 2-carboxyphenyl, 100 | MgCl$_2$ + 11H$_2$O, 200 | 100 | 6 | 56 |
| DMA | 2-carboxyphenyl, 100 | MgCl$_2$ + 12H$_2$O, 200 | 100 | 6 | 54 |
| DMA | 2-carboxyphenyl, 100 | MgCl$_2$•6H$_2$O + H$_2$O, 200 | 100 | 3 | 54 |
| DMA | 2-carboxyphenyl, 100 | MgCl$_2$•6H$_2$O + 2H$_2$O, 200 | 100 | 4.5 | 56 |
| DMA | 2-carboxyphenyl, 100 | MgCl$_2$•6H$_2$O + 3H$_2$O, 200 | 100 | 6 | 57 |
| DMA | 2-carboxyphenyl, 100 | MgCl$_2$•6H$_2$O + 4H$_2$O, 200 | 100 | 4.5 | 57 |
| DMA | 2-carboxyphenyl, 100 | MgCl$_2$•6H$_2$O + 5H$_2$O, 200 | 100 | 4.5 | 58 |
| DMA | 4-carboxyphenyl, 100 | MgCl$_2$•6H$_2$O, 200 | 100 | 9 | 28 |
| DMA | 3-carboxy-5-nitrophenyl, 100 | MgCl$_2$•6H$_2$O, 200 | 100 | 9 | 36 |
| DMA | 2-carboxyphenyl, 100 | MgCl$_2$•6H$_2$O, 200 | 100 | 9 | 50 |
| DMA | 3-carboxyphenyl, 100 | MgCl$_2$•6H$_2$O, 200 | 100 | 7.5 | 25 |
| DMA | 2,4-bis(trifluoromethyl)phenyl, 100 | MgCl$_2$•6H$_2$O, 200 | 100 | 7.5 | ND |
| DMA | 3,5-bis(trifluoromethyl)phenyl, 100 | MgCl$_2$•6H$_2$O, 200 | 100 | 9 | 25 |
| DMA | 4-methylphenyl, 100 | MgCl$_2$•6H$_2$O, 200 | 120 | 9 | 23 |
| DMA | benzoic acid, 100 | MgCl$_2$•6H$_2$O, 200 | 100 | 9 | 22 |
| DMA | phthalic acid, 100 | MgCl$_2$•6H$_2$O, 200 | 100 | 9 | 18 |
| DMA | 2-methoxycarbonylphenyl, 100 | MgCl$_2$•6H$_2$O, 200 | 100 | 6 | 59 |
| DMA | 2-ethoxycarbonylphenyl, 100 | MgCl$_2$•6H$_2$O, 200 | 100 | 4.5 | 52 |
| DMA | 2-hydroxymethylphenyl, 100 | MgCl$_2$•6H$_2$O, 200 | 100 | 6 | 6 |
| DMA | 2-(N,N-dimethylaminomethyl)phenyl, 100 | MgCl$_2$•6H$_2$O, 200 | 100 | 6 | 2 |
| DMA | 5-amino-2-hydroxymethylphenyl, 100 | MgCl$_2$•6H$_2$O, 200 | 100 | 1 | 3 |
| DMA | 2-methoxyphenyl, 100 | MgCl$_2$•6H$_2$O, 200 | 100 | 5 | 33 |
| DMA | 2,6-dimethoxyphenyl, 100 | MgCl$_2$•6H$_2$O, 200 | 100 | 6 | 28 |
| DMA | 2,6-dimethylphenyl, 100 | MgCl$_2$•6H$_2$O, 200 | 100 | 6 | 27 |
| DMA | 2-nitrophenyl, 100 | — | 105 | 4 | 0 |
| DMA | 2-nitrophenyl, 100 | MgCl$_2$•6H$_2$O, 200 | 105 | 4 | 7 |
| [EMIM]Cl | 2-nitrophenyl, 100 | — | 105 | 4 | 26 |
| [EMIM]Cl | 2-nitrophenyl, 100 | MgCl$_2$•6H$_2$O, 200 | 105 | 4 | 18 |
| DMA | 2-formylphenyl, 100 | — | 105 | 4 | 0 |
| DMA | 2-formylphenyl, 100 | MgCl$_2$•6H$_2$O, 200 | 105 | 4 | 4 |
| [EMIM]Cl | 2-formylphenyl, 100 | — | 105 | 3 | 37 |
| [EMIM]Cl | 2-formylphenyl, 100 | MgCl$_2$•6H$_2$O, 200 | 105 | 4 | 31 |
| DMA | 2-acetylphenyl, 100 | — | 105 | 4 | 0 |
| DMA | 2-acetylphenyl, 100 | MgCl$_2$•6H$_2$O, 200 | 105 | 4 | 2 |
| [EMIM]Cl | 2-acetylphenyl, 100 | — | 105 | 4 | 21 |
| [EMIM]Cl | 2-acetylphenyl, 100 | MgCl$_2$•6H$_2$O, 200 | 105 | 4 | 14 |
| DMA | 2-aminocarbonylphenyl, 100 | — | 105 | 4 | 0 |
| DMA | 2-aminocarbonylphenyl, 100 | MgCl$_2$•6H$_2$O, 200 | 105 | 4 | 8 |
| [EMIM]Cl | 2-aminocarbonylphenyl, 100 | — | 105 | 4 | 2 |
| [EMIM]Cl | 2-aminocarbonylphenyl, 100 | MgCl$_2$•6H$_2$O, 200 | 105 | 4 | 15 |
| DMA | 2-carboxyphenyl, 100 | MgCl$_2$•6H$_2$O, 200 | 120 | 4 | 54 |
| DMA | 2-carboxyphenyl, 50 | MgCl$_2$•6H$_2$O, 200 | 120 | 6 | 48 |
| DMA | 2-carboxyphenyl, 25 | MgCl$_2$•6H$_2$O, 200 | 120 | 6 | 46 |
| DMA | 2-carboxyphenyl, 10 | MgCl$_2$•6H$_2$O, 200 | 120 | 6 | 31 |

TABLE 1A-continued

HMF from Glucose

| solvent | boronic acid, mol % | additive, mol % | T (° C.) | time (h) | HMF yield (%) |
|---|---|---|---|---|---|
| DMA | 2-carboxyphenyl, 100 | MgCl$_2$•6H$_2$O, 250 | 110 | 6 | 55 |
| DMA | 2-carboxyphenyl, 100 | MgCl$_2$•6H$_2$O, 200 | 110 | 6 | 51 |
| DMA | 2-carboxyphenyl, 100 | MgCl$_2$•6H$_2$O, 150 | 110 | 5 | 48 |
| DMA | 2-carboxyphenyl, 100 | MgCl$_2$•6H$_2$O, 100 | 110 | 5 | 43 |
| [EMIm]Cl | 2-carboxyphenyl, 200 | MgBr$_2$•6H$_2$O, 400 | 105 | 3 | 50 |
| [EMIm]Cl | 2-methoxycarbonylphenyl, 200 | MgBr$_2$•6H$_2$O, 400 | 105 | 2 | 40 |
| [EMIm]Cl | 2-ethoxycarbonylphenyl, 200 | MgBr$_2$•6H$_2$O, 400 | 105 | 1 | 35 |
| [EMIm]Cl | 2-carboxyphenyl, 200 | MgI$_2$ + 6H$_2$O, 400 | 105 | 3 | 54 |
| [EMIm]Cl | 2-methoxycarbonylphenyl, 200 | MgI$_2$ + 6H$_2$O, 400 | 105 | 2 | 47 |
| [EMIm]Cl | 2-ethoxycarbonylphenyl, 200 | MgI$_2$ + 6H$_2$O, 400 | 105 | 1 | 29 |
| [EMIm]Cl | 2-carboxyphenyl, 200 | MgBr$_2$, 400 | 105 | 2 | 29 |
| [EMIm]Cl | 2-methoxycarbonylphenyl, 200 | MgBr$_2$, 400 | 105 | 2 | 31 |
| [EMIm]Cl | 2-ethoxycarbonylphenyl, 200 | MgBr$_2$, 400 | 105 | 1 | 28 |
| [EMIm]Cl | 2-carboxyphenyl, 200 | MgI$_2$, 400 | 105 | 2 | 11 |
| [EMIm]Cl | 2-methoxycarbonylphenyl, 200 | MgI$_2$, 400 | 105 | 3 | 31 |
| [EMIm]Cl | 2-ethoxycarbonylphenyl, 200 | MgI$_2$, 400 | 105 | 1 | 18 |

Mol % and molar yield are relative to the glucose in the reaction mixture.
ND = not determined.
In this case, HMF was generated but yield could not be determined because under HPLC conditions used, the HMF peak overlapped the boronic acid peak.

TABLE 1B

Metal halides for glucose conversion to HMF in DMA

| metal halide, mol % | T (° C.) | time (h) | HMF molar yield (%) |
|---|---|---|---|
| CrCl$_2$, 25 | 100 | 6 | 58 |
| MgCl$_2$•6H$_2$O, 200 | 120 | 6 | 29 |
| CeCl$_3$•7H$_2$O, 300 | 120 | 3 | 22 |
| LaCl$_3$•7H$_2$O, 300 | 120 | 6 | 22 |
| CaCl$_2$•2H$_2$O, 300 | 120 | 6 | 13 |
| LiCl, 300 | 120 | 6 | 5 |
| LiBr, 300 | 120 | 6 | 1 |
| NaCl, 300 | 120 | 6 | 0 |
| KCl, 300 | 120 | 6 | 0 |
| CuCl, 300 | 120 | 6 | 12 |
| CuCl$_2$, 300 | 120 | 6 | 9 |
| CsCl, 300 | 120 | 6 | 0 |
| FeCl$_2$, 300 | 120 | 4.5 | 7 |
| FeCl$_3$, 300 | 120 | 4.5 | 4 |
| MoCl$_3$, 300 | 120 | 1.5 | 12 |
| VCl$_3$, 300 | 120 | 1.5 | 16 |
| RbCl, 300 | 120 | 6 | 0 |
| ZnCl$_2$, 300 | 120 | 6 | 21 |
| BaCl$_2$•2H$_2$O, 300 | 120 | 6 | 0 |
| CoCl$_2$•6H$_2$O, 300 | 120 | 3 | 11 |
| PdCl$_2$, 300 | 120 | 6 | 4 |
| MnCl$_2$•4H$_2$O, 300 | 120 | 6 | 10 |
| NiCl$_2$•6H$_2$O, 300 | 120 | 3 | 32 |

Mol % and HMF yield are relative to the glucose in the reaction.

TABLE 1C

Boronic acid screening for glucose conversion to HMF with MgCl$_2$•6H$_2$O in DMA

| boronic acid, mol % | additive, mol % | T (° C.) | time (h) | HMF molar yield (%) |
|---|---|---|---|---|
| phenylboronic acid, 100 | | 105 | 4 | 0 |
| phenylboronic acid, 100 | MgCl$_2$•6H$_2$O, 200 | 105 | 4 | 4 |
| 2-(hydroxymethyl)phenyl, 100 | | 100 | 6 | 0 |
| 2-(hydroxymethyl)phenyl, 100 | MgCl$_2$•6H$_2$O, 200 | 100 | 6 | 6 |
| 2-carboxyphenyl, 100 | | 120 | 6 | 2 |
| 2-carboxyphenyl, 100 | MgCl$_2$•6H$_2$O, 200 | 120 | 4 | 54 |
| 2-carboxyphenyl-dihydrate, 100 | MgCl$_2$•6H$_2$O, 200 | 100 | 3 | 24 |
| 2-carboxyphenyl-dehydrate*, 100 | MgCl$_2$•6H$_2$O, 200 | 100 | 3 | 40 |
| 2-methoxycarbonylphenyl, 100 | | 100 | 6 | 22 |
| 2-methoxycarbonylphenyl, 100 | MgCl$_2$•6H$_2$O, 200 | 120 | 4 | 57 |
| 2-ethoxycarbonylphenyl, 100 | | 100 | 6 | 15 |
| 2-ethoxycarbonylphenyl, 100 | MgCl$_2$•6H$_2$O, 200 | 120 | 4 | 52 |

Mol % and molar yield are relative to the glucose in the reaction.

*2-Carboxyphenylboronic acid-dihydrate was dissolved in methanol to disrupt the hydrate's lattice structure. It was then concentrated under reduced pressure to remove water and methanol.

TABLE 1D

Boronic acid screening for glucose conversion to HMF with MgCl$_2$•6H$_2$O in DMA

| boronic (or other) acid | metal halide | T (° C.) | time (h) | HMF molar yield (%) |
|---|---|---|---|---|
| phenylboronic | — | 105 | 4 | 0 |
| phenylboronic | MgCl$_2$•6H$_2$O | 105 | 4 | 4 |
| 2-(hydroxymethyl)phenyl | — | 100 | 6 | 0 |
| 2-(hydroxymethyl)phenyl | MgCl$_2$•6H$_2$O | 100 | 6 | 6 |
| 2-formylphenyl | — | 105 | 4 | 0 |
| 2-formylphenyl | MgCl$_2$•6H$_2$O | 105 | 4 | 4 |
| 2-acetylphenyl | — | 105 | 4 | 0 |
| 2-acetylphenyl | MgCl$_2$•6H$_2$O | 105 | 4 | 2 |
| 2-aminocarbonylphenyl | — | 105 | 4 | 0 |
| 2-aminocarbonylphenyl | MgCl$_2$•6H$_2$O | 105 | 4 | 8 |
| 2-nitrophenyl | — | 105 | 4 | 0 |
| 2-nitrophenyl | MgCl$_2$•6H$_2$O | 105 | 4 | 7 |
| 2-(N,N-dimethylaminomethyl)phenyl | — | 120 | 6 | 0 |
| 2-(N,N-dimethylaminomethyl)phenyl | MgCl$_2$•6H$_2$O | 120 | 6 | 2 |
| 2-methoxyphenyl | — | 120 | 6 | 6 |
| 2-methoxyphenyl | MgCl$_2$•6H$_2$O | 120 | 5 | 33 |
| 2,4-bis(trifluoromethyl)phenyl | — | 100 | 9 | ND* |
| 2,4-bis(trifluoromethyl)phenyl | MgCl$_2$•6H$_2$O | 100 | 9 | ND* |
| 5-amino-2-hydroxymethylphenyl | — | 120 | 1 | 6 |
| 5-amino-2-hydroxymethylphenyl | MgCl$_2$•6H$_2$O | 120 | 1 | 3 |
| 2,6-dimethoxyphenyl | — | 120 | 6 | 0 |
| 2,6-dimethoxyphenyl | MgCl$_2$•6H$_2$O | 120 | 6 | 28 |
| 2,6-dimethylphenyl | — | 120 | 6 | 8 |
| 2,6-dimethylphenyl | MgCl$_2$•6H$_2$O | 120 | 6 | 27 |
| 3-carboxyphenyl | — | 100 | 7.5 | 24 |
| 3-carboxyphenyl | MgCl$_2$•6H$_2$O | 100 | 7.5 | 25 |
| 3-carboxy-5-nitrophenyl | — | 100 | 4.5 | 5 |
| 3-carboxy-5-nitrophenyl | MgCl$_2$•6H$_2$O | 100 | 9 | 36 |
| 3,5-bis(trifluoromethyl)phenyl | — | 100 | 6 | 18 |
| 3,5-bis(trifluoromethyl)phenyl | MgCl$_2$•6H$_2$O | 100 | 9 | 25 |
| 4-carboxyphenyl | — | 100 | 6 | 1 |
| 4-carboxyphenyl | MgCl$_2$•6H$_2$O | 100 | 9 | 28 |
| 4-methylphenyl | — | 120 | 6 | 0 |
| 4-methylphenyl | MgCl$_2$•6H$_2$O | 120 | 9 | 23 |
| Benzoic acid | MgCl$_2$•6H$_2$O | 100 | 9 | 22 |
| Phthalic acid | MgCl$_2$•6H$_2$O | 100 | 9 | 18 |

Boronic and other acids are at 1 equiv. and MgCl$_2$•6H$_2$O is at 2 equiv. relative to glucose. Glucose was at 10 wt % relative to DMA. Mol % and HMF yield are relative to glucose. ND = not determined, because HMF and the boronic acid have the same HPLC retention time.

TABLE 1E

HMF from glucose in DMA using hydrated metal chlorides and boronic acids

| boronic acid, mol % | additive, mol %* | T (° C.) | time (h) | HMF molar yield (%) |
|---|---|---|---|---|
| 2-carboxyphenyl, 100 | CrCl$_2$, 25 | 100 | 6 | 37 |
| 2-carboxyphenyl, 100 | CrCl$_2$ + 6H$_2$O, 25 | 100 | 6 | 48 |
| 2-methoxycarbonylphenyl, 100 | CrCl$_2$, 25 | 100 | 1.5 | 39 |
| 2-methoxycarbonylphenyl, 100 | CrCl$_2$ + 6H$_2$O, 25 | 100 | 1.5 | 28 |
| 2-ethoxycarbonylphenyl, 100 | CrCl$_2$, 25 | 100 | 3 | 33 |
| 2-ethoxycarbonylphenyl, 100 | CrCl$_2$ + 6H$_2$O, 25 | 100 | 1.5 | 26 |
| 2-carboxyphenyl, 100 | MgCl$_2$, 200 | 120 | 1 | 19 |
| 2-carboxyphenyl, 100 | MgCl$_2$•6H$_2$O, 200 | 120 | 4 | 54 |
| 2-methoxycarbonylphenyl, 100 | MgCl$_2$, 200 | 120 | 1 | 19 |
| 2-methoxycarbonylphenyl, 100 | MgCl$_2$•6H$_2$O, 200 | 120 | 4 | 57 |
| 2-ethoxycarbonylphenyl, 100 | MgCl$_2$, 200 | 120 | 1 | 18 |
| 2-ethoxycarbonylphenyl, 100 | MgCl$_2$•6H$_2$O, 200 | 120 | 4 | 52 |
| 2-carboxyphenyl, 100 | CeCl$_3$•7H$_2$O, 300 | 120 | 3 | 51 |
| 2-carboxyphenyl, 100 | LaCl$_3$•7H$_2$O, 300 | 120 | 3 | 49 |
| 2-carboxyphenyl, 100 | CaCl$_2$•2H$_2$O, 300 | 120 | 3 | 38 |
| 2-carboxyphenyl, 100 | LiCl + 6H$_2$O, 300 | 105 | 4 | 16 |
| 2-carboxyphenyl, 100 | LiBr + 6H$_2$O, 300 | 105 | 4 | 4 |
| 2-carboxyphenyl, 100 | NaCl + 6H$_2$O, 300 | 105 | 4 | 2 |
| 2-carboxyphenyl, 100 | KCl + 6H$_2$O, 300 | 105 | 4 | 2 |
| 2-carboxyphenyl, 100 | CuCl + 6H$_2$O, 300 | 105 | 4 | 0 |
| 2-carboxyphenyl, 100 | CuCl$_2$ + 6H$_2$O, 300 | 105 | 4 | 4 |
| 2-carboxyphenyl, 100 | CsCl + 6H$_2$O, 300 | 105 | 4 | 7 |
| 2-carboxyphenyl, 100 | FeCl$_2$ + 6H$_2$O, 300 | 105 | 4 | 10 |
| 2-carboxyphenyl, 100 | FeCl$_3$ + 6H$_2$O, 300 | 105 | 4 | 4 |
| 2-carboxyphenyl, 100 | MoCl$_3$ + 6H$_2$O, 300 | 105 | 1 | 15 |
| 2-carboxyphenyl, 100 | VCl$_3$ + 6H$_2$O, 300 | 105 | 4 | 29 |
| 2-carboxyphenyl, 100 | RbCl + 6H$_2$O, 300 | 105 | 4 | 2 |
| 2-carboxyphenyl, 100 | ZnCl$_2$ + 6H$_2$O, 300 | 105 | 4 | 18 |
| 2-carboxyphenyl, 100 | BaCl$_2$•2H$_2$O, 300 | 105 | 4 | 1 |
| 2-carboxyphenyl, 100 | CoCl$_2$•6H$_2$O, 300 | 105 | 4 | 17 |
| 2-carboxyphenyl, 100 | PdCl$_2$ + 6H$_2$O, 300 | 105 | 4 | 3 |
| 2-carboxyphenyl, 100 | MnCl$_2$•4H$_2$O, 300 | 105 | 4 | 5 |
| 2-carboxyphenyl, 100 | NiCl$_2$•6H$_2$O, 300 | 105 | 4 | 24 |

Mol % and molar yield are relative to the glucose in the reaction.
*Added molar water eq. are relative to the metal chloride salt.

TABLE 1F

Water ratios in DMA for glucose conversion to HMF

| metal catalyst | added water molar eq. | total water molar equivalents | T (° C.) | time (h) | HMF molar yield (%) |
|---|---|---|---|---|---|
| MgCl$_2$ | 0 | 0 | 100 | 3 | 22 |
| MgCl$_2$ | 1 | 1 | 100 | 3 | 24 |
| MgCl$_2$ | 2 | 2 | 100 | 4.5 | 28 |
| MgCl$_2$ | 3 | 3 | 100 | 6 | 30 |
| MgCl$_2$ | 4 | 4 | 100 | 6 | 33 |
| MgCl$_2$ | 5 | 5 | 100 | 6 | 36 |
| MgCl$_2$ | 6 | 6 | 100 | 6 | 40 |
| MgCl$_2$ | 7 | 7 | 100 | 6 | 43 |
| MgCl$_2$ | 8 | 8 | 100 | 6 | 43 |
| MgCl$_2$ | 9 | 9 | 100 | 6 | 46 |
| MgCl$_2$ | 10 | 10 | 100 | 6 | 46 |
| MgCl$_2$ | 11 | 11 | 100 | 6 | 56 |
| MgCl$_2$ | 12 | 12 | 100 | 6 | 54 |
| MgCl$_2$•6H$_2$O | 1 | 13 | 100 | 3 | 54 |
| MgCl$_2$•6H$_2$O | 2 | 14 | 100 | 4.5 | 56 |
| MgCl$_2$•6H$_2$O | 3 | 15 | 100 | 6 | 57 |
| MgCl$_2$•6H$_2$O | 4 | 16 | 100 | 4.5 | 57 |
| MgCl$_2$•6H$_2$O | 5 | 17 | 100 | 4.5 | 58 |

Mol %, molar yield, and water molar equivalents are relative to the glucose in the reaction.
2-Carboxyphenylboronic acid was used at 100 mol % and MgCl$_2$ at 200 mol % relative to glucose.

TABLE 1G

Catalyst concentration screening for glucose to HMF conversion

| boronic acid, mol % | metal catalyst, mol % | T (° C.) | time (h) | HMF molar yield (%) |
|---|---|---|---|---|
| 2-carboxyphenyl, 100 | MgCl$_2$•6H$_2$O, 200 | 120 | 4 | 54 |
| 2-carboxyphenyl, 50 | MgCl$_2$•6H$_2$O, 200 | 120 | 6 | 48 |
| 2-carboxyphenyl, 25 | MgCl$_2$•6H$_2$O, 200 | 120 | 6 | 46 |
| 2-carboxyphenyl, 10 | MgCl$_2$•6H$_2$O, 200 | 120 | 6 | 31 |
| 2-carboxyphenyl, 100 | MgCl$_2$•6H$_2$O, 250 | 110 | 6 | 55 |
| 2-carboxyphenyl, 100 | MgCl$_2$•6H$_2$O, 200 | 110 | 5 | 51 |
| 2-carboxyphenyl, 100 | MgCl$_2$•6H$_2$O, 150 | 110 | 5 | 48 |
| 2-carboxyphenyl, 100 | MgCl$_2$•6H$_2$O, 100 | 110 | 5 | 43 |

Glucose at 10 wt % relative to DMA.
Mol % and HMF yield are relative to Glucose.

TABLE 1H

Selected Results Conversion of glucose to HMF in DMA

| metal chloride, mol % | boronic acid | T (° C.) | time (h) | HMF molar yield (%) |
|---|---|---|---|---|
| — | — | 100 | 6 | 0 |
| $CrCl_2$, 25 | — | 100 | 6 | 58 |
| $MgCl_2 \cdot 6H_2O$, 200 | — | 120 | 6 | 29 |
| $NiCl_2 \cdot 6H_2O$, 300 | — | 120 | 3 | 32 |
| $ZnCl_2$, 300 | — | 120 | 6 | 21 |
| $CeCl_3 \cdot 7H_2O$, 300 | — | 120 | 3 | 22 |
| $LaCl_3 \cdot 7H_2O$, 300 | — | 120 | 6 | 22 |
| — | 2-carboxyphenyl | 120 | 6 | 2 |
| $MgCl_2 \cdot 6H_2O$, 200 | 2-carboxyphenyl | 120 | 4 | 54 |
| $NiCl_2 \cdot 6H_2O$, 300 | 2-carboxyphenyl | 105 | 4 | 24 |
| $ZnCl_2$, 300 | 2-carboxyphenyl | 105 | 4 | 18 |
| $CeCl_3 \cdot 7H_2O$, 300 | 2-carboxyphenyl | 120 | 3 | 51 |
| $LaCl_3 \cdot 7H_2O$, 300 | 2-carboxyphenyl | 120 | 3 | 49 |
| — | 2-methoxycarbonylphenyl | 100 | 6 | 22 |
| $MgCl_2 \cdot 6H_2O$, 200 | 2-methoxycarbonylphenyl | 120 | 4 | 57 |
| — | 2-ethoxycarbonylphenyl | 100 | 6 | 15 |
| $MgCl_2 \cdot 6H_2O$, 200 | 2-ethoxycarbonylphenyl | 120 | 4 | 52 |

Glucose and boronic acid were 10 wt % relative to solvent.
Mol % and HMF yield are relative to glucose.

TABLE 2A

Initial Data For HMF Production From Various Sugars Other Than Glucose

| sugar | solvent | T (° C.) | time (h) | HMF yield (%) | furfural yield (%) |
|---|---|---|---|---|---|
| lactose | DMA | 105 | 4 | 12 | |
| lactose | [EMIM]Cl | 105 | 4 | 14 | |
| galactose | DMA | 105 | 4 | 31 | |
| galactose | [EMIM]Cl | 105 | 2 | 26 | |
| mannose | DMA | 105 | 4 | 46 | |
| mannose | [EMIM]Cl | 105 | 1 | 50 | |
| sorbose | DMA | 105 | 2 | 43 | |
| sorbose | [EMIM]Cl | 105 | 1 | 40 | |
| tagatose | DMA | 105 | 1 | 30 | |
| tagatose | [EMIM]Cl | 105 | 1 | 25 | |
| arabinose | DMA | 105 | 4 | | 36 |
| arabinose | [EMIM]Cl | 105 | 2 | | 31 |
| xylose | DMA | 105 | 3 | | 45 |
| xylose | [EMIM]Cl | 105 | 2 | | 45 |

Reaction mixture contained 2-carboxyphenylboronic acid (100 mol %) and $MgCl_2 \cdot 6H_2O$ (200 mol %).
Mol % and molar yields are relative to the sugar.

TABLE 2B

Fructose to HMF conversion with boronic acids

| boronic acid, mol % | additive, mol % | T (° C.) | time (h) | HMF molar yiel (%) |
|---|---|---|---|---|
| 2-carboxyphenyl, 100 | | 105 | 4 | 13 |
| 2-carboxyphenyl, 100 | $MgCl_2 \cdot 6H_2O$, 200 | 105 | 2 | 61 |
| 2-methoxycarbonylphenyl, 100 | | 105 | 4 | 40 |
| 2-methoxycarbonylphenyl, 100 | $MgCl_2 \cdot 6H_2O$, 200 | 105 | 4 | 52 |
| 2-ethoxycarbonylphenyl, 10 | | 105 | 3 | 84 |
| 2-ethoxycarbonylphenyl, 100 | $MgCl_2 \cdot 6H_2O$, 200 | 105 | 4 | 59 |

Mol % and molar yield are relative to the fructose in the reaction.

TABLE 2C

Ketohexose conversion using 2-carboxyl phenylboronic acids.

| ketohexose | solvent | phenylboronic acid | metal chloride | T (° C.) | time (h) | HMF molar yield (%) |
|---|---|---|---|---|---|---|
| psicose | DMA | 2-carboxy | $MgCl_2 \cdot 6H_2O$ | 105 | 4 | 39 |
| psicose | DMA | 2-methoxycarbonyl | | 105 | 4 | 51 |
| psicose | DMA | 2-ethoxycarbonyl | | 105 | 4 | 62 |
| fructose | DMA | 2-carboxy | $MgCl_2 \cdot 6H_2O$ | 105 | 4 | 53 |
| fructose | DMA | 2-methoxycarbonyl | $MgCl_2 \cdot 6H_2O$ | 105 | 4 | 52 |
| fructose | DMA | 2-ethoxycarbonyl | | 105 | 3 | 84 |
| sorbose | DMA | 2-carboxy | $MgCl_2 \cdot 6H_2O$ | 105 | 4 | 57 |
| sorbose | DMA | 2-methoxycarbonyl | $MgCl_2 \cdot 6H_2O$ | 105 | 4 | 52 |
| sorbose | DMA | 2-ethoxycarbonyl | | 105 | 4 | 66 |
| tagatose | DMA | 2-carboxy | $MgCl_2 \cdot 6H_2O$ | 105 | 4 | 32 |
| tagatose | DMA | 2-methoxycarbonyl | | 105 | 4 | 35 |
| tagatose | DMA | 2-ethoxycarbonyl | | 105 | 4 | 45 |

Boronic acids were used as 1 eq. and $MgCl_2 \cdot 6H_2O$ as 2.5 eq. relative to the sugar. Sugars were used as 10 wt % relative to the DMA. Molar yield is relative to the sugar.

TABLE 2D

Aldohexose conversion using 2-carboxyl phenylboronic acids.

| aldohexose | solvent | phenylboronic acid | metal chloride | T (° C.) | time (h) | HMF molar yield (%) |
|---|---|---|---|---|---|---|
| allose | DMA | 2-carboxy | $MgCl_2 \cdot 6H_2O$ | 105 | 4 | 8 |
| allose | DMA | 2-methoxycarbonyl | $MgCl_2 \cdot 6H_2O$ | 105 | 4 | 26 |
| allose | DMA | 2-ethoxycarbonyl | $MgCl_2 \cdot 6H_2O$ | 105 | 4 | 25 |

TABLE 2D-continued

Aldohexose conversion using 2-carboxyl phenylboronic acids.

| aldohexose | solvent | phenylboronic acid | metal chloride | T (° C.) | time (h) | HMF molar yield (%) |
|---|---|---|---|---|---|---|
| altrose | DMA | 2-carboxy | $MgCl_2 \cdot 6H_2O$ | 105 | 4 | 28 |
| altrose | DMA | 2-methoxycarbonyl | | 105 | 4 | 43 |
| altrose | DMA | 2-ethoxycarbonyl | | 105 | 4 | 49 |
| glucose | DMA | 2-carboxy | $MgCl_2 \cdot 6H_2O$ | 105 | 4 | 46 |
| glucose | DMA | 2-methoxycarbonyl | $MgCl_2 \cdot 6H_2O$ | 105 | 4 | 61 |
| glucose | DMA | 2-ethoxycarbonyl | $MgCl_2 \cdot 6H_2O$ | 105 | 4 | 56 |
| mannose | DMA | 2-carboxy | $MgCl_2 \cdot 6H_2O$ | 105 | 4 | 53 |
| mannose | DMA | 2-methoxycarbonyl | $MgCl_2 \cdot 6H_2O$ | 105 | 3 | 51 |
| mannose | DMA | 2-ethoxycarbonyl | $MgCl_2 \cdot 6H_2O$ | 105 | 4 | 54 |
| gulose | DMA | 2-carboxy | $MgCl_2 \cdot 6H_2O$ | 105 | 4 | 55 |
| gulose | DMA | 2-methoxycarbonyl | $MgCl_2 \cdot 6H_2O$ | 105 | 4 | 56 |
| gulose | DMA | 2-ethoxycarbonyl | $MgCl_2 \cdot 6H_2O$ | 105 | 4 | 49 |
| idose | DMA | 2-carboxy | $MgCl_2 \cdot 6H_2O$ | 105 | 4 | 48 |
| idose | DMA | 2-methoxycarbonyl | $MgCl_2 \cdot 6H_2O$ | 105 | 4 | 51 |
| idose | DMA | 2-ethoxycarbonyl | | 105 | 4 | 42 |
| galactose | DMA | 2-carboxy | $MgCl_2 \cdot 6H_2O$ | 105 | 4 | 38 |
| galactose | DMA | 2-methoxycarbonyl | | 105 | 4 | 50 |
| galactose | DMA | 2-ethoxycarbonyl | $MgCl_2 \cdot 6H_2O$ | 105 | 4 | 35 |
| talose | DMA | 2-carboxy | $MgCl_2 \cdot 6H_2O$ | 105 | 4 | 21 |
| talose | DMA | 2-methoxycarbonyl | $MgCl_2 \cdot 6H_2O$ | 105 | 4 | 30 |
| talose | DMA | 2-ethoxycarbonyl | $MgCl_2 \cdot 6H_2O$ | 105 | 4 | 22 |

Boronic acids were used as 1 eq. and $MgCl_2 \cdot 6H_2O$ as 2.5 eq. relative to the sugar. Sugars were used as 10 wt % relative to the DMA. Molar yield is relative to the sugars.

TABLE 3A

HMF from Cellobiose

| solvent | boronic acid | additive | T (° C.) | time (h) | HMF yield (%) |
|---|---|---|---|---|---|
| DMA | 2-carboxyphenyl | — | 110 | 6 | 0 |
| DMA | 2-carboxyphenyl | $MgCl_2 \cdot 6H_2O$ | 110 | 6 | 10 |
| DMA | 2-methoxycarbonylphenyl | — | 110 | 6 | 50 |
| DMA | 2-methoxycarbonylphenyl | $MgCl_2 \cdot 6H_2O$ | 110 | 5 | 37 |
| DMA | 2-ethoxycarbonylphenyl | — | 110 | 6 | 44 |
| DMA | 2-ethoxycarbonylphenyl | $MgCl_2 \cdot 6H_2O$ | 110 | 5 | 27 |
| [EMIM]Cl | 2-methoxycarbonylphenyl | $MgCl_2 \cdot 6H_2O$ | 110 | 1 | 27 |
| [EMIM]Cl | 2-methoxycarbonylphenyl | $MgCl_2 \cdot 6H_2O$ | 120 | 1 | 35 |
| [EMIM]Cl | 2-methoxycarbonylphenyl | $MgCl_2 \cdot 6H_2O$ | 130 | 0.5 | 36 |
| [EMIM]Cl | 2-methoxycarbonylphenyl | $MgCl_2 \cdot 6H_2O$ | 140 | 0.33 | 38 |
| DMA | 2-nitrophenyl | — | 105 | 4 | 0 |
| DMA | 2-nitrophenyl | $MgCl_2 \cdot 6H_2O$ | 105 | 4 | 0 |
| [EMIM]Cl | 2-nitrophenyl | — | 105 | 4 | 12 |
| [EMIM]Cl | 2-nitrophenyl | $MgCl_2 \cdot 6H_2O$ | 105 | 5 | 6 |
| DMA | 2-formylphenyl | — | 105 | 4 | 4 |
| DMA | 2-formylphenyl | $MgCl_2 \cdot 6H_2O$ | 105 | 4 | 2 |
| [EMIM]Cl | 2-formylphenyl | — | 105 | 3 | 7 |
| [EMIM]Cl | 2-formylphenyl | $MgCl_2 \cdot 6H_2O$ | 105 | 4 | 7 |
| DMA | 2-acetylphenyl | — | 105 | 4 | 0 |
| DMA | 2-acetylphenyl | $MgCl_2 \cdot 6H_2O$ | 105 | 4 | 0 |
| [EMIM]Cl | 2-acetylphenyl | — | 105 | 4 | 5 |
| [EMIM]Cl | 2-acetylphenyl | $MgCl_2 \cdot 6H_2O$ | 105 | 4 | 4 |
| DMA | 2-aminocarbonylphenyl | — | 105 | 4 | 0 |
| DMA | 2-aminocarbonylphenyl | $MgCl_2 \cdot 6H_2O$ | 105 | 4 | 2 |
| [EMIM]Cl | 2-aminocarbonylphenyl | — | 105 | 4 | 0 |
| [EMIM]Cl | 2-aminocarbonylphenyl | $MgCl_2 \cdot 6H_2O$ | 105 | 4 | 8 |

Boronic Acid is present at 1 equiv. and $MgCl_2 \cdot 6H_2O$ is present at 2 equiv.
Mol % is relative to the cellobiose in the reaction mixture and the yield is calculated taking into account the molar equivalents of glucose/cellobiose.

TABLE 3B

Saccharide conversion using 2-carboxyl phenylboronic acids.

| saccharide | solvent | phenylboronic acid | metal chloride | T (° C.) | time (h) | HMF molar yield (%) |
|---|---|---|---|---|---|---|
| cellobiose | DMA | 2-carboxy | | 110 | 6 | 0 |
| cellobiose | DMA | 2-carboxy | $MgCl_2 \cdot 6H_2O$ | 110 | 6 | 10 |

TABLE 3B-continued

Saccharide conversion using 2-carboxyl phenylboronic acids.

| saccharide | solvent | phenylboronic acid | metal chloride | T (° C.) | time (h) | HMF molar yield (%) |
|---|---|---|---|---|---|---|
| cellobiose | DMA | 2-methoxycarbonyl | | 110 | 6 | 49 |
| cellobiose | DMA | 2-methoxycarbonyl | MgCl$_2$•6H$_2$O | 110 | 5 | 37 |
| cellobiose | DMA | 2-ethoxycarbonyl | | 110 | 6 | 44 |
| cellobiose | DMA | 2-ethoxycarbonyl | MgCl$_2$•6H$_2$O | 110 | 5 | 27 |
| cellotriose | DMA | 2-ethoxycarbonyl | | 105 | 4 | 21 |
| cellotetraose | DMA | 2-ethoxycarbonyl | | 120 | 4 | 38 |
| maltose | DMA | 2-carboxy | MgCl$_2$•6H$_2$O | 105 | 4 | 4 |
| maltose | DMA | 2-methoxycarbonyl | MgCl$_2$•6H$_2$O | 105 | 4 | 7 |
| maltose | DMA | 2-ethoxycarbonyl | MgCl$_2$•6H$_2$O | 105 | 4 | 25 |
| sucrose | DMA | 2-carboxy | MgCl$_2$•6H$_2$O | 105 | 4 | 46 |
| sucrose | DMA | 2-methoxycarbonyl | MgCl$_2$•6H$_2$O | 105 | 4 | 41 |
| sucrose | DMA | 2-ethoxycarbonyl | | 105 | 4 | 46 |
| inulin | DMA | 2-carboxy | MgCl$_2$•6H$_2$O | 105 | 1 | 29 |
| inulin | DMA | 2-methoxycarbonyl | MgCl$_2$•6H$_2$O | 105 | 1 | 29 |
| inulin | DMA | 2-ethoxycarbonyl | | 105 | 2 | 39 |

Boronic acids were used at 1 eq. and MgCl$_2$•6H$_2$O at 2.5 eq. relative to the sugar. Sugars were used as 10 wt % relative to the solvent. Molar yield is relative to the sugars.

TABLE 4

Saccharide conversion using substituted phenylboronic acids in DMA.

| saccharide | phenylboronic acid | metal chloride | T (° C.) | time (h) | HMF molar yield (%) |
|---|---|---|---|---|---|
| glucose | 2-isobutylcarboxy | MgCl$_2$•6H$_2$O | 105 | 4 | 22 |
| glucose | 2-carboxy-3-trifluoromethyl | MgCl$_2$•6H$_2$O | 105 | 1 | 68 |
| glucose | 2-carboxy-3-methoxy | MgCl$_2$•6H$_2$O | 105 | 4 | 52 |
| glucose | 2-carboxy-4,5-dimethoxy | MgCl$_2$•6H$_2$O | 105 | 3 | 63 |
| glucose | 2-carboxy-4-fluoro | MgCl$_2$•6H$_2$O | 105 | 4 | 63 |
| glucose | 2-carboxy-4-chloro | MgCl$_2$•6H$_2$O | 105 | 4 | 61 |
| glucose | 2-methoxycarbonyl-5-trifluoromethyl | MgCl$_2$•6H$_2$O | 105 | 3 | 63 |
| glucose | 2-carboxy-5-fluoro | MgCl$_2$•6H$_2$O | 105 | 4 | 20 |
| glucose | 2-carboxy-5-chloro | MgCl$_2$•6H$_2$O | 105 | 1 | 70 |
| glucose | 2-methoxycarbonyl-5-chloro | MgCl$_2$•6H$_2$O | 105 | 4 | 64 |
| cellobiose | 2-carboxy-3-trifluoromethyl | | 105 | 4 | 64 |
| cellobiose | 2-carboxy-3-methoxy | | 105 | 3 | 43 |
| cellobiose | 2-carboxy-4,5-dimethoxy | | 105 | 3 | 38 |
| cellobiose | 2-methoxycarbonyl-5-trifluoromethyl | | 105 | 4 | 53 |
| cellobiose | 2-carboxy-5-chloro | | 105 | 4 | 66 |
| cellobiose | 2-methoxycarbonyl-5-chloro | | 105 | 4 | 48 |

Boronic acids were used as 1 eq. and MgCl$_2$•6H$_2$O as 2.5 eq. relative to the sugar.
Sugars were used as 10 wt % relative to the solvent.
Molar yield is relative to the sugars.

TABLE 5A

HMF from Cellulose in [EMIM]Cl

| acid, wt % | boronic acid, mol % | additive, mol % | T (° C.) | time (h) | HMF yield (%) |
|---|---|---|---|---|---|
| — | 2-carboxyphenyl, 200 | — | 120 | 4.50 | 0 |
| — | 2-methoxycarbonylphenyl, 200 | — | 120 | 4.50 | 0 |
| — | 2-ethoxycarbonylphenyl, 200 | — | 120 | 3.75 | 12 |
| HCl, 0.88 | 2-methoxycarbonylphenyl, 200 | — | 105 | 2 | 16 |
| HCl, 0.88 | 2-methoxycarbonylphenyl, 200 | MgCl$_2$•6H$_2$O, 400 | 105 | 1 | 26 |
| HCl, 0.88 | — | MgCl$_2$•6H$_2$O, 400 | 105 | 3 | 16 |
| HCl, 0.88 | 2-ethoxycarbonylphenyl, 200 | — | 105 | 1 | 22 |
| HCl, 0.88 | 2-ethoxycarbonylphenyl, 200 | MgCl$_2$•6H$_2$O, 400 | 105 | 1 | 29 |
| HCl, 0.88 | — | MgCl$_2$•6H$_2$O, 400 | 105 | 3 | 17 |
| HCl, 0.88 | — | — | 105 | 2 | 10 |
| HCl, 0.88 | 2-methoxycarbonylphenyl, 200 | — | 120 | 2 | 12 |
| HCl, 0.88 | 2-methoxycarbonylphenyl, 200 | MgCl$_2$•6H$_2$O, 400 | 120 | 2 | 28 |
| HCl, 0.88 | 2-ethoxycarbonylphenyl, 200 | — | 120 | 1 | 21 |
| HCl, 0.88 | 2-ethoxycarbonylphenyl, 200 | MgCl$_2$•6H$_2$O, 400 | 120 | 1 | 30 |
| HCl, 0.8 | 2-ethoxycarbonylphenyl, 200 | MgCl$_2$•6H$_2$O, 400 | 105 | 1 | 27 |
| H$_2$SO$_4$, 0.8 | 2-ethoxycarbonylphenyl, 200 | MgCl$_2$•6H$_2$O, 400 | 105 | 1 | 32 |
| H$_3$PO$_4$, 0.8 | 2-ethoxycarbonylphenyl, 200 | MgCl$_2$•6H$_2$O, 400 | 105 | 2 | 31 |
| AcOH, 0.8 | 2-ethoxycarbonylphenyl, 200 | MgCl$_2$•6H$_2$O, 400 | 105 | 3 | 29 |
| HCl, 0.33 | 2-ethoxycarbonylphenyl, 200 | MgCl$_2$•6H$_2$O, 400 | 105 | 2 | 26 |

TABLE 5A-continued

HMF from Cellulose in [EMIM]Cl

| acid, wt % | boronic acid, mol % | additive, mol % | T (° C.) | time (h) | HMF yield (%) |
|---|---|---|---|---|---|
| HCl, 0.61 | 2-ethoxycarbonylphenyl, 200 | MgCl$_2$•6H$_2$O, 400 | 105 | 1 | 30 |
| HCl, 0.88 | 2-ethoxycarbonylphenyl, 200 | MgCl$_2$•6H$_2$O, 400 | 105 | 1 | 30 |
| H$_2$SO$_4$, 0.33 | 2-ethoxycarbonylphenyl, 200 | MgCl$_2$•6H$_2$O, 400 | 105 | 1 | 27 |
| H$_2$SO$_4$, 0.61 | 2-ethoxycarbonylphenyl, 200 | MgCl$_2$•6H$_2$O, 400 | 105 | 1 | 30 |
| H$_2$SO$_4$, 0.88 | 2-ethoxycarbonylphenyl, 200 | MgCl$_2$•6H$_2$O, 400 | 105 | 1 | 32 |
| H$_3$PO$_4$, 0.33 | 2-ethoxycarbonylphenyl, 200 | MgCl$_2$•6H$_2$O, 400 | 105 | 2 | 32 |
| H$_3$PO$_4$, 0.61 | 2-ethoxycarbonylphenyl, 200 | MgCl$_2$•6H$_2$O, 400 | 105 | 2 | 28 |
| H$_3$PO$_4$, 0.88 | 2-ethoxycarbonylphenyl, 200 | MgCl$_2$•6H$_2$O, 400 | 105 | 1 | 26 |
| H$_2$SO$_4$, 0.88 | 2-methoxycarbonylphenyl, 200 | MgCl$_2$•6H$_2$O, 940 | 105 | 1 | 32 |
| H$_2$SO$_4$, 0.88 | 2-methoxycarbonylphenyl, 200 | MgCl$_2$•6H$_2$O, 720 | 105 | 1 | 32 |
| H$_2$SO$_4$, 0.88 | 2-methoxycarbonylphenyl, 200 | MgCl$_2$•6H$_2$O, 500 | 105 | 1 | 33 |
| H$_2$SO$_4$, 0.88 | 2-methoxycarbonylphenyl, 200 | MgCl$_2$•6H$_2$O, 260 | 105 | 1 | 29 |
| H$_2$SO$_4$, 0.88 | 2-methoxycarbonylphenyl, 400 | MgCl$_2$•6H$_2$O, 400 | 105 | 1 | 29 |
| H$_2$SO$_4$, 0.88 | 2-methoxycarbonylphenyl, 340 | MgCl$_2$•6H$_2$O, 400 | 105 | 1 | 35 |
| H$_2$SO$_4$, 0.88 | 2-methoxycarbonylphenyl, 260 | MgCl$_2$•6H$_2$O, 400 | 105 | 1 | 33 |
| H$_2$SO$_4$, 0.88 | 2-methoxycarbonylphenyl, 160 | MgCl$_2$•6H$_2$O, 400 | 105 | 1 | 36 |
| H$_2$SO$_4$, 0.88 | 2-methoxycarbonylphenyl, 120 | MgCl$_2$•6H$_2$O, 400 | 105 | 0.5 | 39 |
| H$_2$SO$_4$, 0.88 | 2-methoxycarbonylphenyl, 80 | MgCl$_2$•6H$_2$O, 400 | 105 | 1 | 29 |
| H$_2$SO$_4$, 0.88 | 2-methoxycarbonylphenyl, 40 | MgCl$_2$•6H$_2$O, 400 | 105 | 1 | 22 |
| H$_2$SO$_4$, 0.88 | 2-ethoxycarbonylphenyl, 200 | MgCl$_2$•6H$_2$O, 940 | 105 | 1 | 32 |
| H$_2$SO$_4$, 0.88 | 2-ethoxycarbonylphenyl, 200 | MgCl$_2$•6H$_2$O, 720 | 105 | 1 | 32 |
| H$_2$SO$_4$, 0.88 | 2-ethoxycarbonylphenyl, 200 | MgCl$_2$•6H$_2$O, 500 | 105 | 1 | 30 |
| H$_2$SO$_4$, 0.88 | 2-ethoxycarbonylphenyl, 200 | MgCl$_2$•6H$_2$O, 260 | 105 | 1 | 26 |
| H$_2$SO$_4$, 0.88 | 2-ethoxycarbonylphenyl, 400 | MgCl$_2$•6H$_2$O, 400 | 105 | 1 | 26 |
| H$_2$SO$_4$, 0.88 | 2-ethoxycarbonylphenyl, 340 | MgCl$_2$•6H$_2$O, 400 | 105 | 1 | 25 |
| H$_2$SO$_4$, 0.88 | 2-ethoxycarbonylphenyl, 260 | MgCl$_2$•6H$_2$O, 400 | 105 | 1 | 26 |
| H$_2$SO$_4$, 0.88 | 2-ethoxycarbonylphenyl, 160 | MgCl$_2$•6H$_2$O, 400 | 105 | 1 | 30 |
| HCl, 0.61 | 2-methoxycarbonylphenyl, 120 | MgCl$_2$•6H$_2$O, 500 | 105 | 2 | 39 |
| HCl, 0.61 | 2-methoxycarbonylphenyl, 120 | MgCl$_2$•6H$_2$O, 300 | 105 | 2 | 39 |
| HCl, 0.61 | 2-ethoxycarbonylphenyl, 160 | MgCl$_2$•6H$_2$O, 500 | 105 | 2 | 38 |
| HCl, 0.61 | 2-ethoxycarbonylphenyl, 160 | MgCl$_2$•6H$_2$O, 300 | 105 | 2 | 38 |
| H$_2$SO$_4$, 0.88 | 2-methoxycarbonylphenyl, 120 | MgCl$_2$•6H$_2$O, 500 | 105 | 1 | 41 |
| H$_2$SO$_4$, 0.88 | 2-methoxycarbonylphenyl, 120 | MgCl$_2$•6H$_2$O, 300 | 105 | 1 | 38 |
| H$_2$SO$_4$, 0.88 | 2-ethoxycarbonylphenyl, 160 | MgCl$_2$•6H$_2$O, 500 | 105 | 1 | 36 |
| H$_2$SO$_4$, 0.88 | 2-ethoxycarbonylphenyl, 160 | MgCl$_2$•6H$_2$O, 300 | 105 | 1 | 36 |
| H$_3$PO$_4$, 0.33 | 2-methoxycarbonylphenyl, 160 | MgCl$_2$•6H$_2$O, 500 | 105 | 2 | 17 |
| H$_3$PO$_4$, 0.33 | 2-methoxycarbonylphenyl, 120 | MgCl$_2$•6H$_2$O, 300 | 105 | 2 | 12 |
| H$_3$PO$_4$, 0.33 | 2-ethoxycarbonylphenyl, 160 | MgCl$_2$•6H$_2$O, 500 | 105 | 2 | 23 |
| H$_3$PO$_4$, 0.33 | 2-ethoxycarbonylphenyl, 160 | MgCl$_2$•6H$_2$O, 300 | 105 | 2 | 29 |
| H$_2$SO$_4$, 0.88 | 2-methoxycarbonylphenyl, 120 | MgCl$_2$, 1000 | 105 | 4 | 0 |

TABLE 5A-continued

HMF from Cellulose in [EMIM]Cl

| acid, wt % | boronic acid, mol % | additive, mol % | T (° C.) | time (h) | HMF yield (%) |
|---|---|---|---|---|---|
| $H_2SO_4$, 0.88 | 2-ethoxycarbonylphenyl, 160 | $MgCl_2$, 1000 | 105 | 4 | 0 |
| $H_2SO_4$, 0.88 | 2-methoxycarbonylphenyl, 200 | $MgBr_2 \cdot 6H_2O$, 400 | 105 | 1 | 26 |
| $H_2SO_4$, 0.88 | 2-ethoxycarbonylphenyl, 200 | $MgBr_2 \cdot 6H_2O$, 400 | 105 | 1 | 23 |
| $H_2SO_4$, 0.88 | 2-methoxycarbonylphenyl, 200 | $MgI_2 \cdot 6H_2O$, 400 | 105 | 1 | 10 |
| $H_2SO_4$, 0.88 | 2-ethoxycarbonylphenyl, 200 | $MgI_2 \cdot 6H_2O$, 400 | 105 | 1 | 8 |

Wt % is relative to the [EMIM]Cl.
Mol % is relative to glucose in the cellulose in the reaction mixture;
AcOH is acetic acid.

TABLE 5B

Catalyst concentration determination for cellulose to HMF conversion in [EMIM]Cl

| acid, wt % | boronic acid, mol % | additive, mol % | T (° C.) | time (h) | HMF molar yield (%) |
|---|---|---|---|---|---|
| HCl, 0.33 | 2-ethoxycarbonylphenyl, 200 | $MgCl_2 \cdot 6H_2O$, 400 | 105 | 2 | 26 |
| HCl, 0.61 | 2-ethoxycarbonylphenyl, 200 | $MgCl_2 \cdot 6H_2O$, 400 | 105 | 1 | 30 |
| HCl, 0.88 | 2-ethoxycarbonylphenyl, 200 | $MgCl_2 \cdot 6H_2O$, 400 | 105 | 1 | 30 |
| $H_2SO_4$, 0.33 | 2-ethoxycarbonylphenyl, 200 | $MgCl_2 \cdot 6H_2O$, 400 | 105 | 1 | 27 |
| $H_2SO_4$, 0.61 | 2-ethoxycarbonylphenyl, 200 | $MgCl_2 \cdot 6H_2O$, 400 | 105 | 1 | 30 |
| $H_2SO_4$, 0.88 | 2-ethoxycarbonylphenyl, 200 | $MgCl_2 \cdot 6H_2O$, 400 | 105 | 1 | 32 |
| $H_3PO_4$, 0.33 | 2-ethoxycarbonylphenyl, 200 | $MgCl_2 \cdot 6H_2O$, 400 | 105 | 2 | 32 |
| $H_3PO_4$, 0.61 | 2-ethoxycarbonylphenyl, 200 | $MgCl_2 \cdot 6H_2O$, 400 | 105 | 2 | 28 |
| $H_3PO_4$, 0.88 | 2-ethoxycarbonylphenyl, 200 | $MgCl_2 \cdot 6H_2O$, 400 | 105 | 1 | 26 |
| $H_2SO_4$, 0.88 | 2-methoxycarbonylphenyl, 200 | $MgCl_2 \cdot 6H_2O$, 940 | 105 | 1 | 32 |
| $H_2SO_4$, 0.88 | 2-methoxycarbonylphenyl, 200 | $MgCl_2 \cdot 6H_2O$, 720 | 105 | 1 | 32 |
| $H_2SO_4$, 0.88 | 2-methoxycarbonylphenyl, 200 | $MgCl_2 \cdot 6H_2O$, 500 | 105 | 1 | 33 |
| $H_2SO_4$, 0.88 | 2-methoxycarbonylphenyl, 200 | $MgCl_2 \cdot 6H_2O$, 260 | 105 | 1 | 29 |
| $H_2SO_4$, 0.88 | 2-methoxycarbonylphenyl, 400 | $MgCl_2 \cdot 6H_2O$, 400 | 105 | 1 | 29 |
| $H_2SO_4$, 0.88 | 2-methoxycarbonylphenyl, 340 | $MgCl_2 \cdot 6H_2O$, 400 | 105 | 1 | 35 |
| $H_2SO_4$, 0.88 | 2-methoxycarbonylphenyl, 260 | $MgCl_2 \cdot 6H_2O$, 400 | 105 | 1 | 33 |
| $H_2SO_4$, 0.88 | 2-methoxycarbonylphenyl, 160 | $MgCl_2 \cdot 6H_2O$, 400 | 105 | 1 | 36 |
| $H_2SO_4$, 0.88 | 2-methoxycarbonylphenyl, 120 | $MgCl_2 \cdot 6H_2O$, 400 | 105 | 0.5 | 39 |
| $H_2SO_4$, 0.88 | 2-methoxycarbonylphenyl, 80 | $MgCl_2 \cdot 6H_2O$, 400 | 105 | 2 | 29 |
| $H_2SO_4$, 0.88 | 2-methoxycarbonylphenyl, 40 | $MgCl_2 \cdot 6H_2O$, 400 | 105 | 2 | 22 |
| $H_2SO_4$, 0.88 | 2-ethoxycarbonylphenyl, 200 | $MgCl_2 \cdot 6H_2O$, 940 | 105 | 1 | 32 |
| $H_2SO_4$, 0.88 | 2-ethoxycarbonylphenyl, 200 | $MgCl_2 \cdot 6H_2O$, 720 | 105 | 1 | 32 |
| $H_2SO_4$, 0.88 | 2-ethoxycarbonylphenyl, 200 | $MgCl_2 \cdot 6H_2O$, 500 | 105 | 1 | 33 |
| $H_2SO_4$, 0.88 | 2-ethoxycarbonylphenyl, 200 | $MgCl_2 \cdot 6H_2O$, 260 | 105 | 1 | 29 |
| $H_2SO_4$, 0.88 | 2-ethoxycarbonylphenyl, 400 | $MgCl_2 \cdot 6H_2O$, 400 | 105 | 1 | 26 |
| $H_2SO_4$, 0.88 | 2-ethoxycarbonylphenyl, 340 | $MgCl_2 \cdot 6H_2O$, 400 | 105 | 1 | 25 |
| $H_2SO_4$, 0.88 | 2-ethoxycarbonylphenyl, 260 | $MgCl_2 \cdot 6H_2O$, 400 | 105 | 1 | 26 |
| $H_2SO_4$, 0.88 | 2-ethoxycarbonylphenyl, 160 | $MgCl_2 \cdot 6H_2O$, 400 | 105 | 1 | 30 |

Wt % is relative to the [EMIM]Cl.
Mol % is relative to the cellulose in the reaction.

TABLE 5C

Presently preferred reaction conditions for cellulose conversion to HMF in [EMIM]Cl

| acid, wt % | boronic acid, mol % | additive, mol % | T (° C.) | time (h) | HMF molar yield (%) |
|---|---|---|---|---|---|
| HCl, 0.61 | 2-methoxycarbonylphenyl, 120 | $MgCl_2 \cdot 6H_2O$, 500 | 105 | 2 | 39 |
| HCl, 0.61 | 2-methoxycarbonylphenyl, 120 | $MgCl_2 \cdot 6H_2O$, 300 | 105 | 2 | 39 |
| HCl, 0.61 | 2-ethoxycarbonylphenyl, 160 | $MgCl_2 \cdot 6H_2O$, 500 | 105 | 2 | 38 |
| HCl, 0.61 | 2-ethoxycarbonylphenyl, 160 | $MgCl_2 \cdot 6H_2O$, 300 | 105 | 2 | 38 |
| $H_2SO_4$, 0.88 | 2-methoxycarbonylphenyl, 120 | $MgCl_2 \cdot 6H_2O$, 500 | 105 | 1 | 41 |
| $H_2SO_4$, 0.88 | 2-methoxycarbonylphenyl, 120 | $MgCl_2 \cdot 6H_2O$, 300 | 105 | 1 | 38 |
| $H_2SO_4$, 0.88 | 2-ethoxycarbonylphenyl, 160 | $MgCl_2 \cdot 6H_2O$, 500 | 105 | 1 | 36 |
| $H_2SO_4$, 0.88 | 2-ethoxycarbonylphenyl, 160 | $MgCl_2 \cdot 6H_2O$, 300 | 105 | 1 | 36 |
| $H_3PO_4$, 0.33 | 2-methoxycarbonylphenyl, 120 | $MgCl_2 \cdot 6H_2O$, 500 | 105 | 2 | 17 |
| $H_3PO_4$, 0.33 | 2-methoxycarbonylphenyl, 120 | $MgCl_2 \cdot 6H_2O$, 300 | 105 | 2 | 12 |
| $H_3PO_4$, 0.33 | 2-ethoxycarbonylphenyl, 160 | $MgCl_2 \cdot 6H_2O$, 500 | 105 | 2 | 23 |
| $H_3PO_4$, 0.33 | 2-ethoxycarbonylphenyl, 160 | $MgCl_2 \cdot 6H_2O$, 300 | 105 | 2 | 29 |

Wt % is relative to the [EMIM]Cl.
Mol % is relative to the cellulose in the reaction.

TABLE 5D

Selected Data for Conversion of Cellulosic Substrates to HMF in Ionic Liquid

| substrate | ionic liquid | acid, wt % | additive, mol % | boronic acid, mol % | T (° C.) | time (h) | HMF yield (%) |
|---|---|---|---|---|---|---|---|
| cellulose | [EMIM]Cl | HCl, 0.61 | — | — | 105 | 2 | 39 |
| cellulose | [EMIM]Cl | HCl, 0.61 | MgCl$_2$•6H$_2$O, 300 | — | 105 | 2 | 39 |
| cellulose | [EMIM]Cl | HCl, 0.61 | — | 2-methoxycarbonylphenyl, 120 | 105 | 2 | 38 |
| cellulose | [EMIM]Cl | HCl, 0.61 | MgCl$_2$•6H$_2$O, 300 | 2-methoxycarbonylphenyl, 120 | 105 | 2 | 38 |
| cellulose | [EMIM]Cl | H$_2$SO$_4$, 0.88 | MgCl$_2$•6H$_2$O, 500 | 2-methoxycarbonylphenyl, 120 | 105 | 1 | 41 |
| cellulose | [EMIM]Cl | HCl, 0.61 | — | 2-ethoxycarbonylphenyl, 160 | 105 | 1 | 38 |
| cellulose | [EMIM]Cl | HCl, 0.61 | MgCl$_2$•6H$_2$O, 300 | 2-ethoxycarbonylphenyl, 160 | 105 | 1 | 36 |
| cellulose | [EMIM]Cl | H$_2$SO$_4$, 0.88 | MgCl$_2$•6H$_2$O, 300 | 2-ethoxycarbonylphenyl, 160 | 105 | 1 | 36 |
| cotton | [BMIM]Cl | — | MgCl$_2$•6H$_2$O, 300 | 2-methoxycarbonylphenyl, 160 | 105 | 2 | 12 |
| paper towel | [EMIM]Cl | HCl, 0.61 | MgCl$_2$•6H$_2$O, 300 | 2-ethoxycarbonylphenyl, 160 | 105 | 2 | 23 |
| newspaper | [BMIM]Cl | — | MgCl$_2$•6H$_2$O, 300 | 2-ethoxycarbonylphenyl, 160 | 105 | 2 | 29 |

Substrates were at 5 wt % relative to the ionic liquid. Wt % is relative to the ionic liquid. Mol % and HMF yield (HPLC) are relative to glucose monomers within the substrate, which was assumed to be pure cellulose.

TABLE 6

HMF and Furfural from Lignocellulosic Biomass in [EMIM]Cl

| substrate | boronic acid, mol % | additive, mol % | T (° C.) | HMF yield (%) | furfural yield (%) |
|---|---|---|---|---|---|
| corn stover | 2-methoxycarbonylphenyl, 200 | MgCl$_2$•6H$_2$O, | 105 | 18 | 15 |
| corn stover | 2-ethoxycarbonylphenyl, 200 | MgCl$_2$•6H$_2$O, 500 | 105 | 9 | 14 |
| AFEX-treated corn stover | 2-methoxycarbonylphenyl, 200 | MgCl$_2$•6H$_2$O, 500 | 105 | 14 | 21 |
| AFEX-treated corn stover | 2-ethoxycarbonylphenyl, 200 | MgCl$_2$•6H$_2$O, 500 | 105 | 10 | 20 |

Mol % is relative to the cellulose content in the corn stover.
H$_2$SO$_4$ was added at less than 1% by weight of solvent.

TABLE 7

Fructose from Sugars

| sugar | solvent | boronic acid, mol % | additive, mol % | T (° C.) | time (h) | fructose yield (%) |
|---|---|---|---|---|---|---|
| glucose | DMA | — | MgO, 250 | 120 | 2 | 26 |
| glucose | DMA | 2-carboxyphenyl, 100 | MgO, 250 | 120 | 1 | 41 |
| glucose | DMA | 2-methoxycarbonylphenyl, 100 | MgO, 250 | 120 | 1 | 15 |
| glucose | DMA | 2-ethoxycarbonylphenyl, 100 | MgO, 250 | 120 | 1 | 16 |
| glucose | [EMIM]Cl | — | MgO, 250 | 105 | 4 | 9 |
| glucose | [EMIM]Cl | 2-carboxyphenyl, 100 | MgO, 250 | 105 | 4 | 24 |
| glucose | [EMIM]Cl | 2-methoxycarbonylphenyl, 100 | MgO, 250 | 105 | 4 | 15 |
| glucose | [EMIM]Cl | 2-ethoxycarbonylphenyl, 100 | MgO, 250 | 105 | 4 | 14 |
| glucose | [EMIM]Cl | — | MgO, 250 | 120 | 4 | 17 |
| glucose | [EMIM]Cl | 2-carboxyphenyl, 100 | MgO, 250 | 120 | 4 | 33 |
| glucose | [EMIM]Cl | 2-methoxycarbonylphenyl, 100 | MgO, 250 | 120 | 4 | 30 |
| glucose | [EMIM]Cl | 2-ethoxycarbonylphenyl, 100 | MgO, 250 | 120 | 4 | 27 |
| glucose | DMA | 2-carboxyphenyl, 100 | MgSO$_4$, 200 | 105 | 4 | 2 |
| glucose | DMA | 2-carboxyphenyl, 100 | MgSO$_4$•7H$_2$O, 200 | 105 | 4 | 2 |
| glucose | DMA | 2-carboxyphenyl, 100 | MgSO$_4$, 200 | 105 | 4 | 9 |
| glucose | DMA | 2-carboxyphenyl, 100 | MgSO$_4$•7H$_2$O, 200 | 105 | 4 | 6 |
| cellobiose | [EMIM]Cl | — | MgO, 200 | 105 | 4 | 0 |
| cellobiose | [EMIM]Cl | 2-carboxyphenyl, 100 | MgO, 200 | 105 | 4 | 0 |
| cellobiose | [EMIM]Cl | 2-methoxycarbonylphenyl, 100 | MgO, 200 | 105 | 4 | 0 |
| cellobiose | [EMIM]Cl | 2-ethoxycarbonylphenyl, 100 | MgO, 200 | 105 | 4 | 0 |
| cellulose | [EMIM]Cl | 2-methoxycarbonylphenyl, 60 | MgO, 1000 + H$_2$SO$_4$, 0.88 | 105 | 4 | 0 |
| cellulose | [EMIM]Cl | 2-ethoxycarbonylphenyl, 80 | MgO, 1000 + H$_2$SO$_4$, 0.88 | 105 | 4 | 0 |

Mol % is relative to glucose, glucose in cellobiose or estimated glucose in cellulose in the reaction mixture.

We claim:

1. A method for producing furans from a carbohydrate substrate, the method comprising heating a reaction mixture comprising the carbohydrate substrate, a 2-substituted phenylboronic acid or a salt or hydrate thereof and optionally a magnesium or calcium halide salt, in a polar aprotic solvent other than an ionic liquid, an ionic liquid or a mixture thereof, and wherein when the carbohydrate substrate is biomass or a carbohydrate polymer, dilute acid is also added to the reaction mixture.

2. The method of claim 1 wherein the reaction mixture comprises the magnesium or calcium halide salt.

3. The method of claim 1 wherein a selected amount of water is also present in the reaction mixture.

4. The method of claim 1 wherein the 2-substituted phenylboronate is represented by formula:

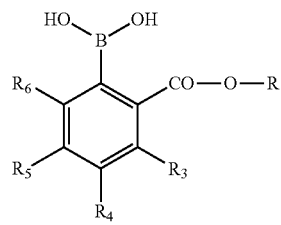

where:
R is selected from the group consisting of an alkyl group, a hydrogen, an aralkyl group, and an aryl group, each of which is optionally substituted; and $R_3$-$R_6$, independently, are selected from the group consisting of hydrogen, halogen, nitro, cyano, an alkyl group, an alkoxy group, an alkoxycarbonyl group, a carboxyalkyl group, an alkoxycarbonylalkyl group, an aminoalkyl group, an alkylaminoalkyl group, —COH, —$COR_7$, —$CO_2R_8$, —$NH_2$, —$CONH_2$, —$N(R_9)_2$, and —$CON(R_9)_2$, where $R_7$, $R_8$ and each $R_9$ are independently selected from the group consisting of an alkyl group, an aralkyl group and an aryl group and wherein one of $R_3$-$R_6$ is optionally a linker group covalently attached to a surface or suitable for attachment of the phenylboronate to a surface or one of $R_3$-$R_6$ is a reactive group suitable for forming a covalent attachment to a surface through a linker.

5. The method of claim 1 wherein the carbohydrate substrate is a mono- or disaccharide.

6. The method of claim 1 wherein the carbohydrate substrate is cellulose.

7. The method of claim 1 wherein the carbohydrate substrate is lignocellulosic biomass.

8. The method of claim 1 wherein the magnesium or calcium halide salt is magnesium chloride or calcium chloride.

9. The method of claim 1 wherein the polar aprotic solvent is N,N-dimethylacetamide.

10. The method of claim 1 wherein the reaction is conducted in an ionic liquid.

11. The method of claim 1 wherein the reaction is conducted in the mixture of an ionic liquid and a dipolar aprotic solvent other than an ionic liquid.

12. The method of claim 3 wherein the amount of water present in the reaction mixture is 6 or more molar equivalents with respect to the carbohydrate substrate.

13. The method of claim 1 wherein the carbohydrate substrate is lignocellulosic biomass, cellulose or hemicellulose and dilute acid is added to the reaction mixture.

14. The method of claim 1 wherein the 2-substituted phenylboronate is immobilized on a surface.

15. A method for making fructose from glucose, the method comprising heating the glucose in the presence of a 2-substituted phenylboronate, and magnesium oxide in a polar aprotic solvent, ionic liquid or a mixture thereof.

16. A catalyst for producing furans from a carbohydrate substrate, the catalyst comprising a 2-substituted phenylboronic acid or a 2-substituted phenylboronic acid immobilized on a surface; and the catalyst further comprises magnesium (II) or calcium (II).

17. The catalyst of claim 16, wherein the catalyst comprises a magnesium or calcium halide salt.

18. The catalyst of claim 16, wherein the 2-substituted phenylboronic is immobilized on a surface.

19. The catalyst of claim 16 wherein the 2-substituted phenylboronate is represented by formula:

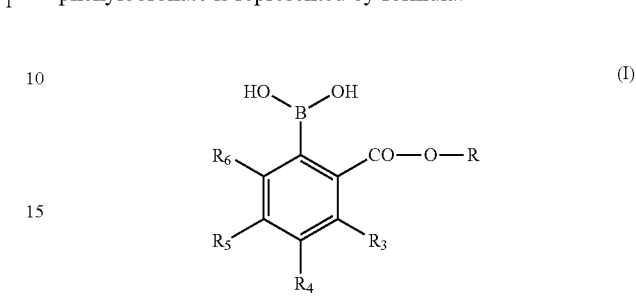

where
R is selected from the group consisting of an alkyl group, a hydrogen, an aralkyl group, and an aryl group, each of which is optionally substituted; and $R_3$-$R_6$, independently, are selected from the group consisting of hydrogen, halogen, nitro, cyano, an alkyl group, an alkoxy group, an alkoxycarbonyl group, a carboxyalkyl group, an alkoxycarbonylalkyl group, an aminoalkyl group, an alkylaminoalkyl group, —COH, —$COR_7$, —$CO_2R_8$, —$NH_2$, —$CONH_2$, —$N(R_9)_2$, and —$CON(R_9)_2$, where $R_7$, $R_8$ and each $R_9$ are independently selected from the group consisting of an alkyl group, an aralkyl group and an aryl group.

20. The catalyst of claim 19 wherein R is a hydrogen or an alkyl group having 1-3 carbon atoms.

21. The catalyst of claim 16 wherein a molar ratio of 2-substituted phenylboronate to magnesium(II), calcium (II) or a mixture thereof is 0.5 to 5.

22. The method of claim 1 wherein the 2-substituted phenylboronate is represented by formula:

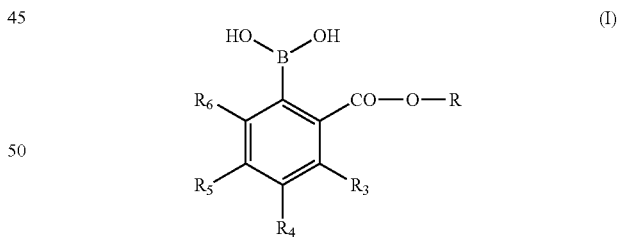

where:
R is selected from the group consisting of hydrogen and an unsubstituted alkyl group; and $R_3$-$R_6$, independently, are selected from the group consisting of hydrogen, halogen, nitro, cyano, an alkyl group, an alkoxy group, —COH, —$COR_7$, and —$CO_2R_8$, where $R_7$ and $R_8$ are independently selected from the group consisting of an alkyl group, an aralkyl group and an aryl group.

23. The method of claim 1 wherein the 2-substituted phenylboronate is represented by formula:

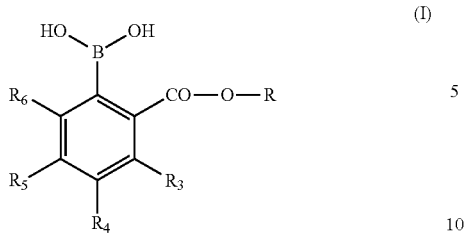

where:
R is selected from the group consisting of hydrogen and an unsubstituted alkyl group; and
$R_3$-$R_6$, independently, are selected from the group consisting of hydrogen, an alkyl group, an alkoxy group, and —$CO_2R_8$, where $R_7$ and $R_8$ are independently selected from the group consisting of an alkyl groups.

24. The method of claim 1 wherein the 2-substituted phenylboronate is selected from the group consisting of 2-carboxy phenylboronate, 2-methoxycarbonylphenylboronate, and 2-ethoxycarbonyl phenylboronate.

* * * * *